(12) United States Patent
Crawford et al.

(10) Patent No.: US 11,857,273 B2
(45) Date of Patent: *Jan. 2, 2024

(54) ULTRASONIC ROBOTIC SURGICAL NAVIGATION

(71) Applicant: GLOBUS MEDICAL, INC., Audubon, PA (US)

(72) Inventors: Neil Crawford, Chandler, AZ (US); Paden Troxell, Curwensville, PA (US); Dale Earle, Derry, NH (US); Michael Robinson, Concord, NH (US); Keiichi Matsuda, London (GB); Isaac Dulin, Somerville, MA (US)

(73) Assignee: Globus Medical, Inc., Audubon, PA (US)

( * ) Notice: Subject to any disclaimer, the term of this patent is extended or adjusted under 35 U.S.C. 154(b) by 217 days.

This patent is subject to a terminal disclaimer.

(21) Appl. No.: 17/368,190

(22) Filed: Jul. 6, 2021

(65) Prior Publication Data

US 2023/0009846 A1    Jan. 12, 2023

(51) Int. Cl.
*A61B 34/20* (2016.01)
*A61B 34/30* (2016.01)
*A61B 34/10* (2016.01)
*A61B 90/00* (2016.01)

(52) U.S. Cl.
CPC ............. *A61B 34/20* (2016.02); *A61B 34/10* (2016.02); *A61B 34/30* (2016.02); *A61B 90/06* (2016.02); *A61B 2034/107* (2016.02); *A61B 2034/2048* (2016.02); *A61B 2034/2057* (2016.02); *A61B 2034/2063* (2016.02); *A61B 2034/2065* (2016.02); *A61B 2090/062* (2016.02); *A61B 2090/3925* (2016.02)

(58) Field of Classification Search
CPC ......... A61B 34/20; A61B 34/25; A61B 34/30; A61B 2034/2063; A61B 2034/2065; A61B 2034/2068
See application file for complete search history.

(56) References Cited

U.S. PATENT DOCUMENTS

| | | | |
|---|---|---|---|
| 4,150,293 | A | 4/1979 | Franke |
| 5,246,010 | A | 9/1993 | Gazzara et al. |
| 5,354,314 | A | 10/1994 | Hardy et al. |
| 5,397,323 | A | 3/1995 | Taylor et al. |
| 5,598,453 | A | 1/1997 | Baba et al. |

(Continued)

OTHER PUBLICATIONS

US 8,231,638 B2, 07/2012, Swarup et al. (withdrawn)

*Primary Examiner* — Boniface Ngathi

(57) ABSTRACT

Surgical robot systems, anatomical structure tracker apparatuses, and US transducer apparatuses are disclosed. A surgical robot system includes a robot, a US transducer, and at least one processor. The robot includes a robot base, a robot arm coupled to the robot base, and an end-effector coupled to the robot arm. The end-effector is configured to guide movement of a surgical instrument. The US transducer is coupled to the end-effector and operative to output US imaging data of anatomical structure proximately located to the end-effector. The least one processor is operative to obtain an image volume for the patient and to track pose of the end-effector relative to anatomical structure captured in the image volume based on the US imaging data.

20 Claims, 37 Drawing Sheets

(56) References Cited

U.S. PATENT DOCUMENTS

| | | |
|---|---|---|
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Steves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Tastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |

(56) References Cited

U.S. PATENT DOCUMENTS

| | | |
|---|---|---|
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Willliams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 3,335,557 A1 | 12/2012 | Maschke |
| 8,332,012 B2 | 12/2012 | Kienzle, III |
| 8,333,755 B2 | 12/2012 | Cooper et al. |
| 8,335,552 B2 | 12/2012 | Stiles |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |

(56) References Cited

U.S. PATENT DOCUMENTS

| | | |
|---|---|---|
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |

(56) References Cited

U.S. PATENT DOCUMENTS

| | | |
|---|---|---|
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |

(56) References Cited

U.S. PATENT DOCUMENTS

| | | |
|---|---|---|
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |
| 2021/0100627 A1* | 4/2021 | Soper .................. A61B 18/02 |

\* cited by examiner

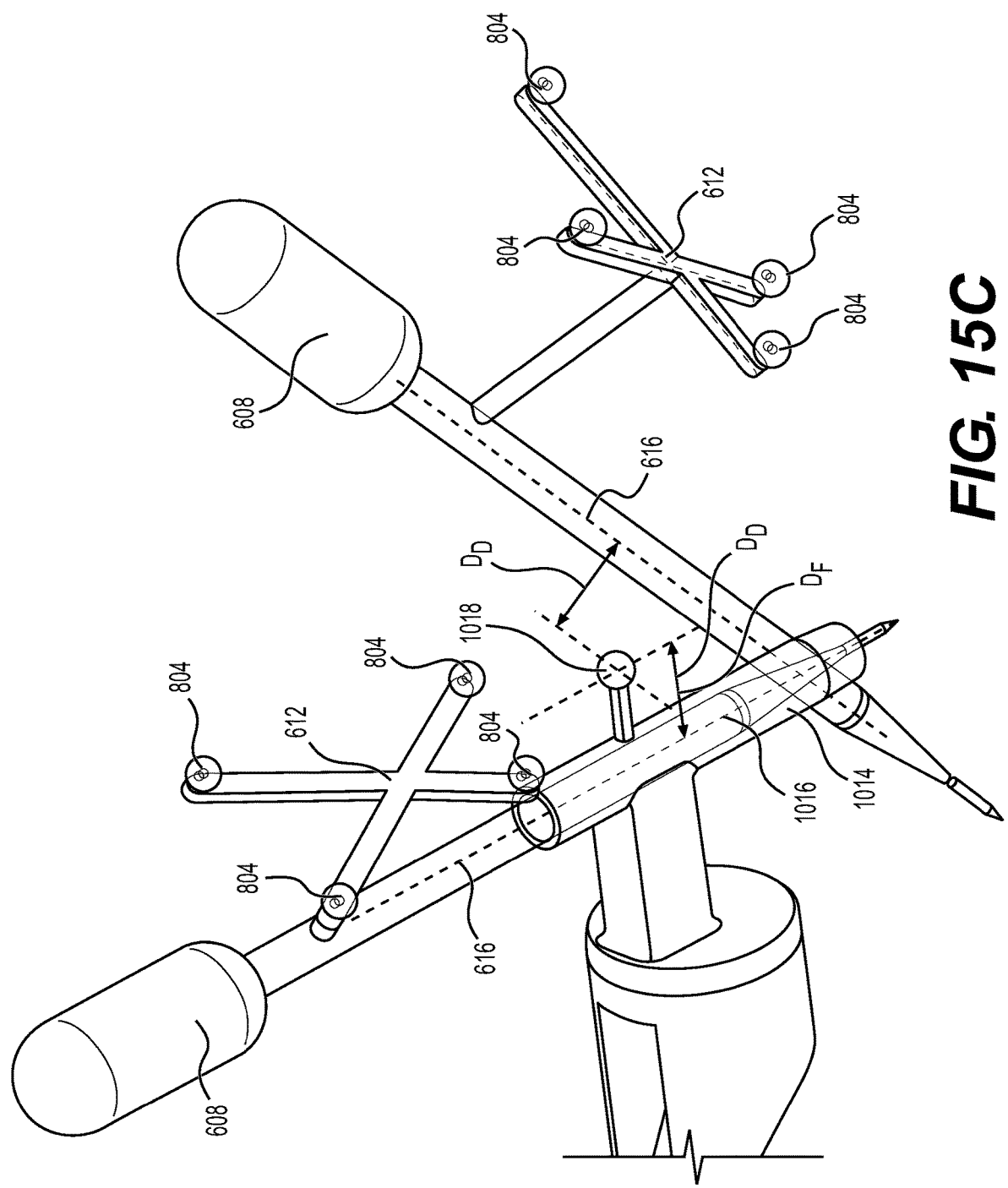

ULTRASONIC ROBOTIC SURGICAL NAVIGATION

FIELD

The present disclosure relates to position recognition systems and more particularly to end-effector and instrument tracking and manipulation during robot assisted surgical procedures.

BACKGROUND

Position recognition systems are used to determine the position of and track a particular object in 3-dimensions (3D). In robot assisted surgeries, for example, certain objects, such as surgical instruments, need to be tracked with a high degree of precision as the instrument is being positioned and moved by a robot or by a physician.

Infrared signal based position recognition systems may use passive and/or active sensors or markers for tracking the objects. Objects to be tracked may include passive sensors, such as reflective spherical balls, which are positioned at strategic locations on the object to be tracked. Infrared transmitters transmit a signal, and the reflective spherical balls reflect the signal to aid in determining the position of the object in 3D. In active sensors or markers, the objects to be tracked include active infrared transmitters, such as light emitting diodes (LEDs), and thus generate their own infrared signals for 3D detection.

With either active or passive tracking sensors, the system then geometrically resolves the 3-dimensional position of the active and/or passive sensors based on information from or with respect to one or more of the infrared cameras, digital signals, known locations of the active or passive sensors, distance, the time it took to receive the responsive signals, other known variables, or a combination thereof.

Some existing surgical robot systems utilize optical tracking registered to a medical image as feedback for positioning a robotic arm while also visualizing instruments. Surgical procedures using such systems can be performed relatively quickly and accurately, however the procedure ceases whenever blockage occurs in the line of sight from the patient reference tracker to the cameras. Additionally, many surgical workflows with existing surgical robotic systems require x-rays or computerized tomography (CT) scans during operation and/or registration procedures. The system and procedure described herein overcomes many of these limitations.

SUMMARY

Surgical robot systems, anatomical structure tracker apparatuses, and ultrasound (US) transducer apparatuses are disclosed.

Some embodiments are directed to a surgical robot system that includes a robot, a US transducer, and at least one processor ("processor"). The robot includes a robot base, a robot arm coupled to the robot base, and an end-effector coupled to the robot arm. The end-effector is configured to guide movement of a surgical instrument. The US transducer is coupled to the end-effector and operative to output US imaging data of anatomical structure proximately located to the end-effector. The processor is operative to obtain an image volume for the patient and to track pose of the end-effector relative to anatomical structure captured in the image volume based on the US imaging data.

Some other embodiments are directed to an anatomical structure tracker apparatus includes an optical tracking array and a US transducer. The optical tracking array includes a plurality of spaced apart markers. The US transducer is rigidly coupled to and spaced apart from the optical tracking array. The US transducer is output US imaging data of anatomical structure.

Some other embodiments are directed to a US transducer apparatus that includes a wire and a US transducer attached to an end of the wire. In some further embodiments, the wire comprises a Kirschner wire, and an optical tracking array having a plurality of spaced apart markers is attached to the rigid wire.

Other surgical robot systems, anatomical structure tracker apparatuses, and US transducer apparatuses according to embodiments of the inventive subject matter will be or become apparent to one with skill in the art upon review of the following drawings and detailed description. It is intended that all such additional surgical robot systems, anatomical structure tracker apparatuses, and US transducer apparatuses be included within this description, be within the scope of the present inventive subject matter, and be protected by the accompanying claims. Moreover, it is intended that all embodiments disclosed herein can be implemented separately or combined in any way and/or combination.

DESCRIPTION OF THE DRAWINGS

Aspects of the present disclosure are illustrated by way of example and are not limited by the accompanying drawings. In the drawings.

Figure 5:
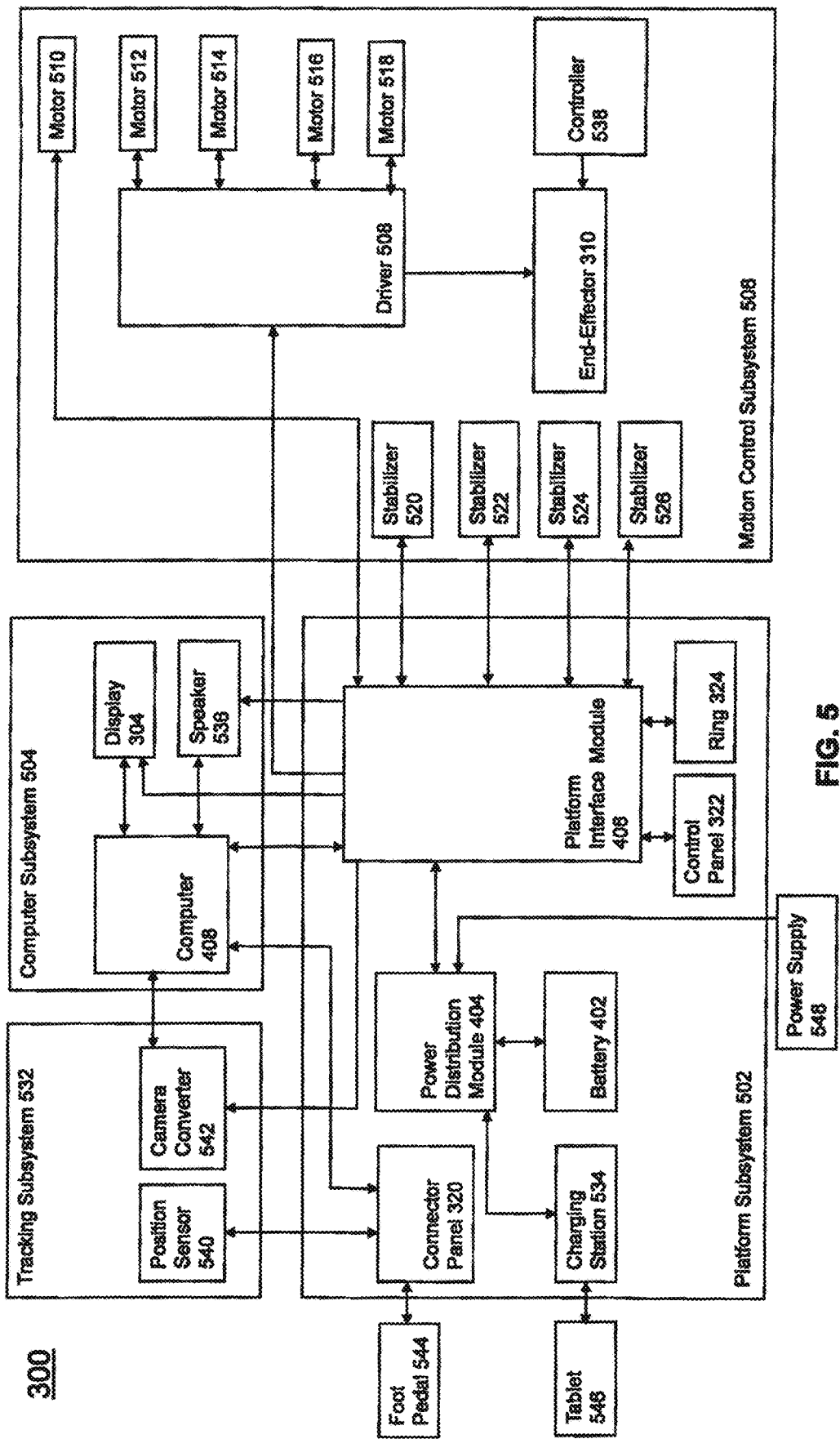
Figure 6:
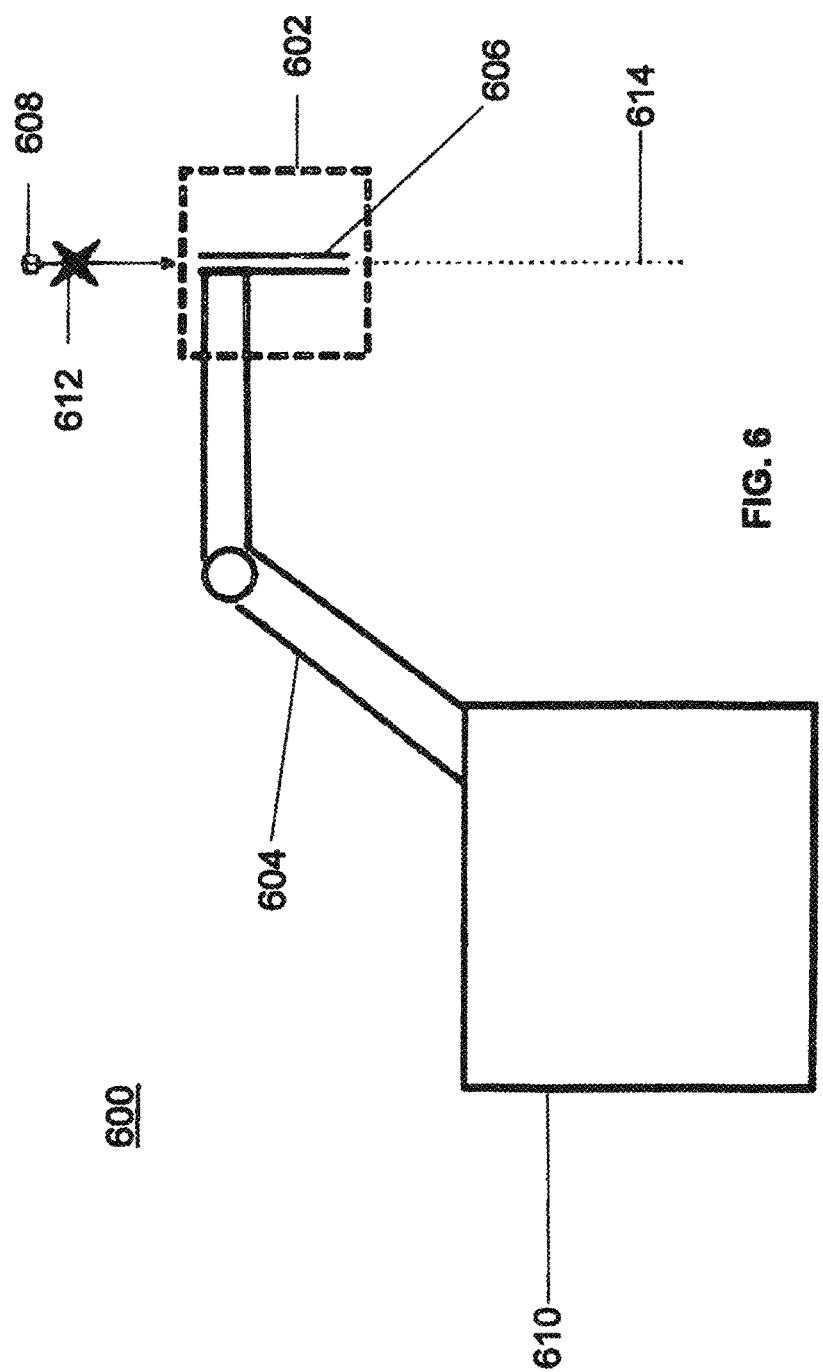
Figure 7C:
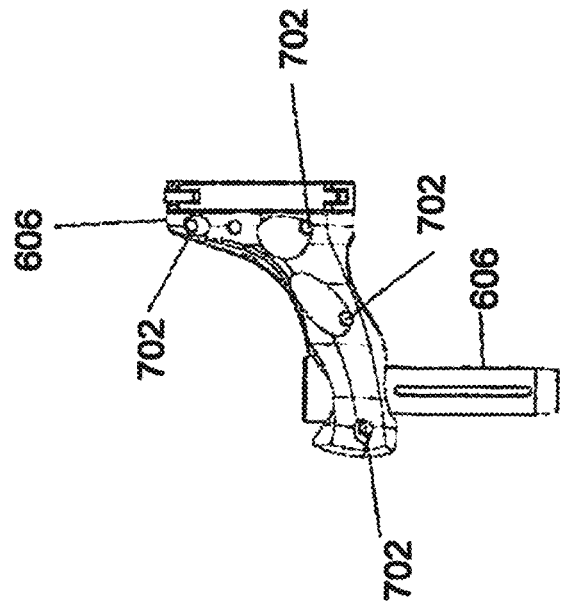
Figure 7A:
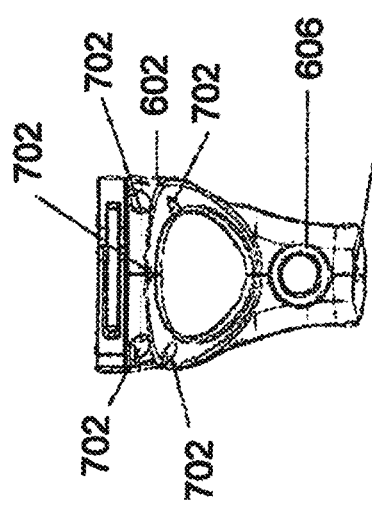
Figure 7B:
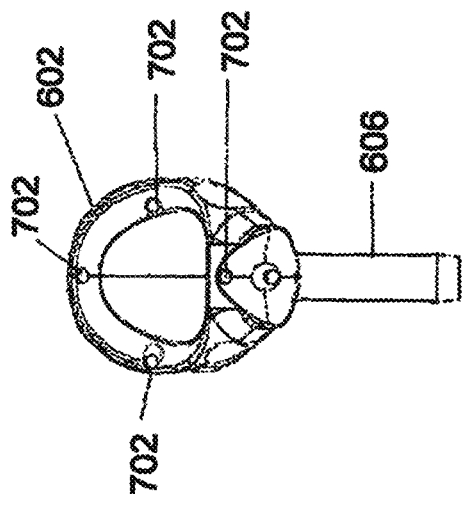
Figure 8:
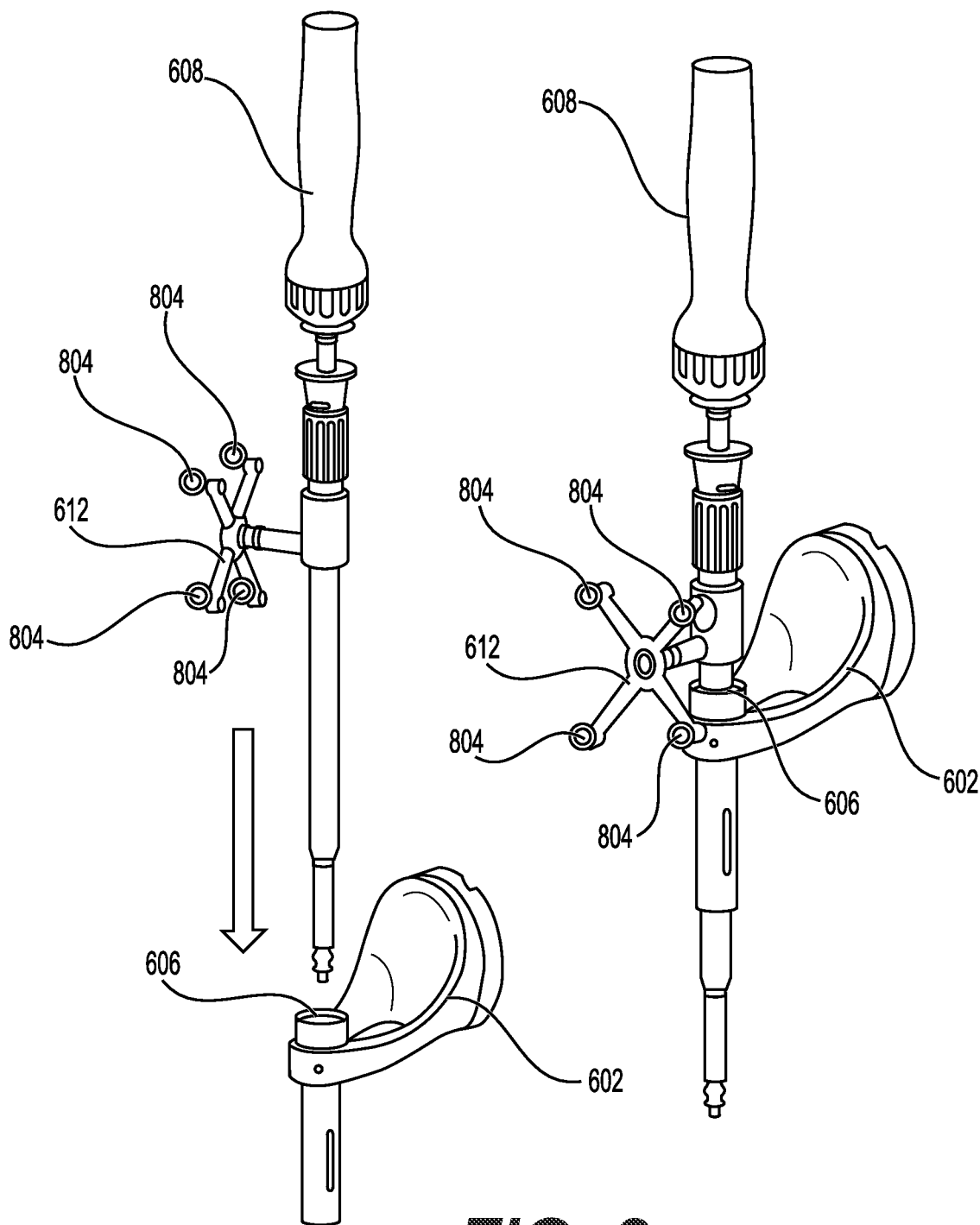
Figure 9:
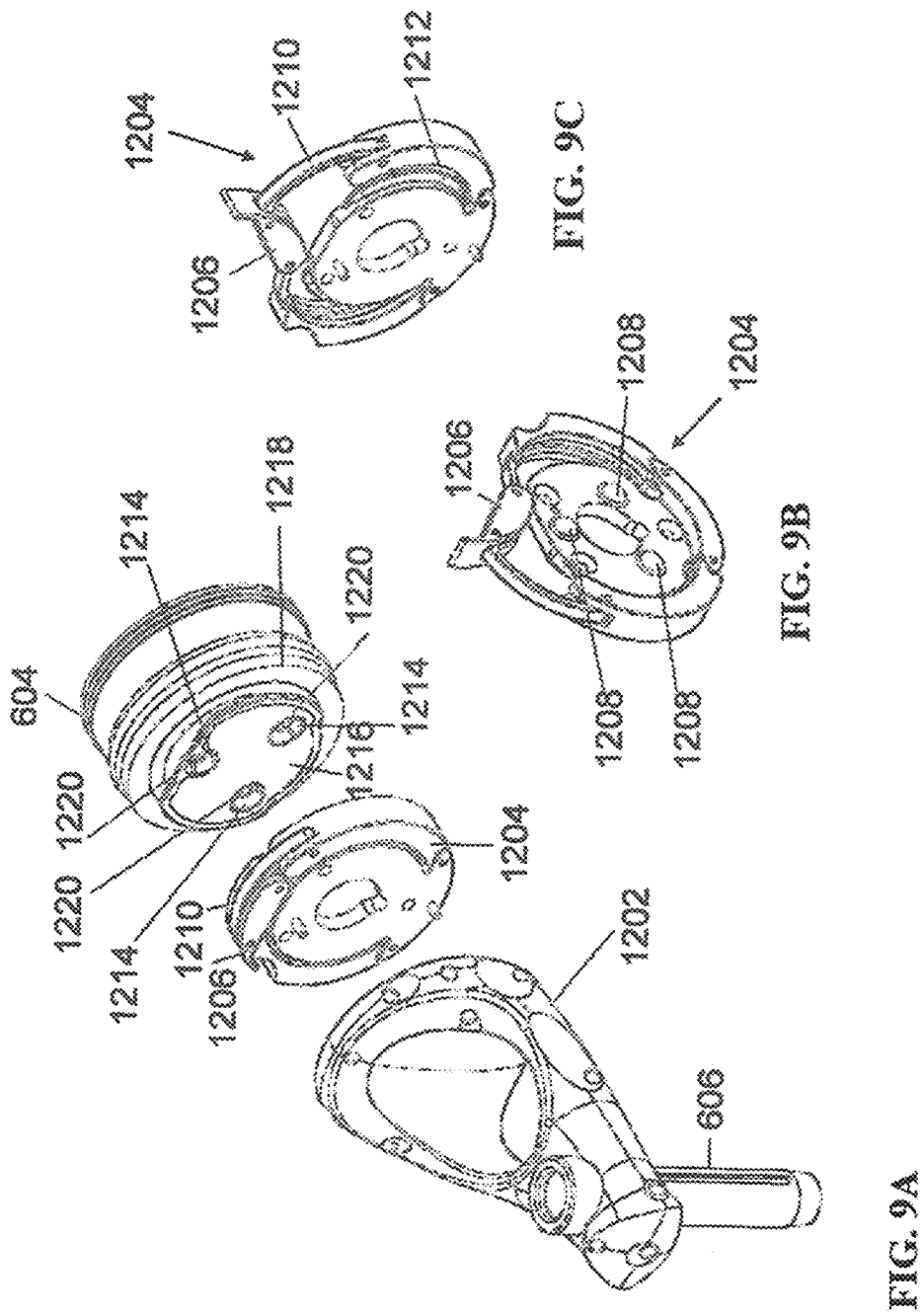
Figure 10:
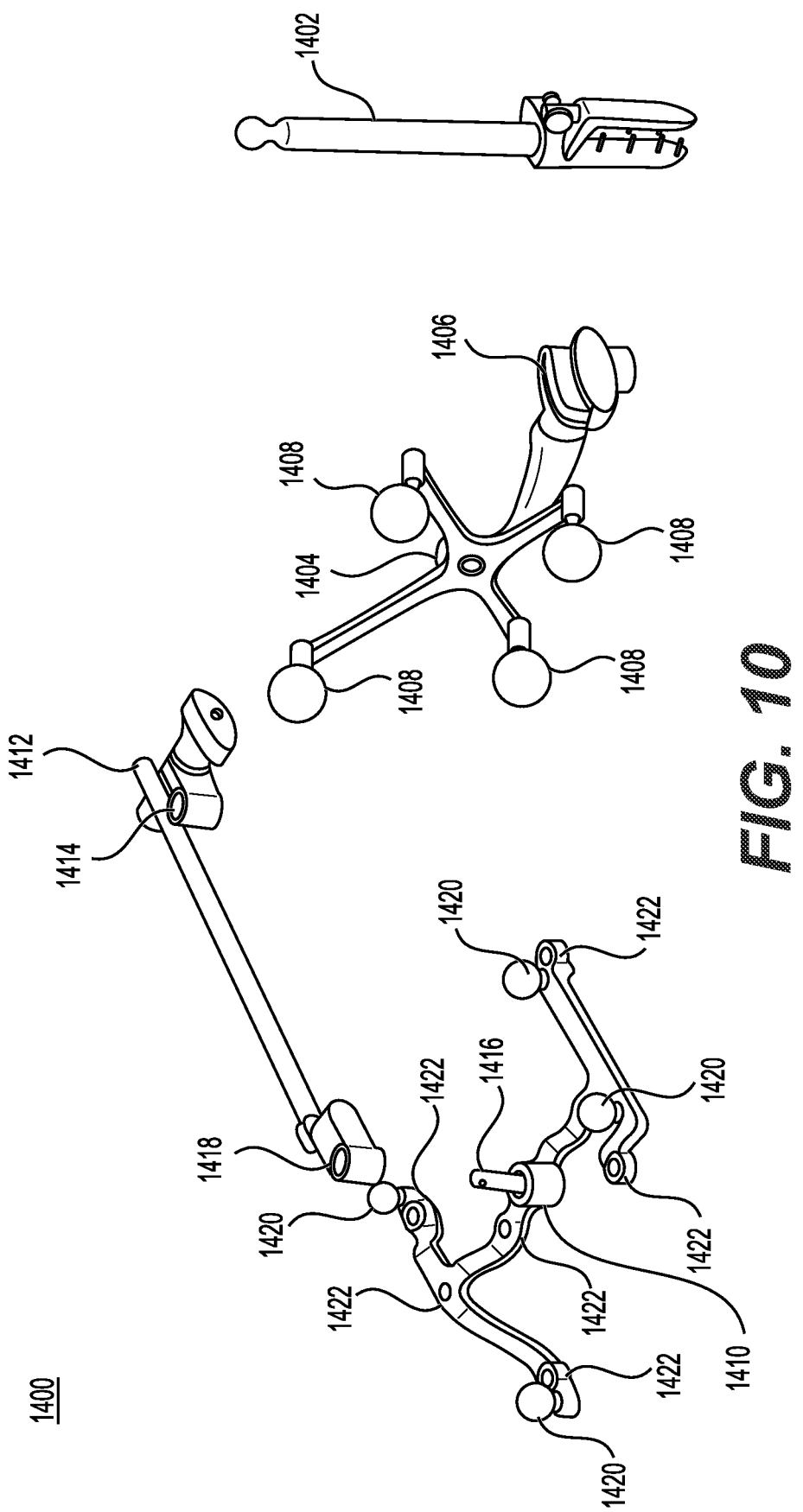
Figure 11:
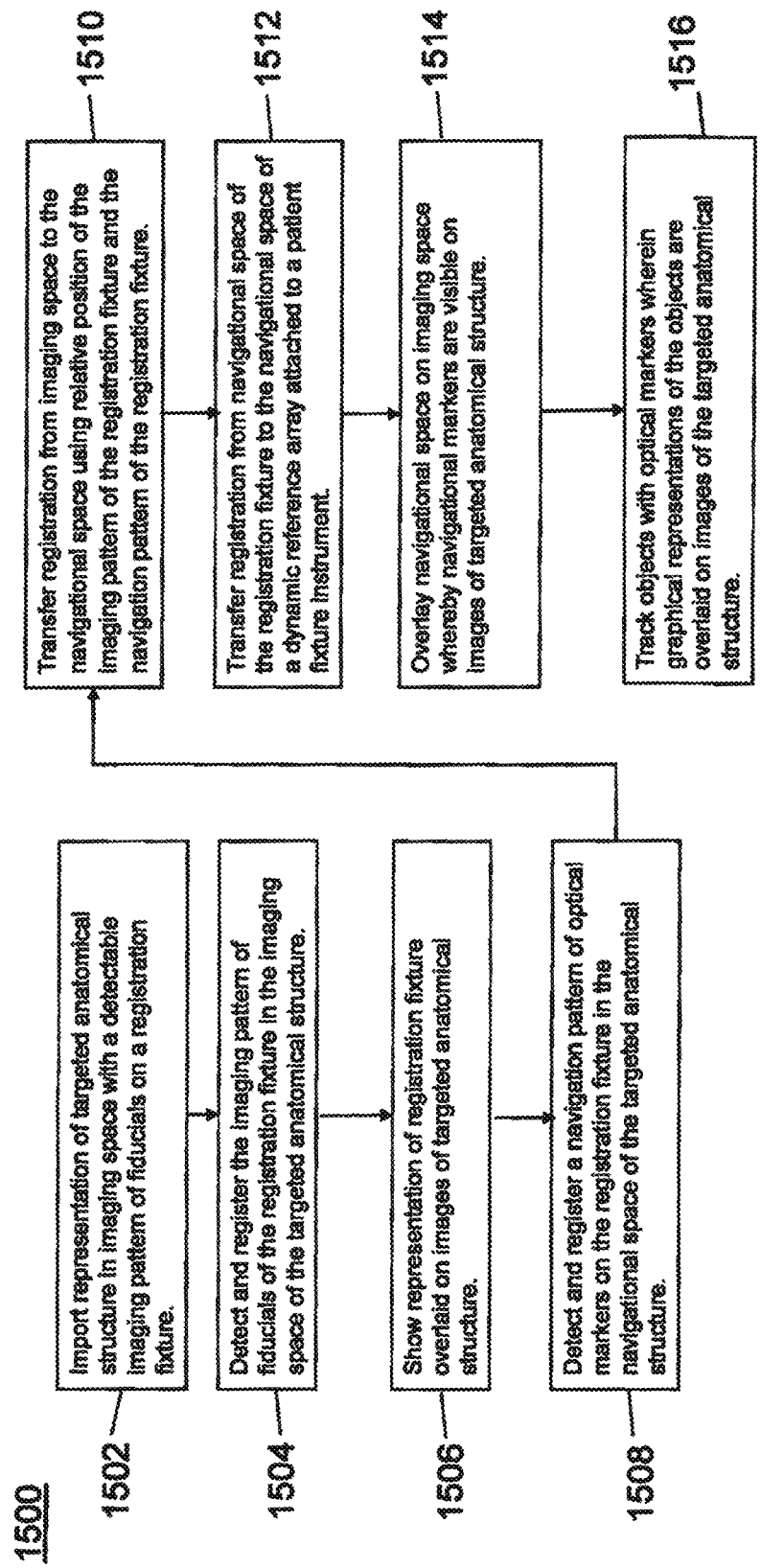
Figure 12A:
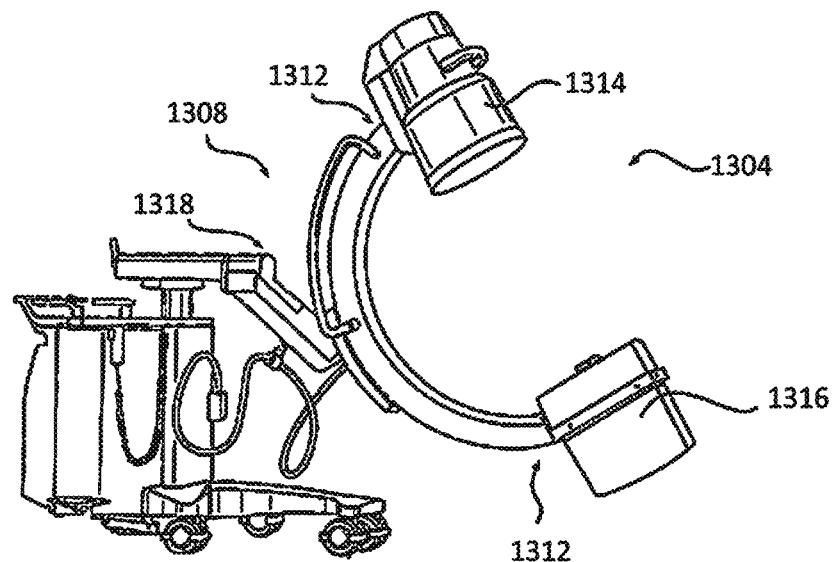
Figure 12B:
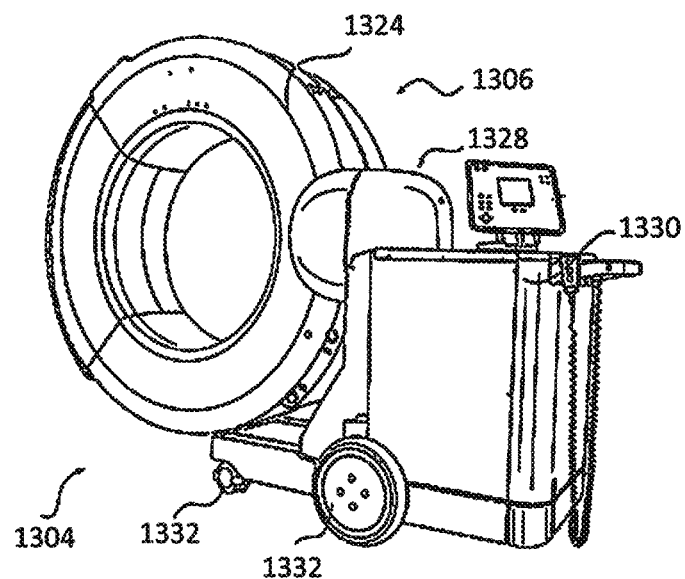
Figure 13A:
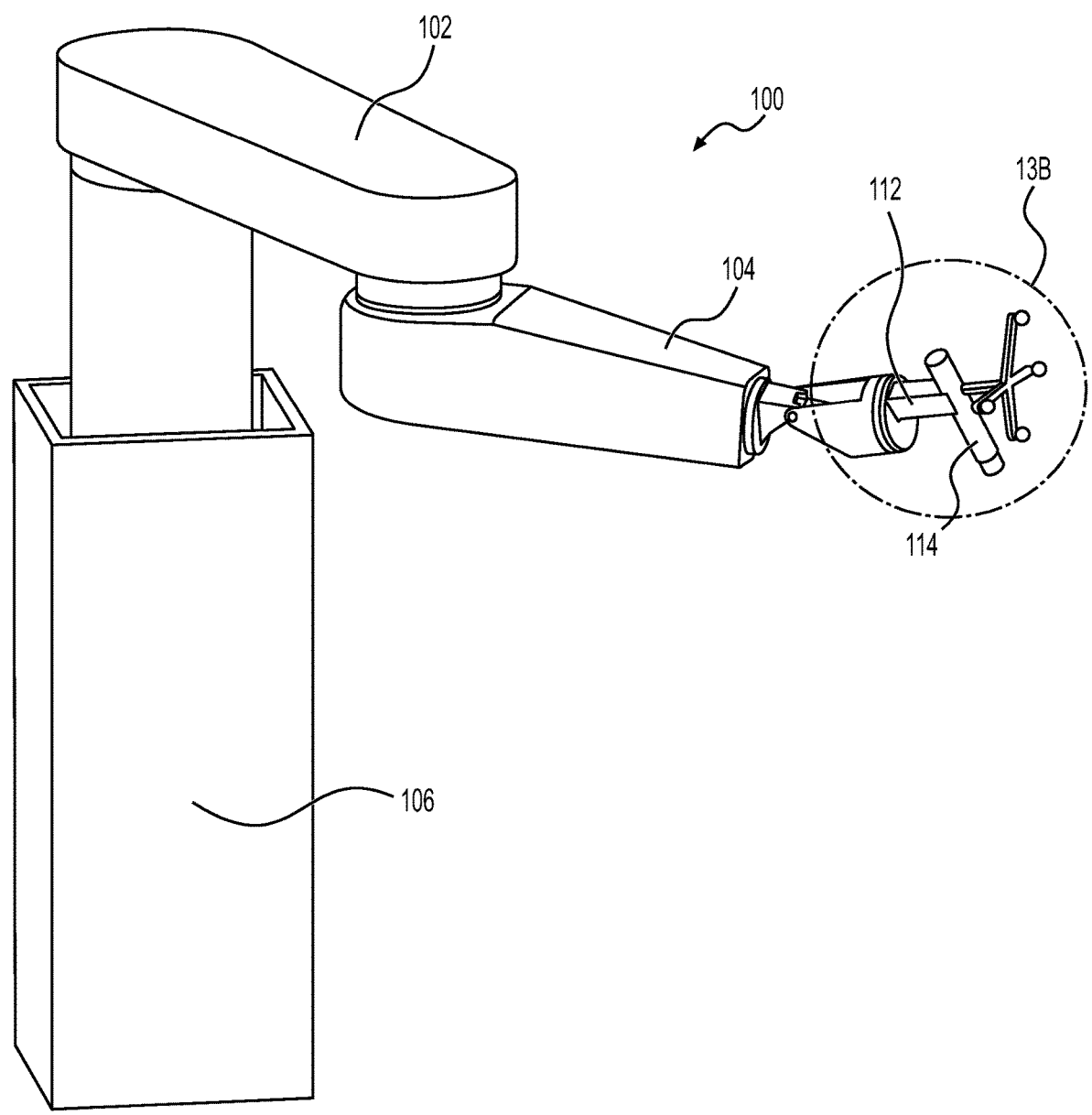
Figure 13B:
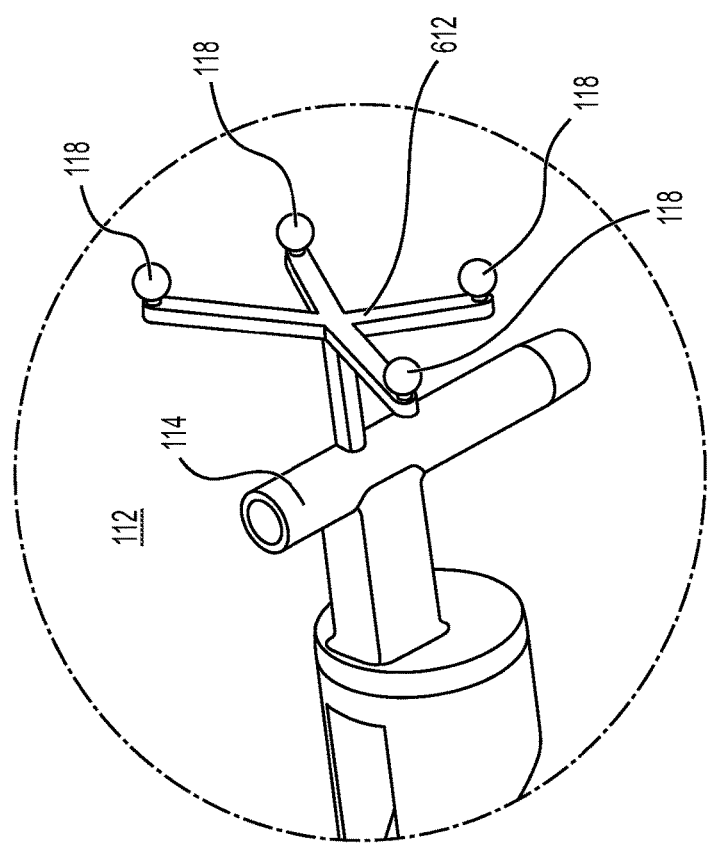
Figure 13C:
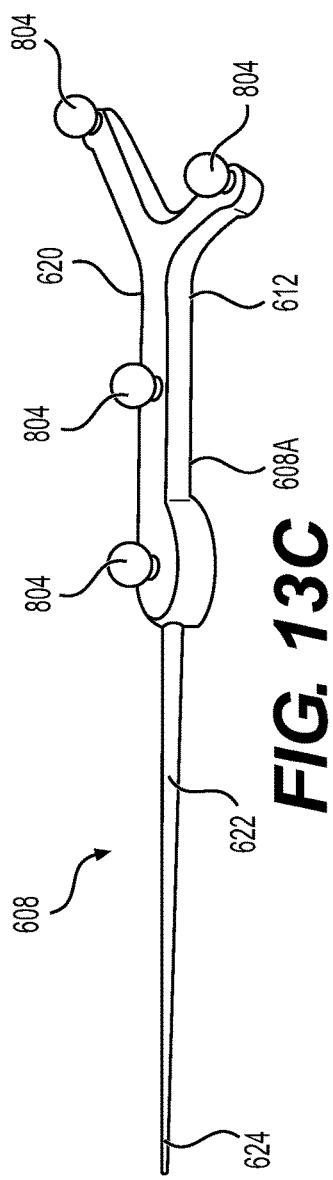
Figures 14A, 14B:
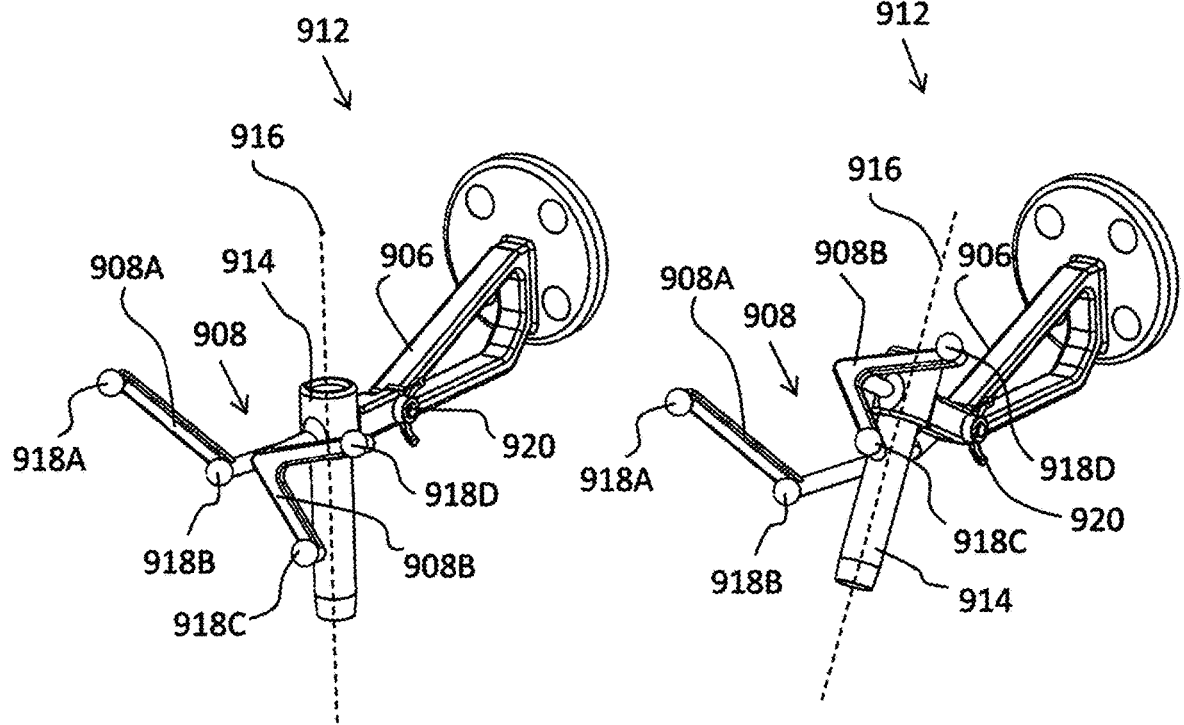
Figure 14C:
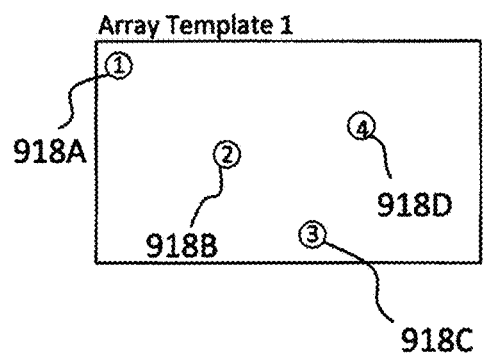
Figure 14D:
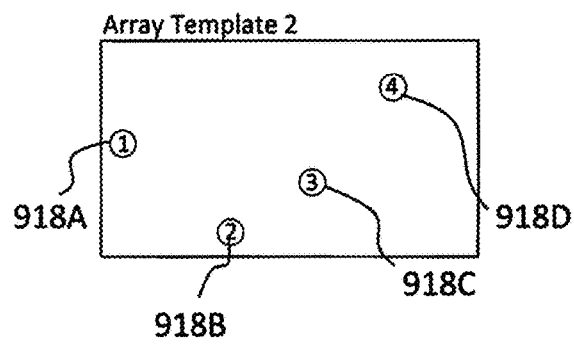
Figure 15A:
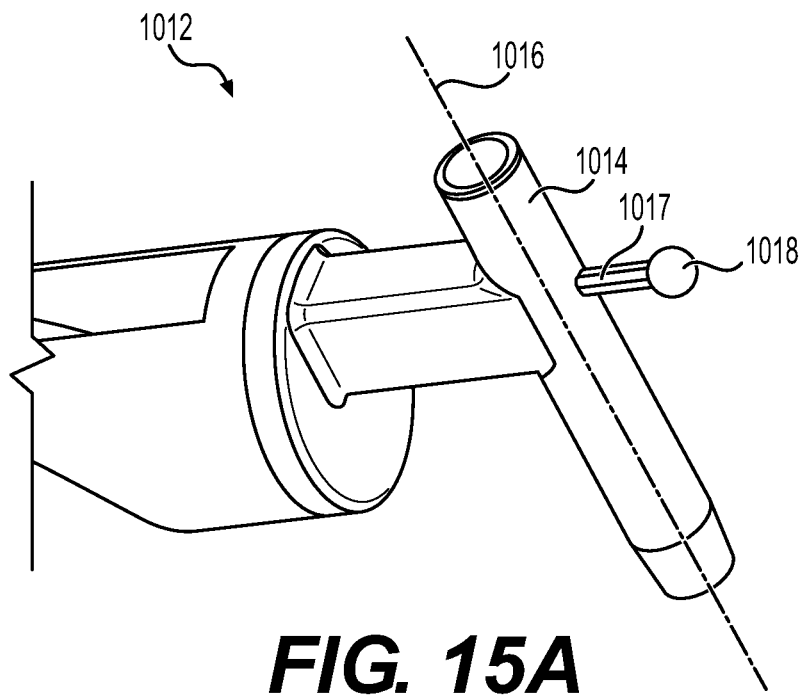
Figure 15B:
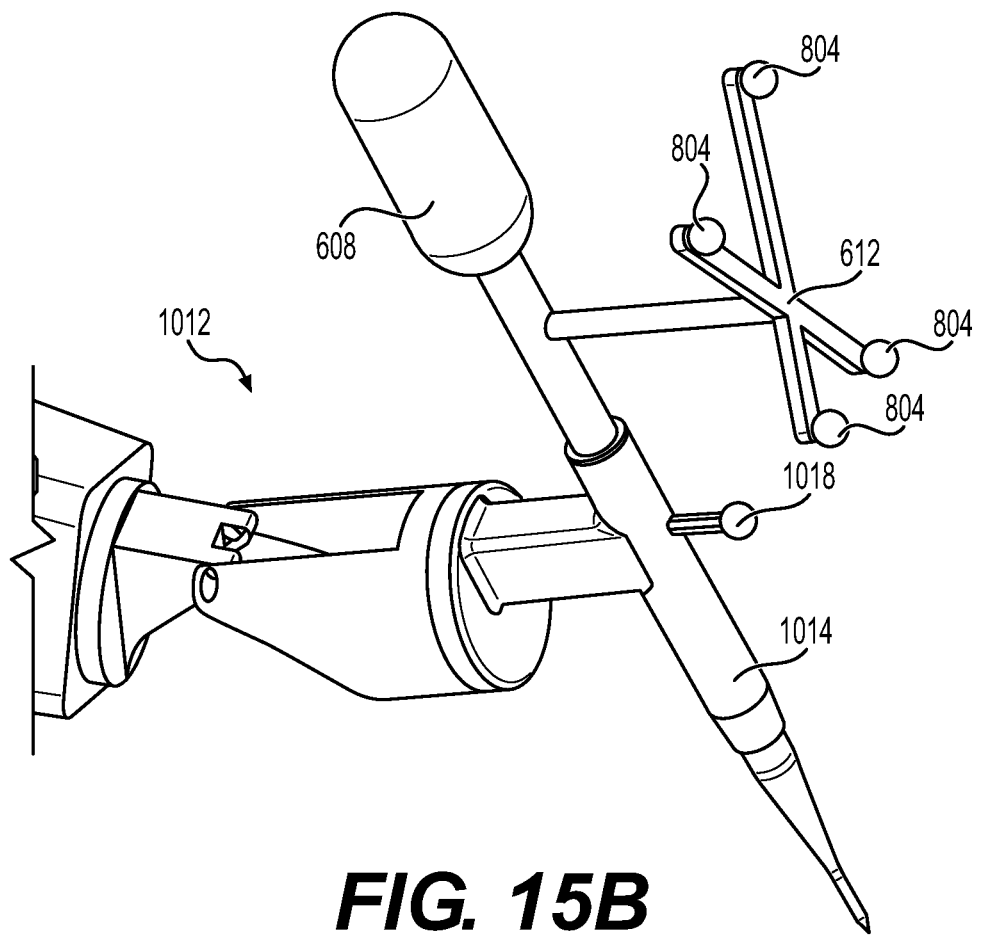
Figure 15D:
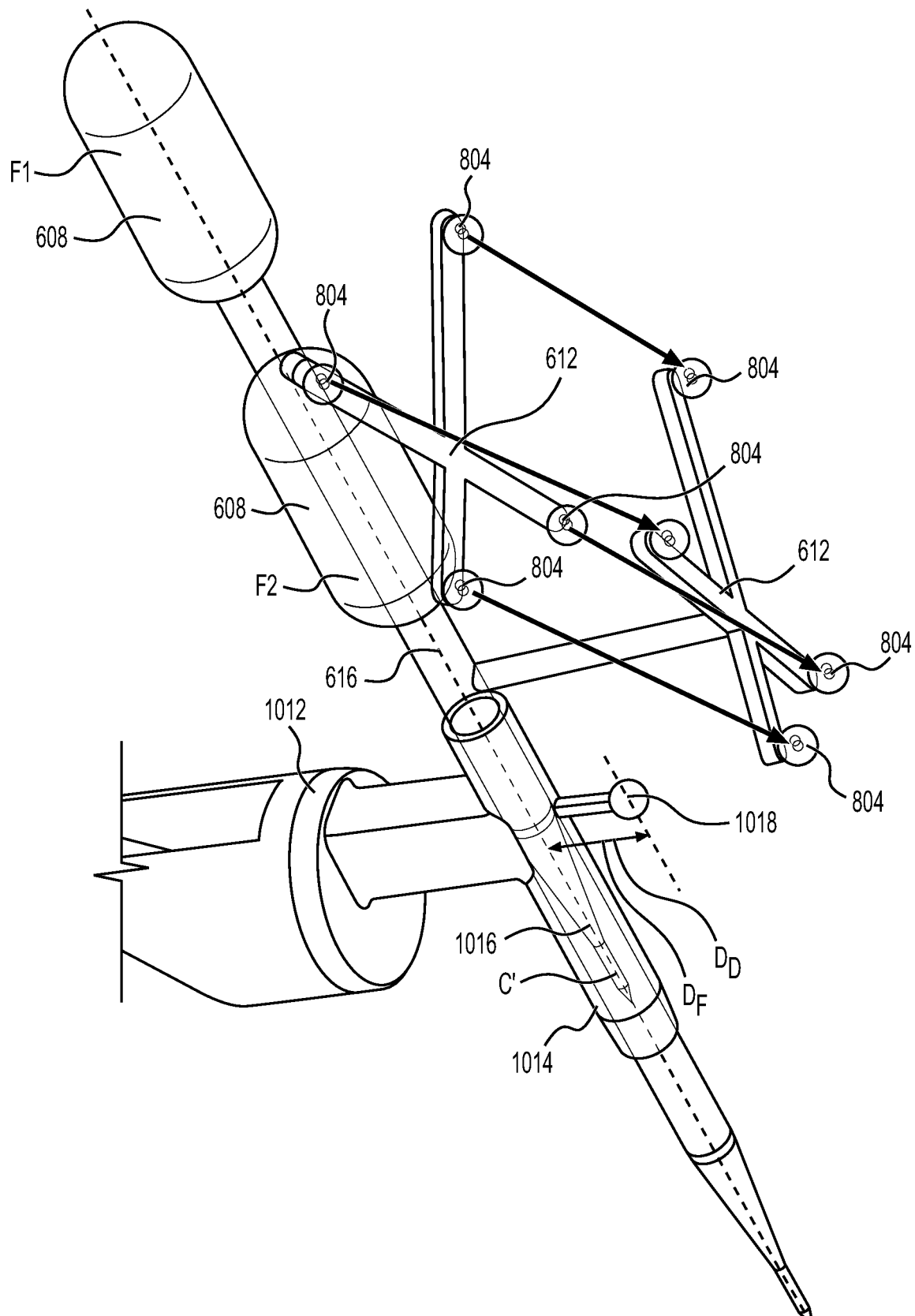
Figure 15E:
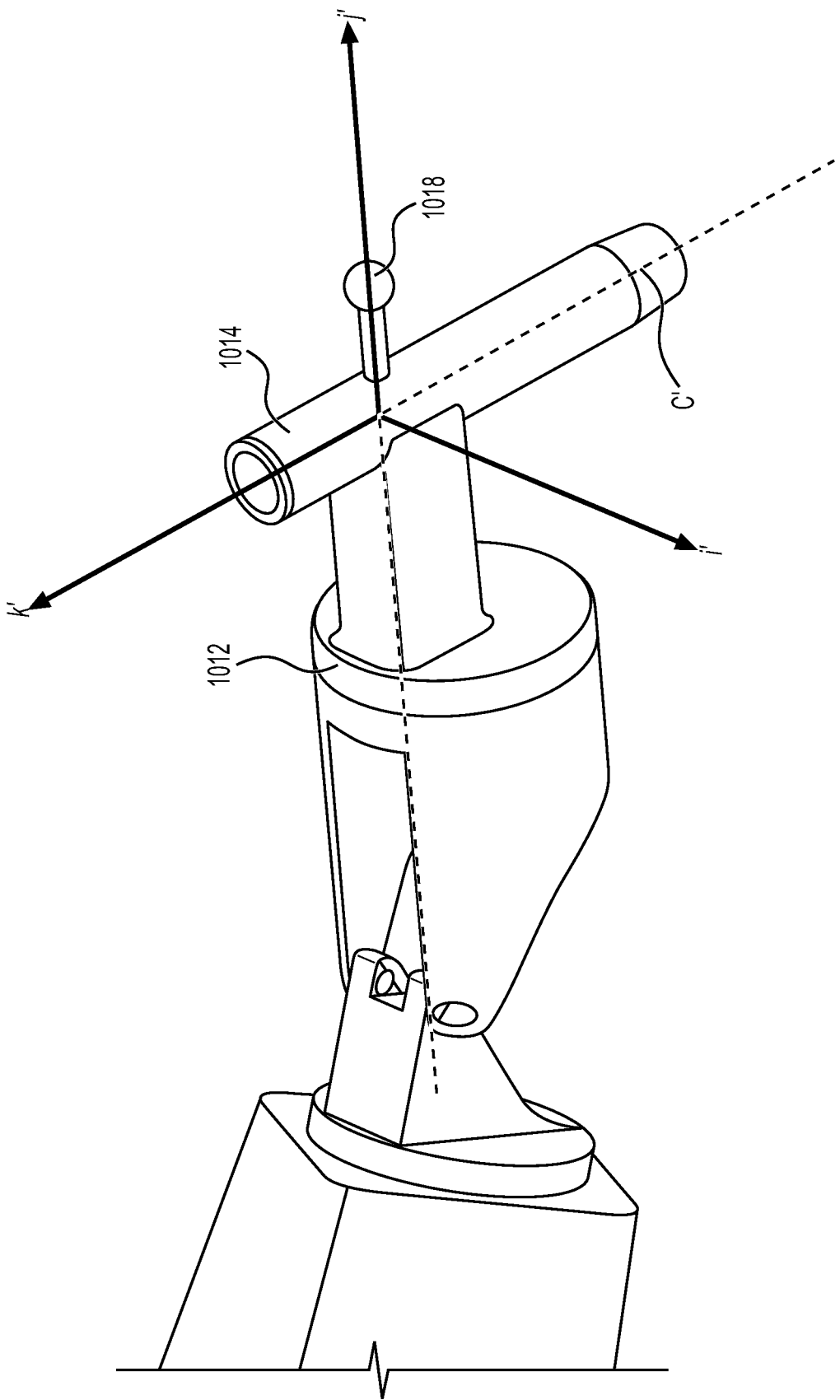
Figure 16:
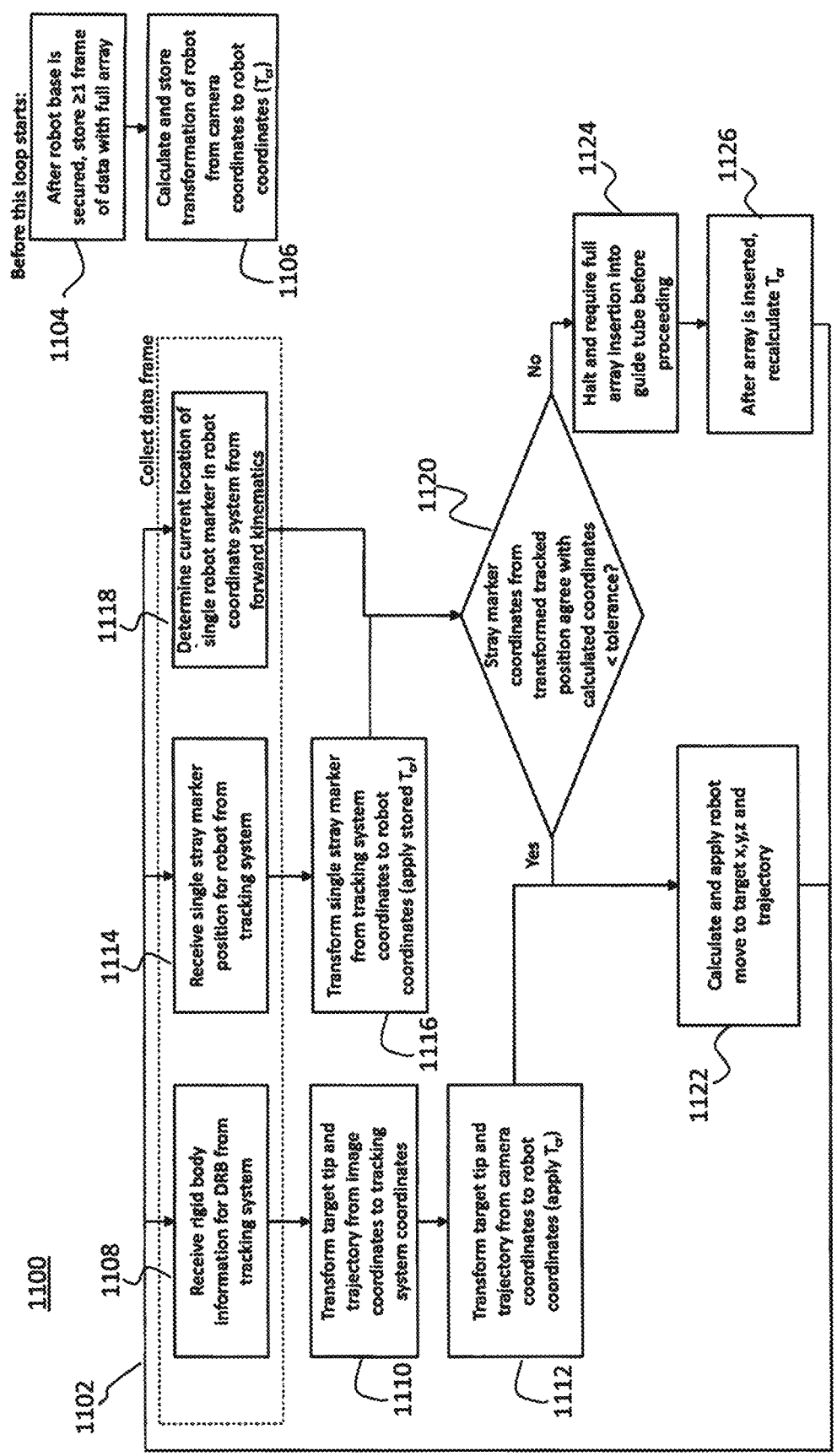
Figure 17A:
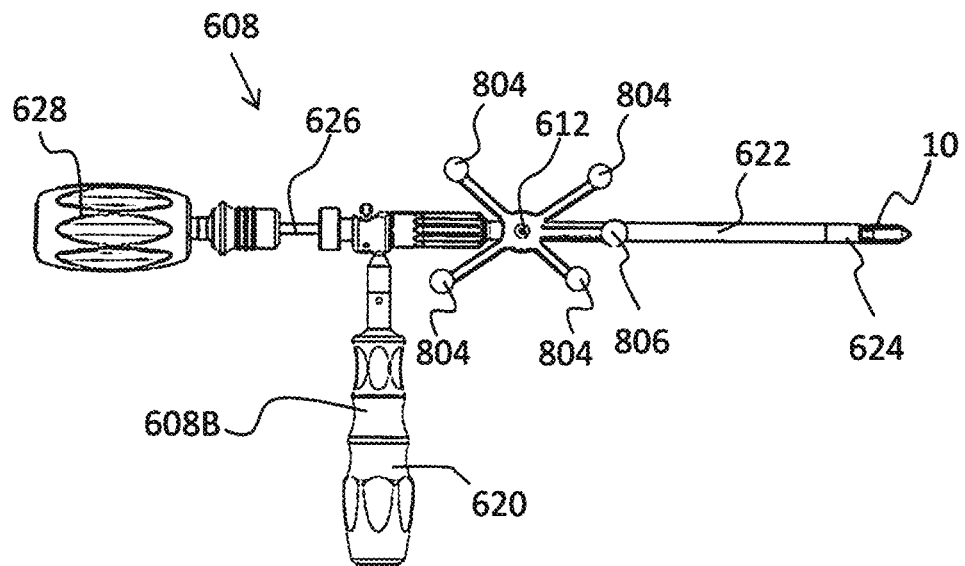
Figure 17B:
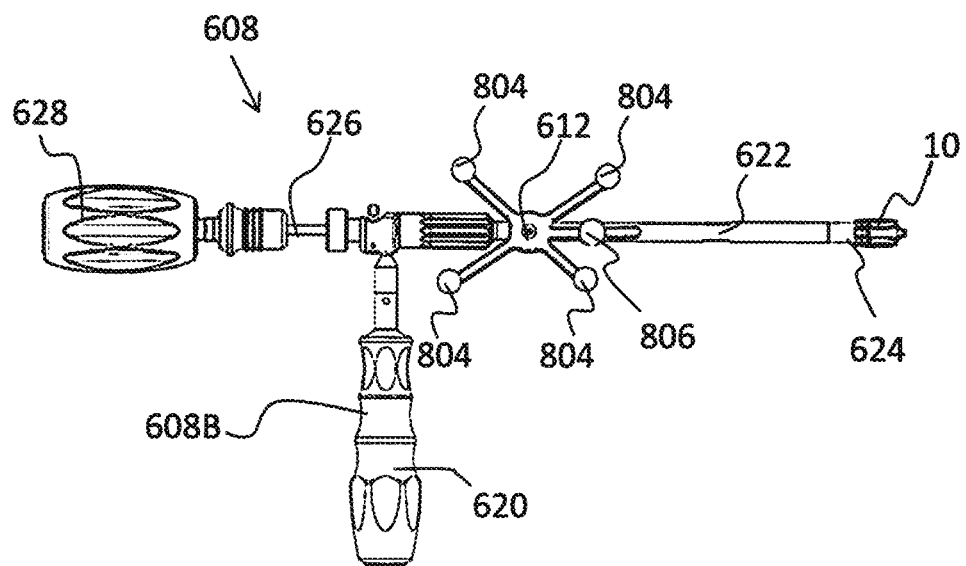
Figure 18A:
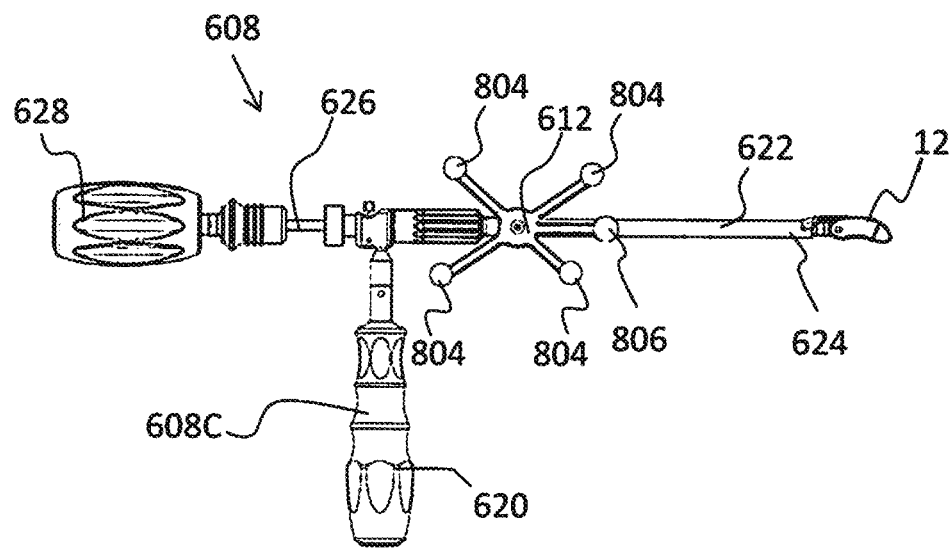
Figure 18B:
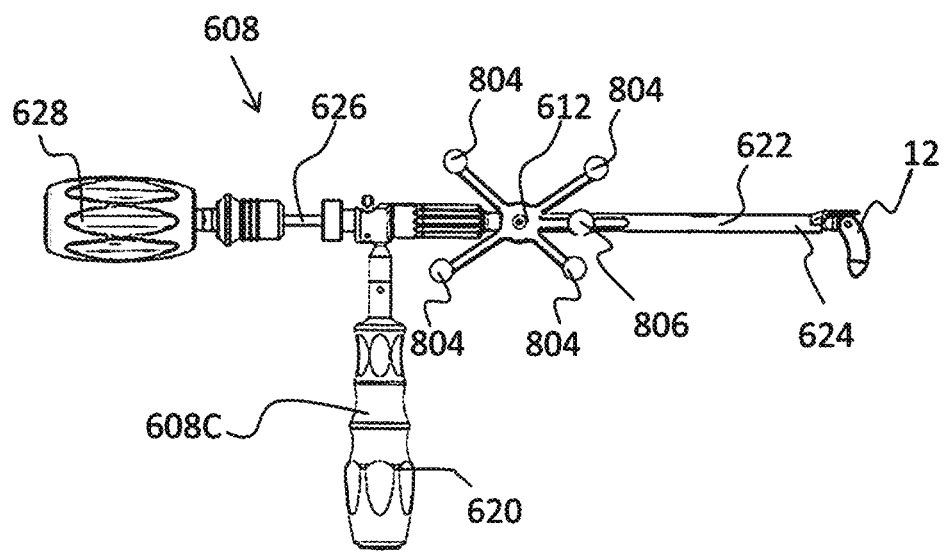
Figure 19A:
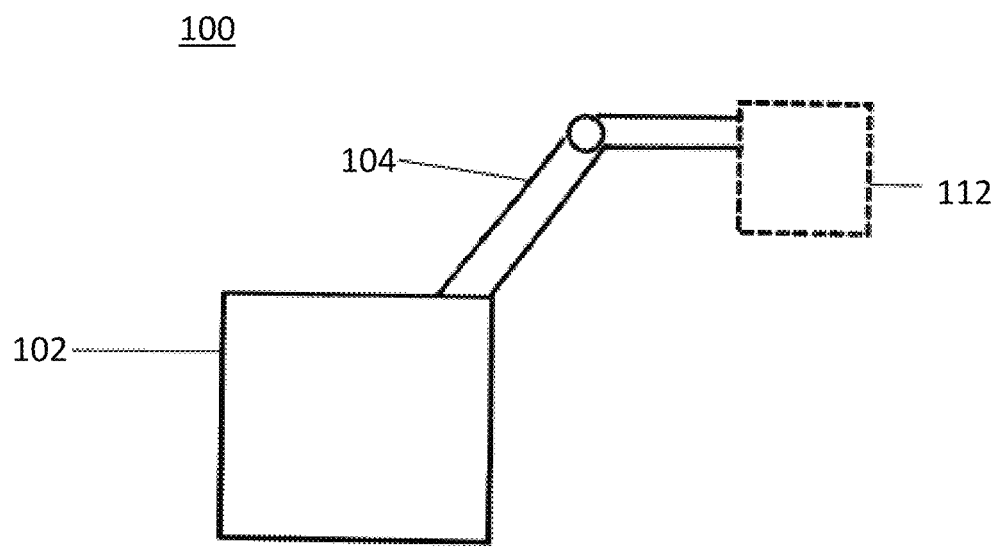
Figure 19B:
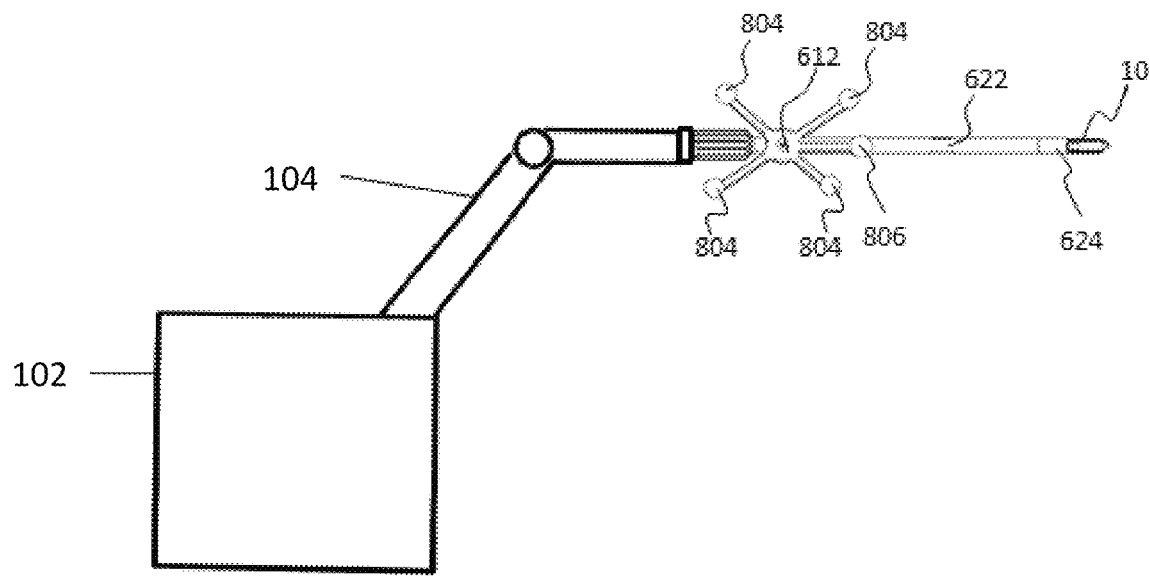
Figure 20:
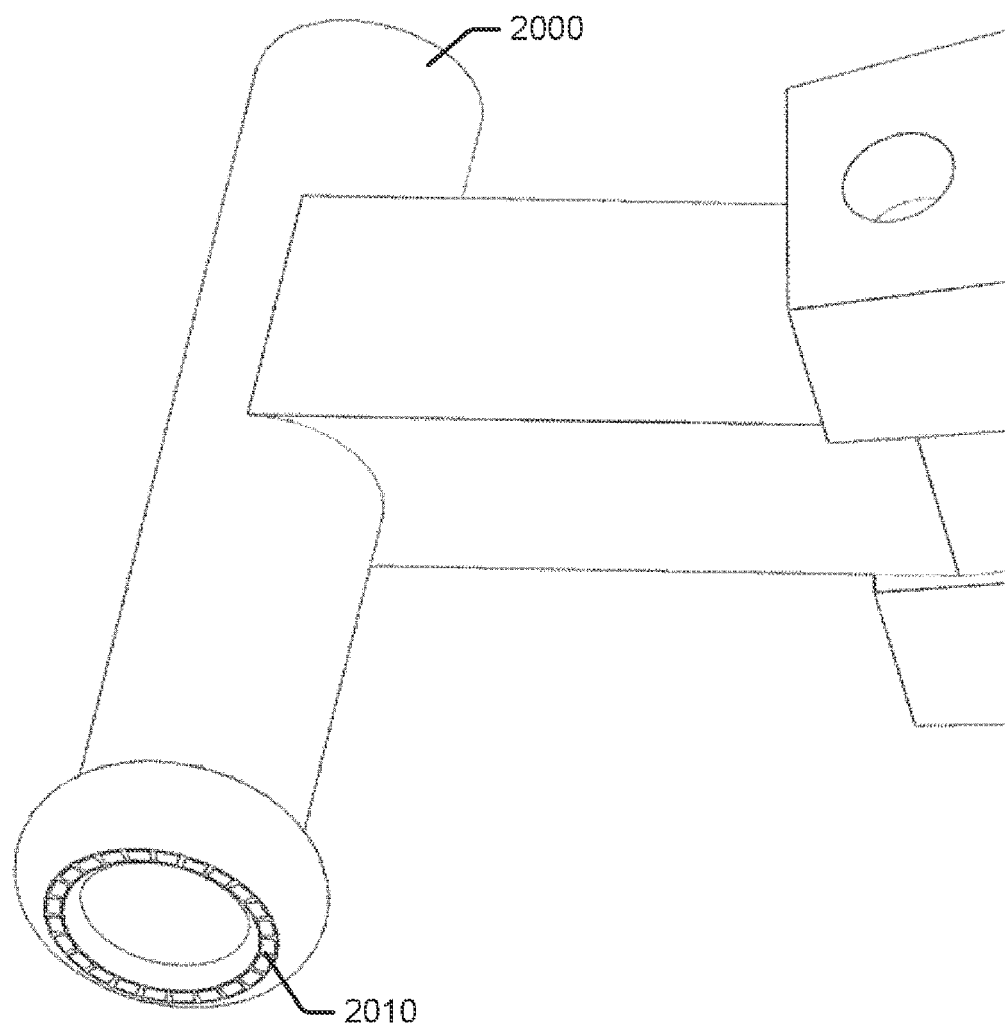
Figure 21A:
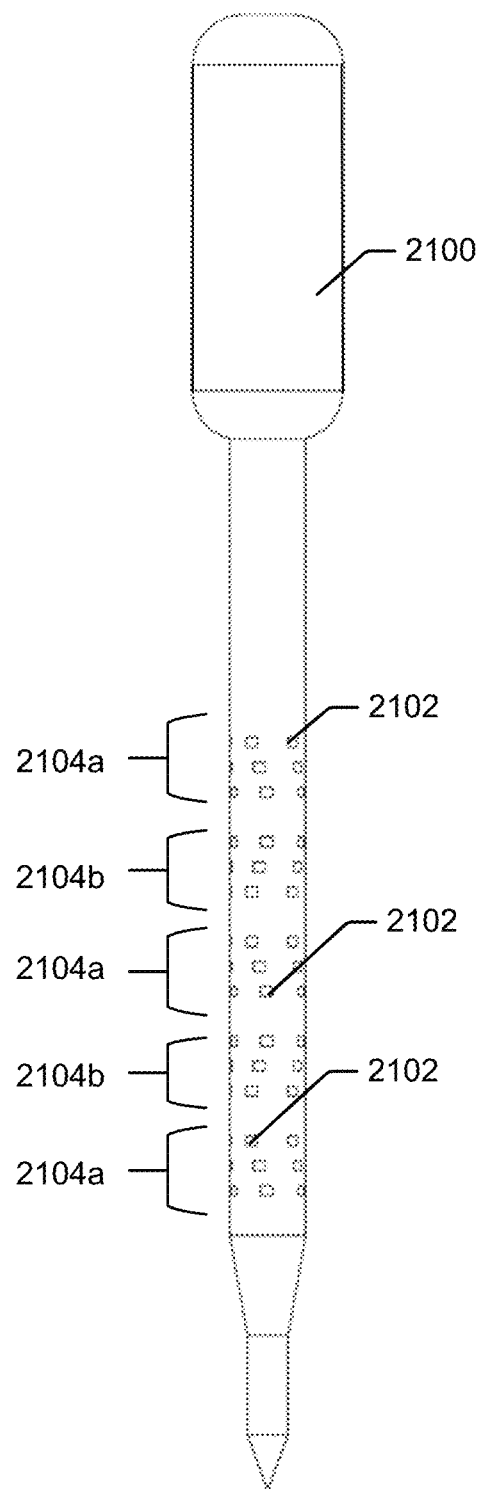
Figure 21B:
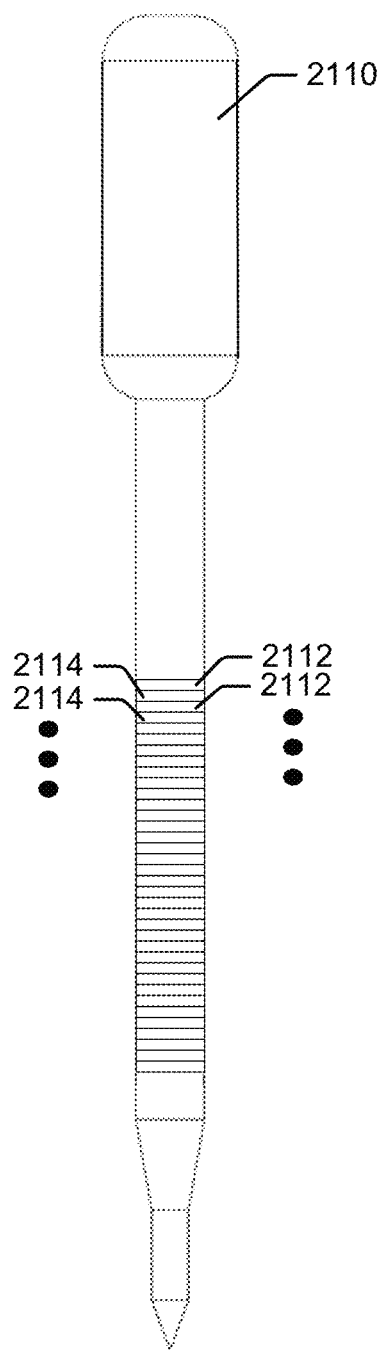
Figure 21C:
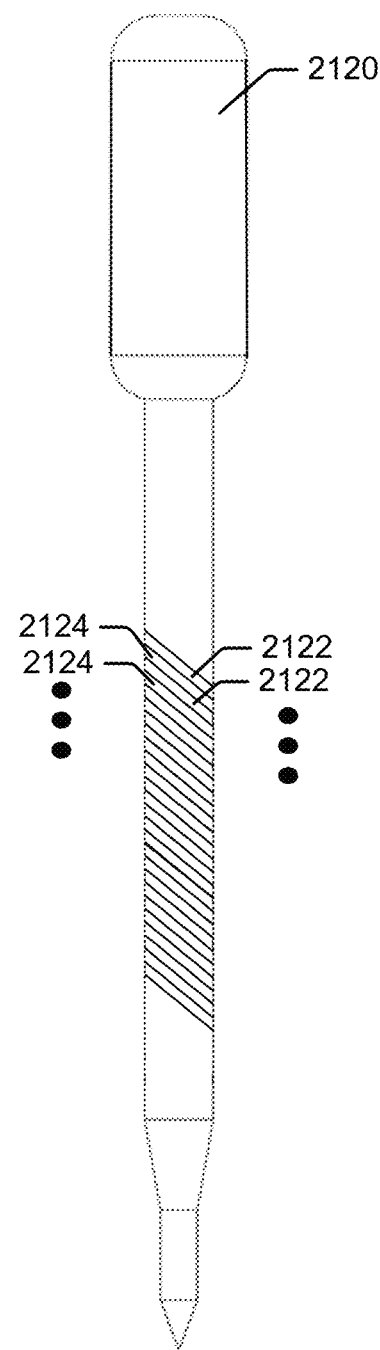
Figure 22:
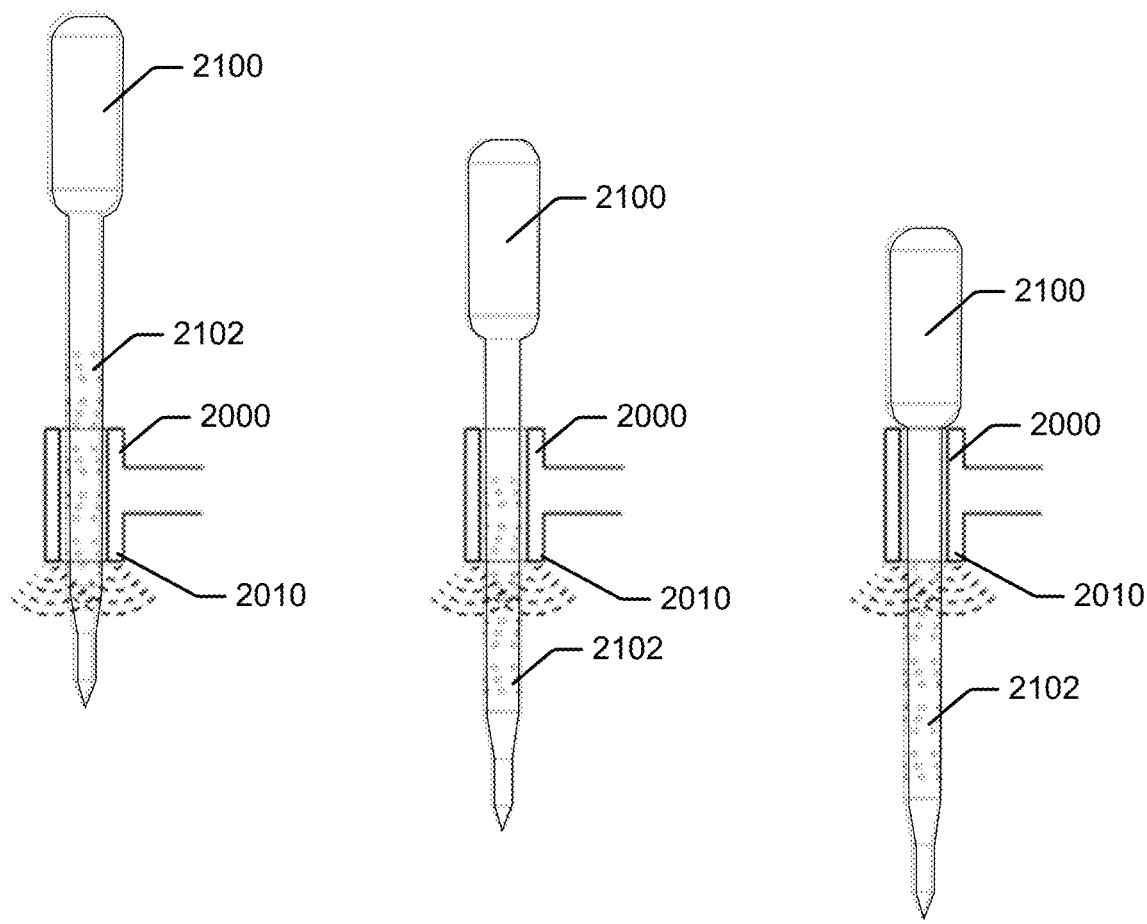
Figure 23:
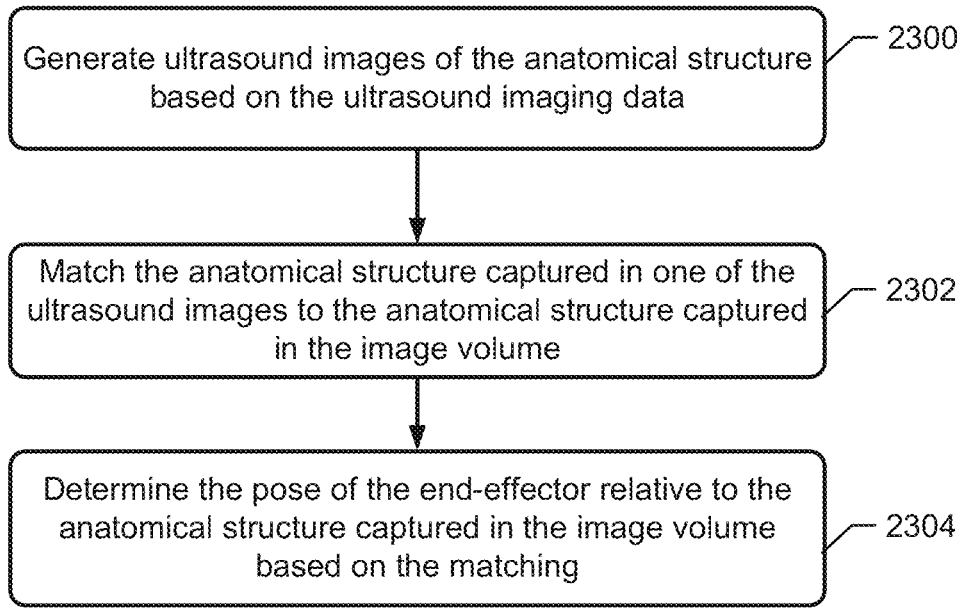
Figure 24:
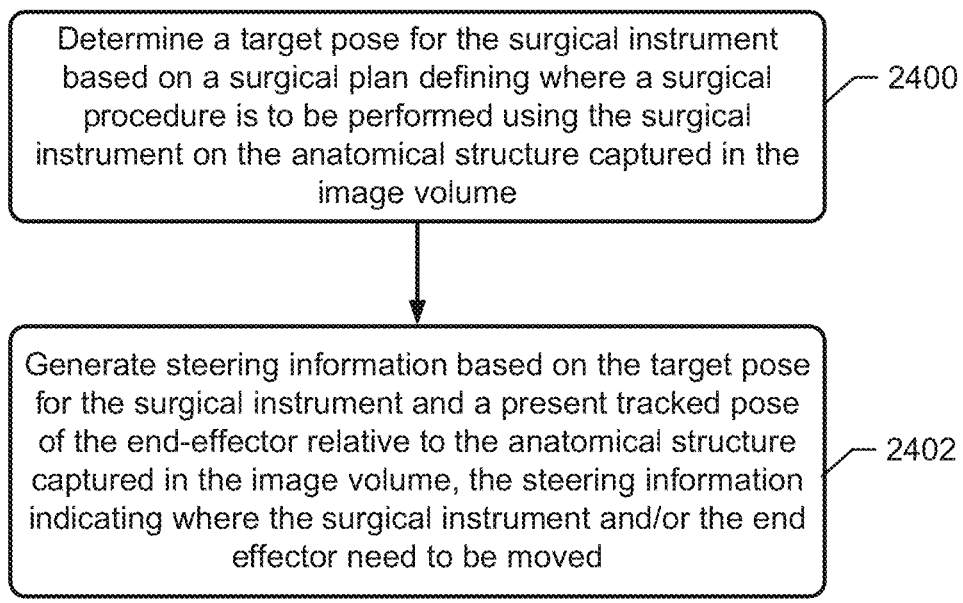
Figure 25:
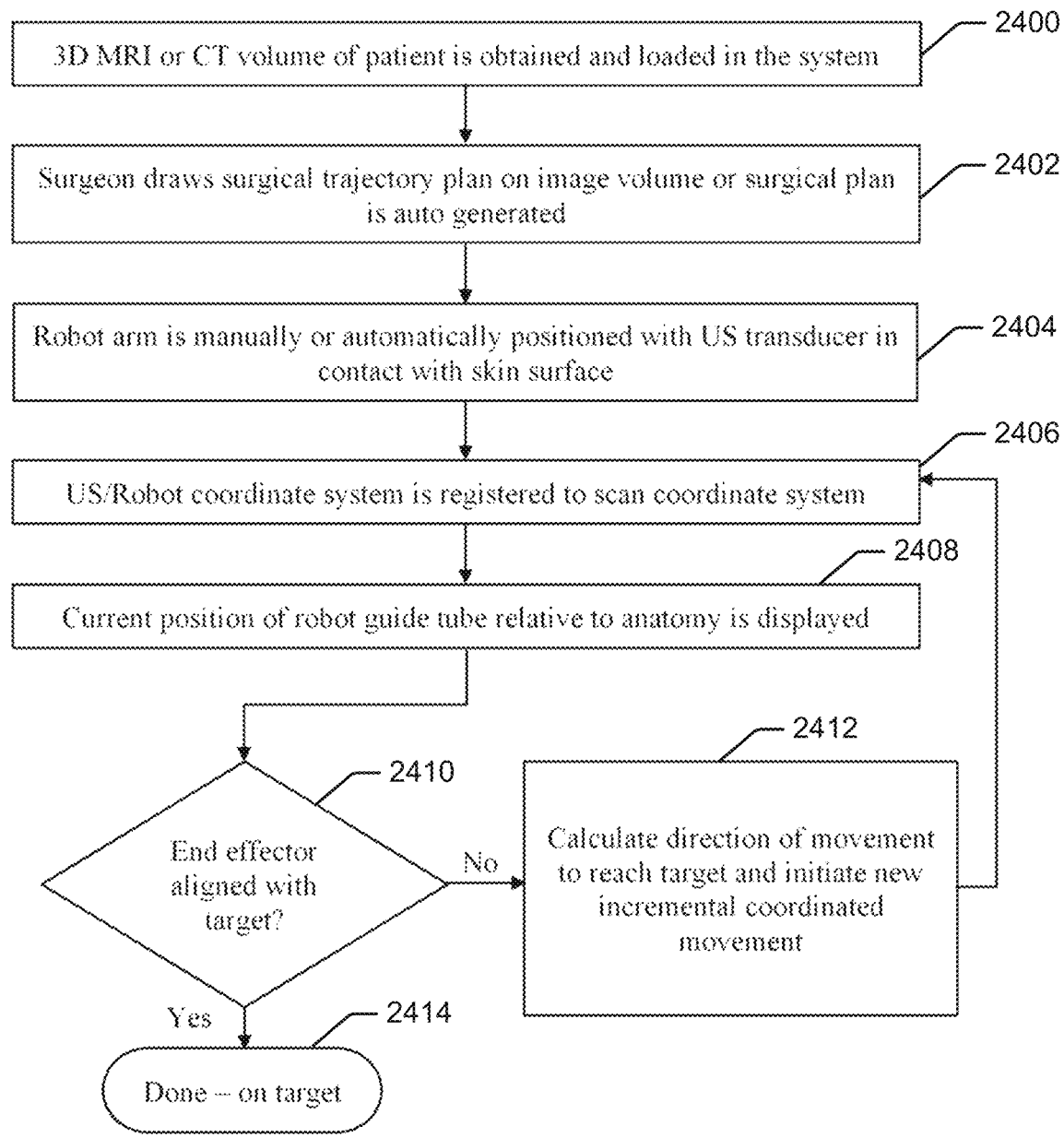
Figure 26A:
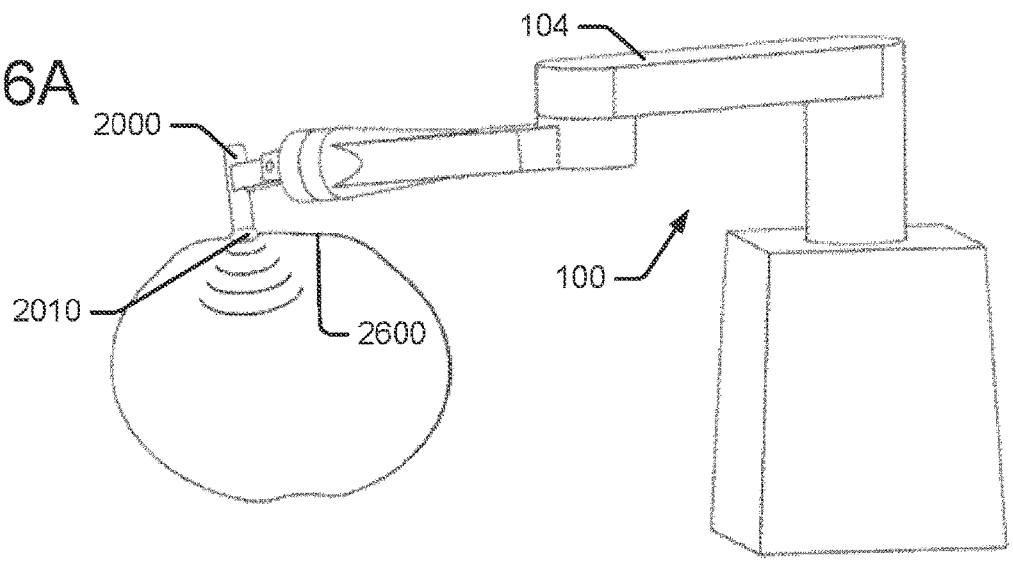
Figure 26B:
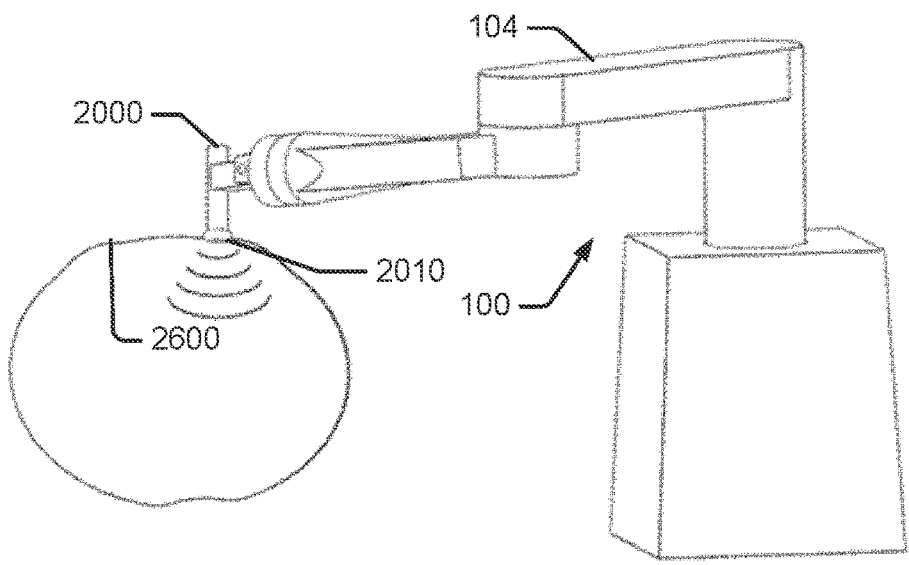
Figure 26C:
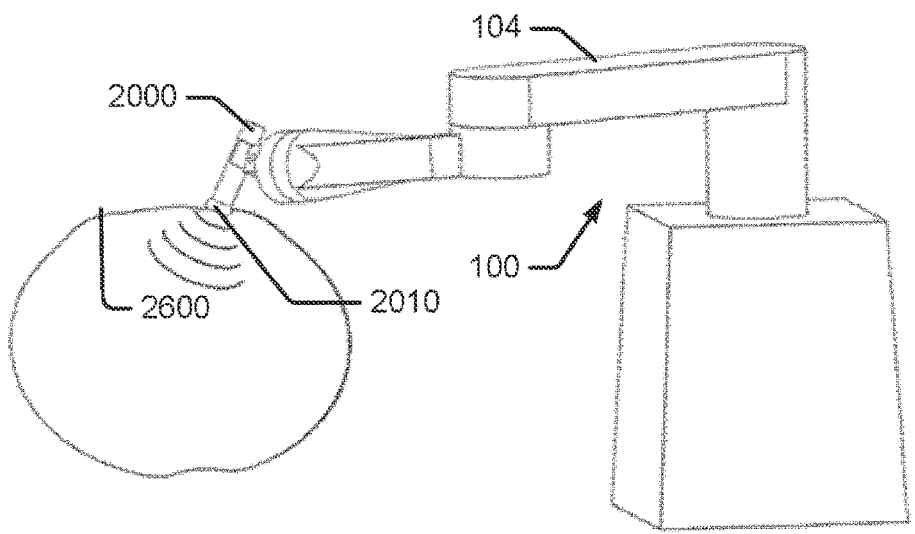
Figure 27:
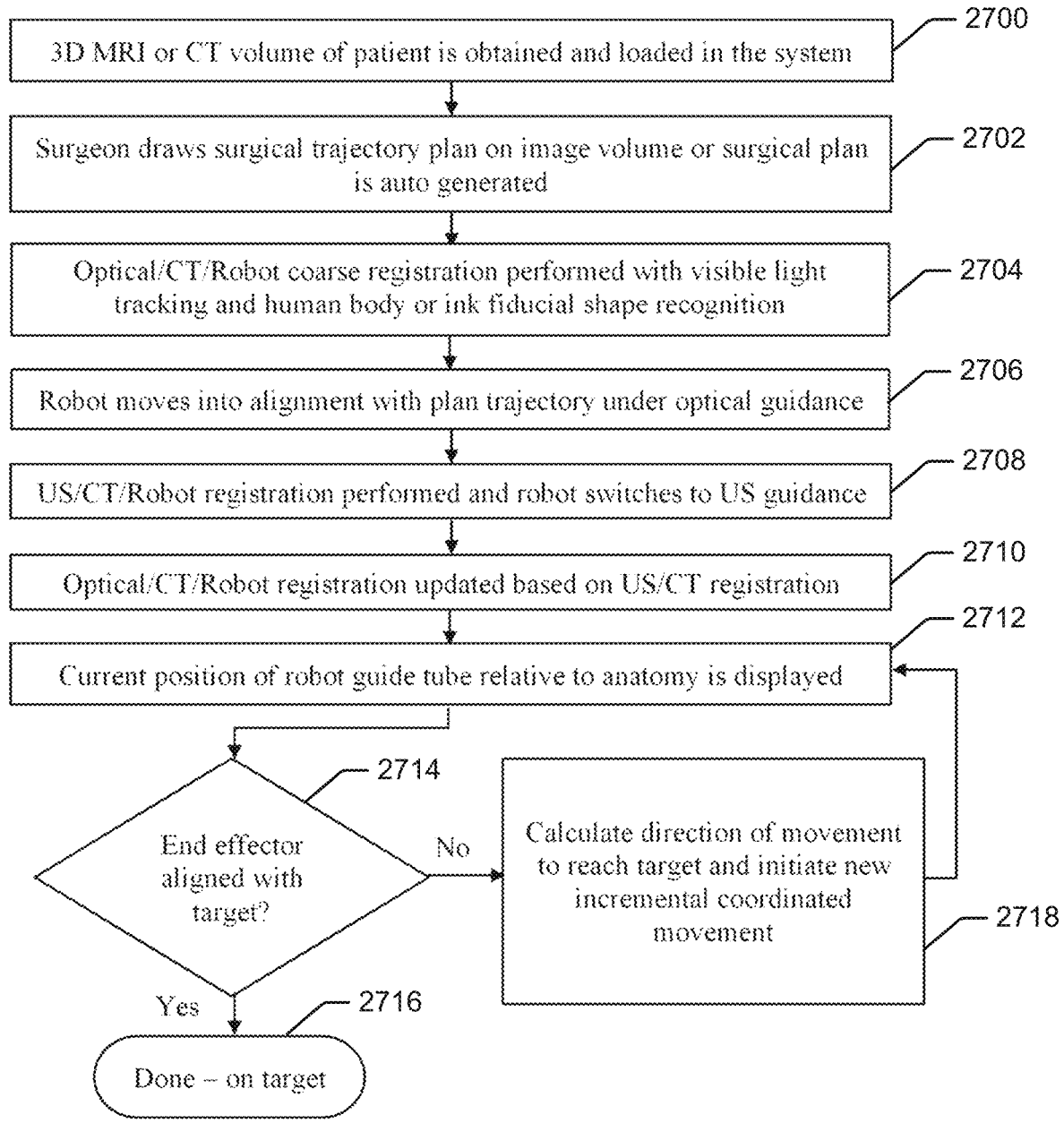
Figure 28:
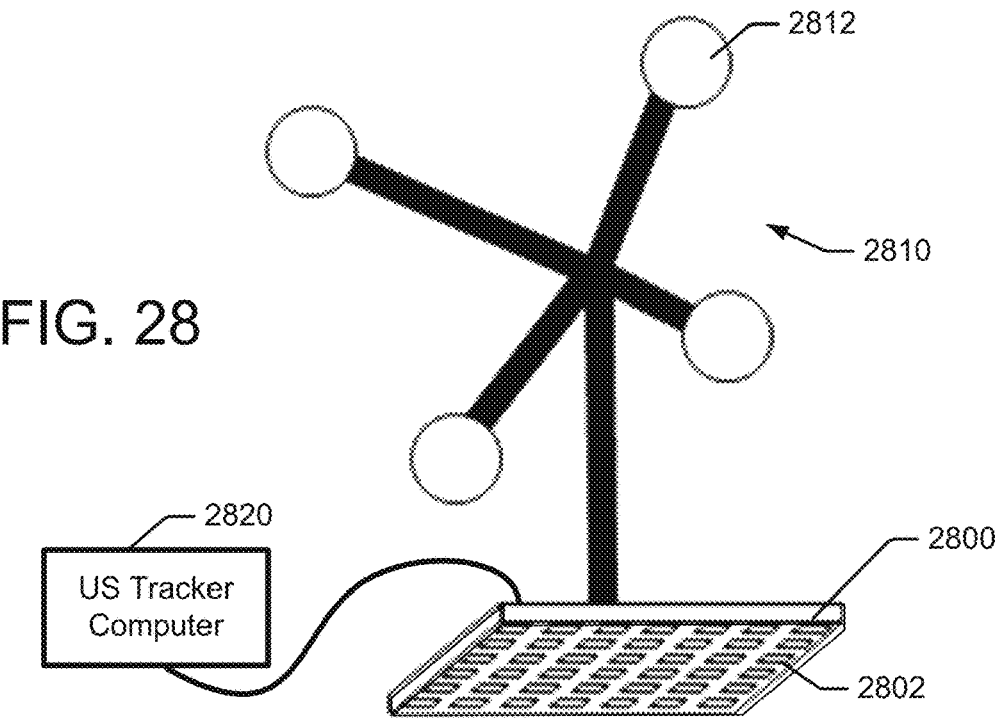
Figure 29:
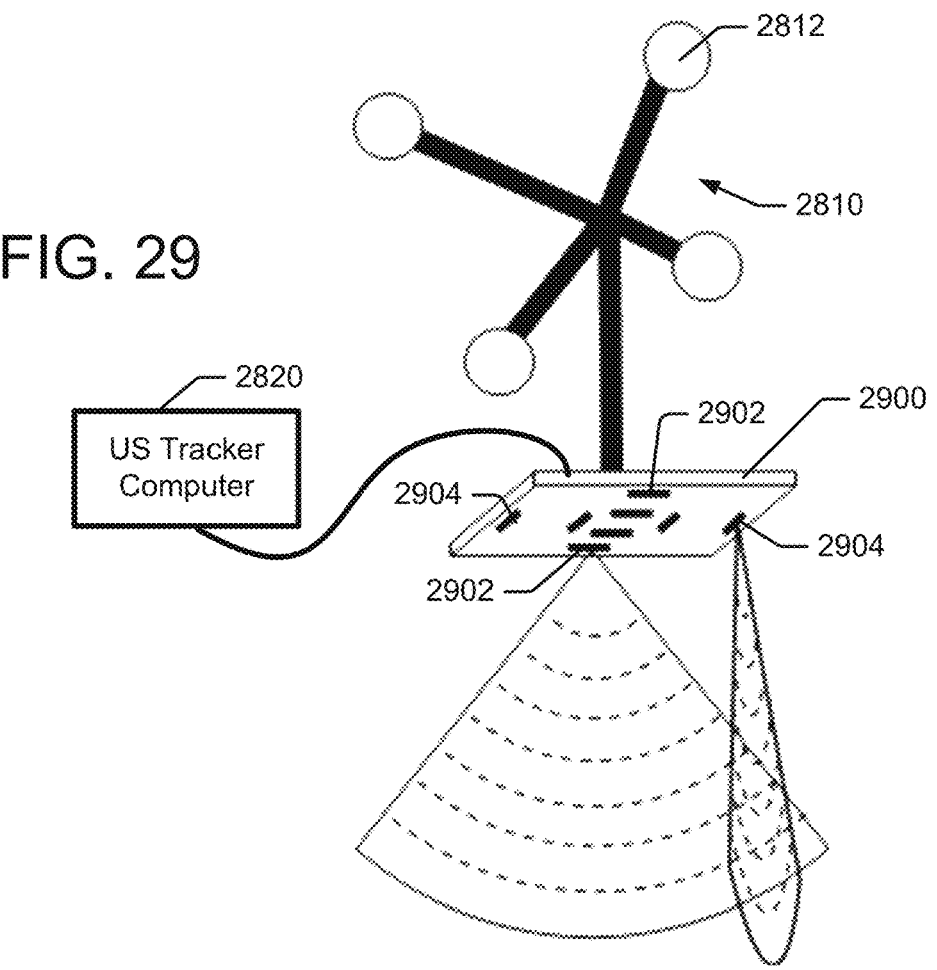

F. 4 illustrates a portion of a surgical robot in accordance with an example embodiment;

FIG. 5 illustrates a block diagram of a surgical robot in accordance with an example embodiment;

FIG. 6 illustrates a surgical robot in accordance with an example embodiment;

FIGS. 7A-7C illustrate an end-effector in accordance with an example embodiment;

FIG. 8 illustrates a surgical instrument and the end-effector, before and after, inserting the surgical instrument into the guide tube of the end-effector according to one embodiment;

FIGS. 9A-9C illustrate portions of an end-effector and robot arm in accordance with an example embodiment;

FIG. 10 illustrates a dynamic reference array, an imaging array, and other components in accordance with an example embodiment;

FIG. 11 illustrates operations for registration in accordance with an example embodiment;

FIG. 12A-12B illustrate embodiments of imaging devices according to example embodiments;

FIG. 13A illustrates a portion of a robot including the robot arm and an end-effector in accordance with an example embodiment;

FIG. 13B is a close-up view of the end-effector, with a plurality of tracking markers rigidly affixed thereon, shown in FIG. 13A;

FIG. 13C is an instrument or instrument with a plurality of tracking markers rigidly affixed thereon according to one embodiment;

FIG. 14A is an alternative version of an end-effector with moveable tracking markers in a first configuration;

FIG. 14B is the end-effector shown in FIG. 14A with the moveable tracking markers in a second configuration;

FIG. 14C shows the template of tracking markers in the first configuration from FIG. 14A;

FIG. 14D shows the template of tracking markers in the second configuration from FIG. 14B;

FIG. 15A shows an alternative version of the end-effector having only a single tracking marker affixed thereto;

FIG. 15B shows the end-effector of FIG. 15A with an instrument disposed through the guide tube;

FIG. 15C shows the end-effector of FIG. 15A with the instrument in two different positions, and the resulting logic to determine if the instrument is positioned within the guide tube or outside of the guide tube;

FIG. 15D shows the end-effector of FIG. 15A with the instrument in the guide tube at two different frames and its relative distance to the single tracking marker on the guide tube;

FIG. 15E shows the end-effector of FIG. 15A relative to a coordinate system;

FIG. 16 is a block diagram of operations for navigating and moving the end-effector of the robot to a desired target trajectory;

FIGS. 17A-17B depict an instrument for inserting an expandable implant having fixed and moveable tracking markers in contracted and expanded positions, respectively;

FIGS. 18A-18B depict an instrument for inserting an articulating implant having fixed and moveable tracking markers in insertion and angled positions, respectively;

FIG. 19A depicts an embodiment of a robot with interchangeable or alternative end-effectors;

FIG. 19B depicts an embodiment of a robot with an instrument style end-effector coupled thereto;

FIG. 20 depicts a guide tube configured to guide movement of a surgical instrument through the guide tube, and an ultrasound (US) transducer unit formed by an array of US transducers spaced apart along a leading edge of the guide tube, in accordance with some embodiments;

FIGS. 21A-21C depict differently configured surgical instruments which have shafts configured to be tracked relative to the guide tube using the US transducer;

FIG. 22 depicts the surgical instrument of FIG. 21A at three different depths and rotations relative to the guide tube, in accordance with some embodiments;

FIG. 23 depicts a flowchart of operations that can be performed by at least one processor to track pose of the end-effector relative to anatomical structure captured in an image volume based on US imaging data from a US transducer, in accordance with some embodiments;

FIG. 24 depicts a flowchart of operations that can be performed by at least one processor to generate steering information based on a present pose of an end-effector determined from US imaging data, in accordance with some embodiments;

FIG. 25 depicts a more detailed flowchart of operations and be performed by at least one processor to generate navigation information that can be used to guide movement of the robot end-effector toward a target pose, in accordance with some embodiments;

FIGS. 26A-C depicts a sequence of snapshots of a robotic arm of the surgical robot system moving laterally to a target pose while automatically maintaining contact between the US transducer and the patient's skin and normal to the body surface, in accordance with some embodiments;

FIG. 27 depicts a flowchart of operations for controlling movement of the robot arm to a target pose using a combination of optical feedback control and US transducer feedback control, in accordance with some embodiments;

FIG. 28 depicts an anatomical structure tracker apparatus that is configured in accordance with some embodiments;

FIG. 29 depicts another anatomical structure tracker apparatus that is configured in accordance with some other embodiments; and FIGS. 30-38 depict various US transducer apparatuses which are configured in accordance with some embodiments.

DETAILED DESCRIPTION

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Figure 1:
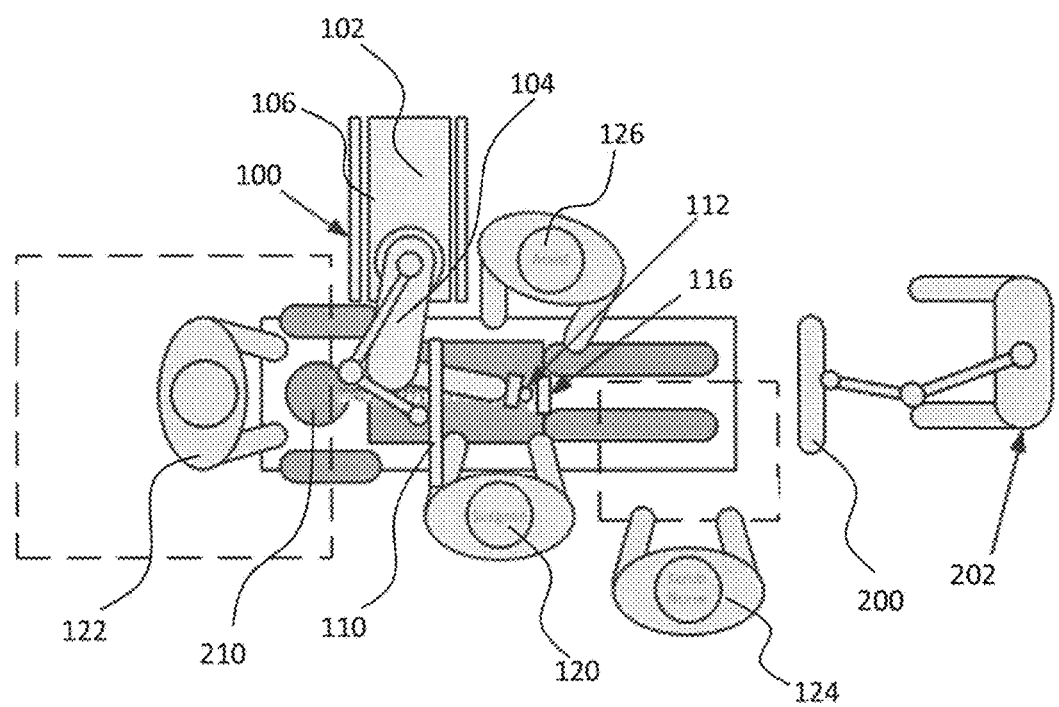
FIG. 1 is an overhead view of a potential arrangement for locations of the robotic system, patient, surgeon, and other medical personnel during a surgical procedure.
Figure 2:
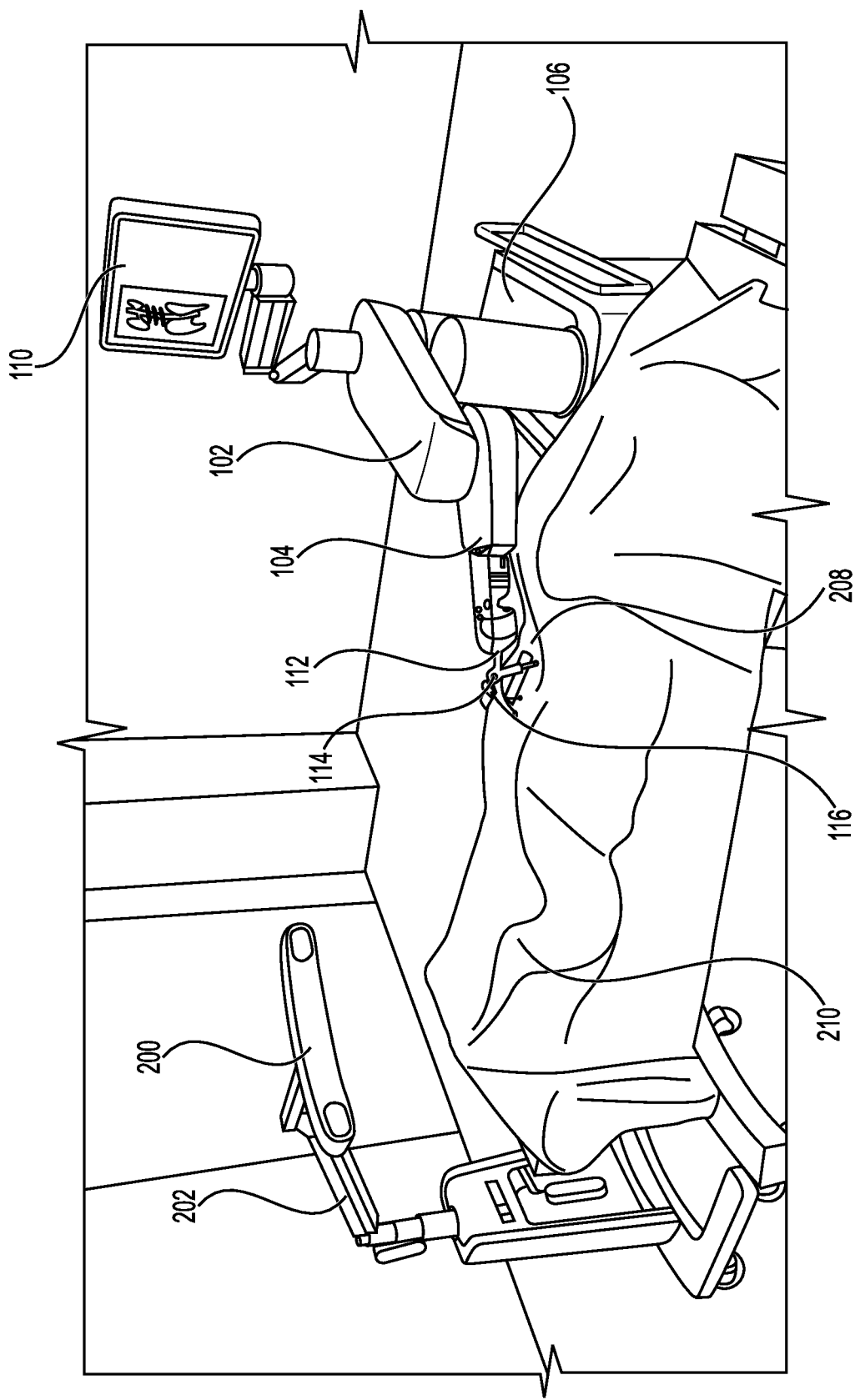
FIG. 2 illustrates the robotic system including positioning of the surgical robot and the camera relative to the patient according to one embodiment.

Turning now to the drawing, FIGS. 1 and 2 illustrate a surgical robot system 100 in accordance with an example embodiment. Surgical robot system 100 may include, for example, a surgical robot 102, one or more robot arms 104, a base 106, a display 110, an end-effector 112, for example, including a guide tube 114, and one or more tracking markers 118. The surgical robot system 100 may include a patient tracking device 116 also including one or more tracking markers 118, which is adapted to be secured directly to the patient 210 (e.g., to the bone of the patient 210). The surgical robot system 100 may also utilize a camera 200, for example, positioned on a camera stand 202. The camera stand 202 can have any suitable configuration to move, orient, and support the camera 200 in a desired position. The camera 200 may include any suitable camera or cameras, such as one or more infrared cameras (e.g., bifocal or stereophotogrammetric cameras), able to identify, for example, active and passive tracking markers 118 in a given measurement volume viewable from the perspective of the camera 200. The camera 200 may scan the given measurement volume and detect the light that comes from the markers 118 in order to identify and determine the position of the markers 118 in three-dimensions. For example, active markers 118 may include infrared-emitting markers that are activated by an electrical signal (e.g., infrared light emitting diodes (LEDs)), and passive markers 118 may include retro-reflective markers that reflect infrared light (e.g., they reflect incoming IR radiation into the direction of the incoming light), for example, emitted by illuminators on the camera 200 or other suitable device.

FIGS. 1 and 2 illustrate a potential configuration for the placement of the surgical robot system 100 in an operating room environment. For example, the robot 102 may be positioned near or next to patient 210. Although depicted near the head of the patient 210, it will be appreciated that the robot 102 can be positioned at any suitable location near the patient 210 depending on the area of the patient 210 undergoing the operation. The camera 200 may be separated from the robot system 100 and positioned at the foot of patient 210. This location allows the camera 200 to have a direct visual line of sight to the surgical field 208. Again, it is contemplated that the camera 200 may be located at any suitable position having line of sight to the surgical field 208. In the configuration shown, the surgeon 120 may be positioned across from the robot 102, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. The traditional areas for the anesthesiologist 122 and the nurse or scrub tech 124 remain unimpeded by the locations of the robot 102 and camera 200.

With respect to the other components of the robot 102, the display 110 can be attached to the surgical robot 102 and in other example embodiments, display 110 can be detached from surgical robot 102, either within a surgical room with the surgical robot 102, or in a remote location. End-effector 112 may be coupled to the robot arm 104 and controlled by at least one motor. In example embodiments, end-effector 112 can comprise a guide tube 114, which is able to receive and orient a surgical instrument 608 (described further herein) used to perform surgery on the patient 210.

As used herein, the term "end-effector" is used interchangeably with the terms "end-effectuator" and "effectuator element." The term "instrument" is used in a non-limiting manner and can be used interchangeably with "tool" to generally refer to any type of device that can be used during a surgical procedure in accordance with embodiments disclosed herein. Example instruments include, without limitation, drills, screwdriver s, saws, dilators, retractors, implant inserters, and implants such as a screws, spacers, interbody fusion devices, plates, rods, etc. Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument 608 in a desired manner.

The surgical robot 102 is able to control the translation and orientation of the end-effector 112. The robot 102 is able to move end-effector 112 along x-, y-, and z-axes, for example. The end-effector 112 can be configured for selective rotation about one or more of the x-, y-, and z-axis, and a Z Frame axis (such that one or more of the Euler Angles (e.g., roll, pitch, and/or yaw) associated with end-effector 112 can be selectively controlled). In some example embodiments, selective control of the translation and orientation of end-effector 112 can permit performance of medical procedures with significantly improved accuracy compared to conventional robots that utilize, for example, a six degree of freedom robot arm comprising only rotational axes. For example, the surgical robot system 100 may be used to operate on patient 210, and robot arm 104 can be positioned above the body of patient 210, with end-effector 112 selectively angled relative to the z-axis toward the body of patient 210.

In some example embodiments, the pose of the surgical instrument 608 can be dynamically updated so that surgical robot 102 can be aware of the pose of the surgical instrument 608 at all times during the procedure. Consequently, in some example embodiments, surgical robot 102 can move the surgical instrument 608 to the desired pose quickly without any further assistance from a physician (unless the physician so desires).

As used herein, the term "pose" refers to the position and/or the rotational angle of one object (e.g., dynamic reference array, end-effector, surgical instrument, anatomical structure, etc.) relative to another object and/or to a defined coordinate system. A pose may therefore be defined based on only the multidimensional position of one object relative to another object and/or relative to a defined coordinate system, based on only the multidimensional rotational angles of the object relative to another object and/or to a defined coordinate system, or based on a combination of the multidimensional position and the multidimensional rotational angles. The term "pose" therefore is used to refer to position, rotational angle, or combination thereof.

In some further embodiments, surgical robot 102 can be configured to correct the path of the surgical instrument 608 if the surgical instrument 608 strays from the selected, preplanned trajectory. In some example embodiments, surgical robot 102 can be configured to permit stoppage, modification, and/or manual control of the movement of end-effector 112 and/or the surgical instrument 608. Thus, in use, in example embodiments, a physician or other user can operate the system 100, and has the option to stop, modify, or manually control the autonomous movement of end-effector 112 and/or the surgical instrument 608. Further details of surgical robot system 100 including the control and movement of a surgical instrument 608 by surgical robot 102 can be found in U.S. patent application Ser. No. 13/924,505, which is incorporated herein by reference in its entirety.

The robotic surgical system 100 can comprise one or more tracking markers 118 configured to track the movement of robot arm 104, end-effector 112, patient 210, and/or the surgical instrument 608 in three dimensions. In example embodiments, a plurality of tracking markers 118 can be mounted (or otherwise secured) thereon to an outer surface of the robot 102, such as, for example and without limitation, on base 106 of robot 102, on robot arm 104, or on the end-effector 112. In example embodiments, at least one tracking marker 118 of the plurality of tracking markers 118 can be mounted or otherwise secured to the end-effector 112. One or more tracking markers 118 can further be mounted (or otherwise secured) to the patient 210. In example embodiments, the plurality of tracking markers 118 can be positioned on the patient 210 spaced apart from the surgical field 208 to reduce the likelihood of being obscured by the surgeon, surgical instruments, or other parts of the robot 102. Further, one or more tracking markers 118 can be further mounted (or otherwise secured) to the surgical instruments 608 (e.g., a screwdriver, dilator, implant inserter, or the like). Thus, the tracking markers 118 enable each of the marked objects (e.g., the end-effector 112, the patient 210, and the surgical instruments 608) to be tracked by the robot 102 via the camera 200. In example embodiments, system 100 can use tracking information collected from each of the marked objects to calculate the pose (e.g., orientation and location), for example, of the end-effector 112, the surgical instrument 608 (e.g., positioned in the tube 114 of the end-effector 112), and the relative position of the patient 210.

The markers 118 may include radiopaque or optical markers. The markers 118 may be suitably shaped include spherical, spheroid, cylindrical, cube, cuboid, or the like. In example embodiments, one or more of markers 118 may be optical markers. In some embodiments, the positioning of one or more tracking markers 118 on end-effector 112 can maximize the accuracy of the positional measurements by serving to check or verify the position of end-effector 112. Further details of surgical robot system 100 including the control, movement and tracking of surgical robot 102 and of a surgical instrument 608 can be found in U.S. patent application Ser. No. 13/924,505, which is incorporated herein by reference in its entirety.

Example embodiments include one or more markers 118 coupled to the surgical instrument 608. In example embodiments, these markers 118, for example, coupled to the patient 210 and surgical instruments 608, as well as markers 118 coupled to the end-effector 112 of the robot 102 can comprise conventional infrared light-emitting diodes (LEDs) or an Optotrak® diode capable of being tracked using a commercially available infrared optical tracking system such as Optotrak®. Optotrak® is a registered trademark of Northern Digital Inc., Waterloo, Ontario, Canada. In other embodiments, markers 118 can comprise conventional reflective spheres capable of being tracked using a commercially available optical tracking system such as Polaris Spectra. Polaris Spectra is also a registered trademark of Northern Digital, Inc. In an example embodiment, the markers 118 coupled to the end-effector 112 are active markers which comprise infrared light-emitting diodes which may be turned on and off, and the markers 118 coupled to the patient 210 and the surgical instruments 608 comprise passive reflective spheres.

In example embodiments, light emitted from and/or reflected by markers 118 can be detected by camera 200 and can be used to monitor the pose and movement of the marked objects. In alternative embodiments, markers 118 can comprise a radio-frequency and/or electromagnetic reflector or transceiver and the camera 200 can include or be replaced by a radio-frequency and/or electromagnetic transceiver.

Figure 3:
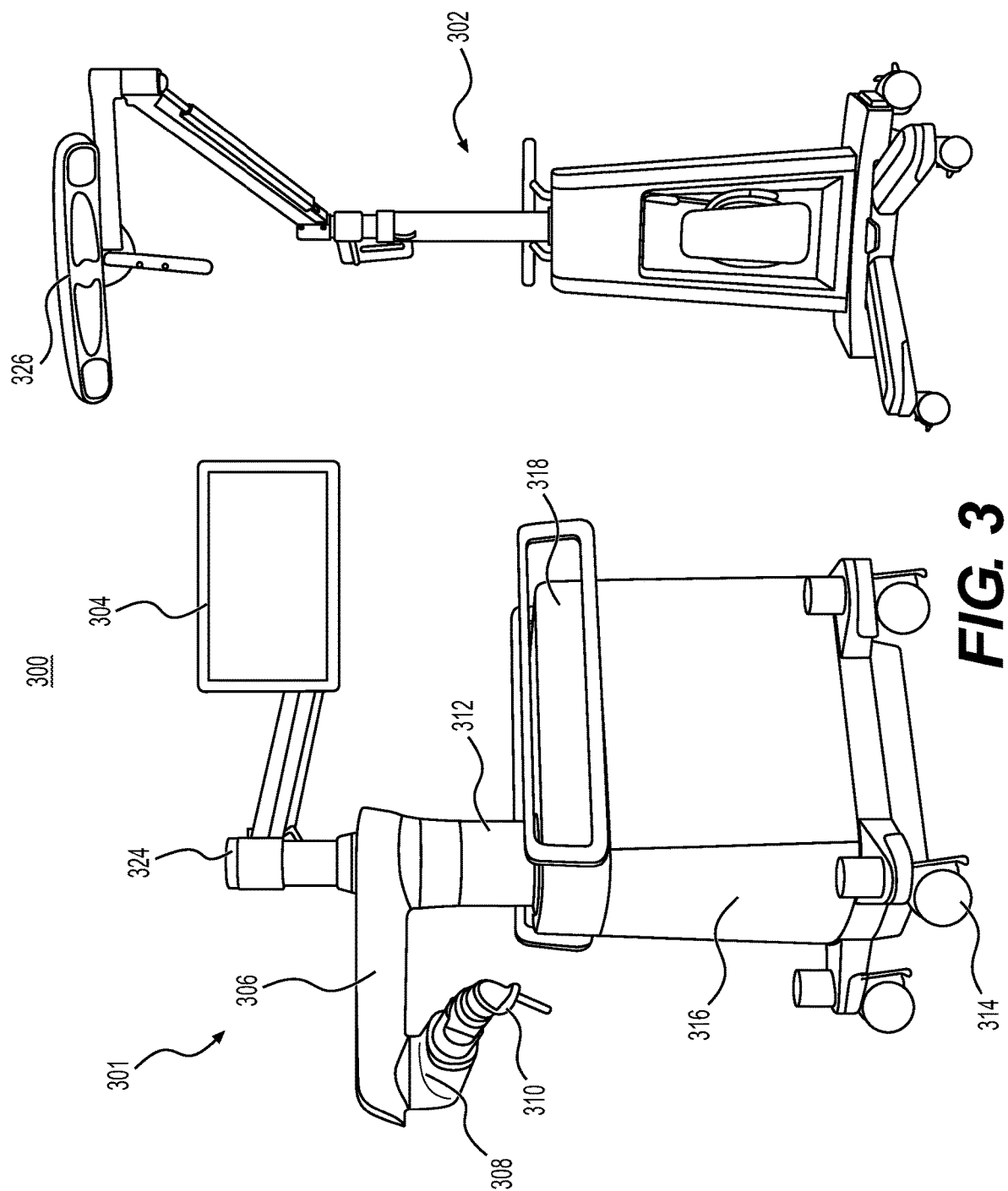
FIG. 3 illustrates a surgical robotic system in accordance with an example embodiment.

Similar to surgical robot system 100, FIG. 3 illustrates a surgical robot system 300 and camera stand 302, in a docked configuration, consistent with an example embodiment of the present disclosure. Surgical robot system 300 may comprise a robot 301 including a display 304, upper arm 306, lower arm 308, end-effector 310, vertical column 312, casters 314, cabinet 316, tablet drawer 318, and ring 324 of information. Camera stand 302 may comprise camera 326. These components are described in greater with respect to FIG. 5. FIG. 3 illustrates the surgical robot system 300 in a docked configuration where the camera stand 302 is nested with the robot 301, for example, when not in use. It will be appreciated by those skilled in the art that the camera 326 and robot 301 may be separated from one another and positioned at any appropriate pose during the surgical procedure, for example, as shown in FIGS. 1 and 2.

Figure 4:
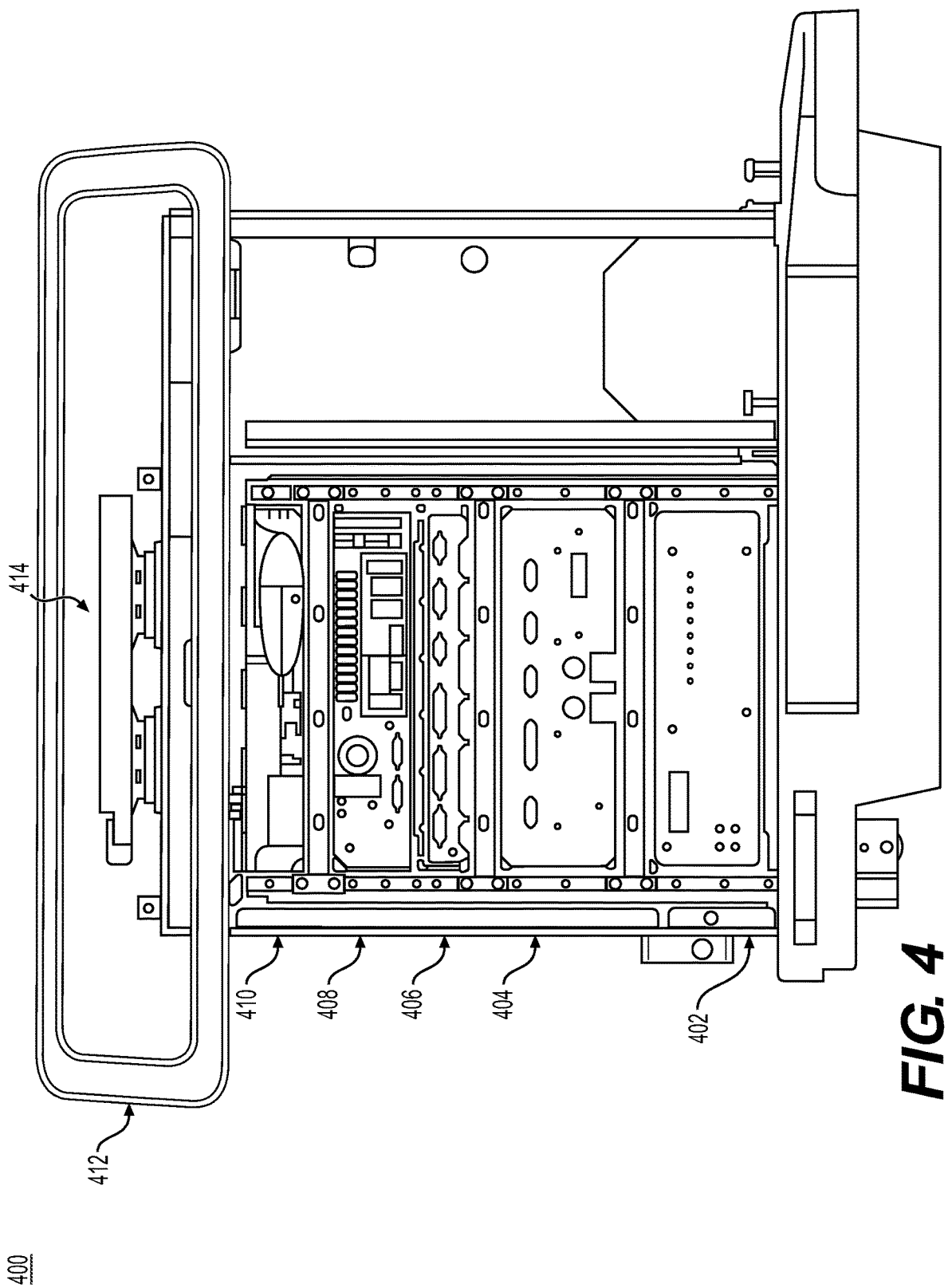

FIG. 4 illustrates a base 400 consistent with an example embodiment of the present disclosure. Base 400 may be a portion of surgical robot system 300 and comprise cabinet 316. Cabinet 316 may house certain components of surgical robot system 300 including but not limited to a battery 402, a power distribution module 404, a platform interface board module 406, a computer 408, a handle 412, and a tablet drawer 414. The connections and relationship between these components is described in greater detail with respect to FIG. 5.

FIG. 5 illustrates a block diagram of certain components of an example embodiment of surgical robot system 300. Surgical robot system 300 may comprise platform subsystem 502, computer subsystem 504, motion control subsystem 506, and tracking subsystem 532. Platform subsystem 502 may further comprise battery 402, power distribution module 404, platform interface board module 406, and tablet charging station 534. Computer subsystem 504 may further comprise computer 408, display 304, and speaker 536. Motion control subsystem 506 may further comprise driver circuit 508, motors 510, 512, 514, 516, 518, stabilizers 520, 522, 524, 526, end-effector 310, and controller 538. Tracking subsystem 532 may further comprise position sensor 540 and camera converter 542. System 300 may also comprise a foot pedal 544 and tablet 546.

Input power is supplied to system 300 via a power supply 548 which may be provided to power distribution module 404. Power distribution module 404 receives input power and is configured to generate different power supply voltages that are provided to other modules, components, and subsystems of system 300. Power distribution module 404 may be configured to provide different voltage supplies to platform interface board module 406, which may be provided to other components such as computer 408, display 304, speaker 536, driver circuit 508 to, for example, power motors 512, 514, 516, 518 and end-effector 310, motor 510, ring 324, camera converter 542, and other components for system 300 for example, fans for cooling the electrical components within cabinet 316.

Power distribution module 404 may also provide power to other components such as tablet charging station 534 that may be located within tablet drawer 318. Tablet charging station 534 may be in wireless or wired communication with tablet 546 for charging tablet 546. Tablet 546 may be used by a surgeon consistent with the present disclosure and described herein.

Power distribution module 404 may also be connected to battery 402, which serves as temporary power source in the event that power distribution module 404 does not receive power from power supply 548. At other times, power distribution module 404 may serve to charge battery 402 if necessary.

Other components of platform subsystem 502 may also include connector panel 320, control panel 322, and ring 324. Connector panel 320 may serve to connect different devices and components to system 300 and/or associated components and modules. Connector panel 320 may contain one or more ports that receive lines or connections from different components. For example, connector panel 320 may have a ground terminal port that may ground system 300 to other equipment, a port to connect foot pedal 544 to system 300, a port to connect to tracking subsystem 532, which may comprise position sensor 540, camera converter 542, and cameras 326 associated with camera stand 302.

Connector panel 320 may also include other ports to allow USB, Ethernet, HDMI communications to other components, such as computer 408.

Control panel 322 may provide various buttons or indicators that control operation of system 300 and/or provide information regarding system 300. For example, control panel 322 may include buttons to power on or off system 300, lift or lower vertical column 312, and lift or lower stabilizers 520-526 that may be designed to engage casters 314 to lock system 300 from physically moving. Other buttons may stop system 300 in the event of an emergency, which may remove all motor power and apply mechanical brakes to stop all motion from occurring. Control panel 322 may also have indicators notifying the user of certain system conditions such as a line power indicator or status of charge for battery 402.

Ring 324 may be a visual indicator to notify the user of system 300 of different modes that system 300 is operating under and certain warnings to the user.

Computer subsystem 504 includes computer 408, display 304, and speaker 536. Computer 504 includes an operating system and software to operate system 300. Computer 504 may receive and process information from other components (for example, tracking subsystem 532, platform subsystem 502, and/or motion control subsystem 506) in order to display information to the user. Further, computer subsystem 504 may also include speaker 536 to provide audio to the user.

Tracking subsystem 532 may include position sensor 540 and camera converter 542. Tracking subsystem 532 may correspond to camera stand 302 including camera 326 as described with respect to FIG. 3. Position sensor 540 may be camera 326. Tracking subsystem may track the pose of certain markers that are located on the different components of system 300 and/or instruments used by a user during a surgical procedure. This tracking may be conducted in a manner consistent with the present disclosure including the use of infrared technology that tracks the pose of active or passive elements, such as LEDs or reflective markers, respectively. The pose of structures having these types of markers may be provided to computer 408 which may be shown to a user on display 304. For example, a surgical instrument 608 having these types of markers and tracked in this manner (which may be referred to as a navigational space) may be shown to a user in relation to a three dimensional image of a patient's anatomical structure.

Motion control subsystem 506 may be configured to physically move vertical column 312, upper arm 306, lower arm 308, or rotate end-effector 310. The physical movement may be conducted through the use of one or more motors 510-518. For example, motor 510 may be configured to vertically lift or lower vertical column 312. Motor 512 may be configured to laterally move upper arm 308 around a point of engagement with vertical column 312 as shown in FIG. 3. Motor 514 may be configured to laterally move lower arm 308 around a point of engagement with upper arm 308 as shown in FIG. 3. Motors 516 and 518 may be configured to move end-effector 310 in a manner such that one may control the roll and one may control the tilt, thereby providing multiple angles that end-effector 310 may be moved. These movements may be achieved by controller 538 which may control these movements through load cells disposed on end-effector 310 and activated by a user engaging these load cells to move system 300 in a desired manner.

Moreover, system 300 may provide for automatic movement of vertical column 312, upper arm 306, and lower arm 308 through a user indicating on display 304 (which may be a touchscreen input device) the pose of a surgical instrument or component on three dimensional image of the patient's anatomy on display 304. The user may initiate this automatic movement by stepping on foot pedal 544 or some other input means.

FIG. 6 illustrates a surgical robot system 600 consistent with an example embodiment. Surgical robot system 600 may comprise end-effector 602, robot arm 604, guide tube 606, instrument 608, and robot base 610. Instrument instrument 608 may be attached to a tracking array 612 including one or more tracking markers (such as markers 118) and have an associated trajectory 614. Trajectory 614 may represent a path of movement that instrument 608 is configured to travel once it is positioned through or secured in guide tube 606, for example, a path of insertion of instrument 608 into a patient. In an example operation, robot base 610 may be configured to be in electronic communication with robot arm 604 and end-effector 602 so that surgical robot system 600 may assist a user (for example, a surgeon) in operating on the patient 210. Surgical robot system 600 may be consistent with previously described surgical robot system 100 and 300.

A tracking array 612 may be mounted on instrument 608 to monitor the pose (e.g., location and orientation) of instrument 608. The tracking array 612 may be attached to an instrument 608 and may comprise tracking markers 804. As best seen in FIG. 8, tracking markers 804 may be, for example, light emitting diodes and/or other types of reflective markers (e.g., markers 118 as described elsewhere herein). The tracking devices may be one or more line of sight devices associated with the surgical robot system. As an example, the tracking devices may be one or more cameras 200, 326 associated with the surgical robot system 100, 300 and may also track tracking array 612 for a defined domain or relative orientations of the instrument 608 in relation to the robot arm 604, the robot base 610, end-effector 602, and/or the patient 210. The tracking devices may be consistent with those structures described in connection with camera stand 302 and tracking subsystem 532.

FIGS. 7A, 7B, and 7C illustrate a top view, front view, and side view, respectively, of end-effector 602 consistent with an example embodiment. End-effector 602 may comprise one or more tracking markers 702. Tracking markers 702 may be light emitting diodes or other types of active and passive markers, such as tracking markers 118 that have been previously described. In an example embodiment, the tracking markers 702 are active infrared-emitting markers that are activated by an electrical signal (e.g., infrared light emitting diodes (LEDs)). Thus, tracking markers 702 may be activated such that the infrared markers 702 are visible to the camera 200, 326 or may be deactivated such that the infrared markers 702 are not visible to the camera 200, 326. Thus, when the markers 702 are active, the end-effector 602 may be controlled by the system 100, 300, 600, and when the markers 702 are deactivated, the end-effector 602 may be locked in position and unable to be moved by the system 100, 300, 600.

Markers 702 may be disposed on or within end-effector 602 in a manner such that the markers 702 are visible by one or more cameras 200, 326 or other tracking devices associated with the surgical robot system 100, 300, 600. The camera 200, 326 or other tracking devices may track end-effector 602 as it moves to different positions and viewing angles by following the movement of tracking markers 702. The pose of markers 702 and/or end-effector 602 may be shown on a display 110, 304 associated with the surgical robot system 100, 300, 600, for example, display 110 as shown in FIG. 2 and/or display 304 shown in FIG. 3. This display 110, 304 may allow a user to ensure that end-effector 602 is in a desirable position in relation to robot arm 604, robot base 610, the patient 210, and/or the user.

For example, as shown in FIG. 7A, markers 702 may be placed around the surface of end-effector 602 so that a tracking device placed away from the surgical field 208 and facing toward the robot 102, 301 and the camera 200, 326 is able to view at least 3 of the markers 702 through a range of common orientations of the end-effector 602 relative to the tracking system 100, 300, 600. For example, distribution of markers 702 in this way allows end-effector 602 to be monitored by the tracking devices when end-effector 602 is translated and rotated in the surgical field 208.

In addition, in example embodiments, end-effector 602 may be equipped with infrared (IR) receivers that can detect when an external camera 200, 326 is getting ready to read markers 702. Upon this detection, end-effector 602 may then illuminate markers 702. The detection by the IR receivers that the external camera 200, 326 is ready to read markers 702 may signal the need to synchronize a duty cycle of markers 702, which may be light emitting diodes, to an external camera 200, 326. This may also allow for lower power consumption by the robotic system as a whole, whereby markers 702 would only be illuminated at the appropriate time instead of being illuminated continuously. Further, in example embodiments, markers 702 may be powered off to prevent interference with other navigation instruments, such as different types of surgical instruments 608.

FIG. 8 depicts one type of surgical instrument 608 including a tracking array 612 and tracking markers 804. Tracking markers 804 may be of any type described herein including but not limited to light emitting diodes or reflective spheres. Markers 804 are monitored by tracking devices associated with the surgical robot system 100, 300, 600 and may be one or more of the line of sight cameras 200, 326. The cameras 200, 326 may track the pose of instrument 608 based on the poses of tracking array 612 and markers 804. A user, such as a surgeon 120, may orient instrument 608 in a manner so that tracking array 612 and markers 804 are sufficiently recognized by the tracking device or camera 200, 326 to display instrument 608 and markers 804 on, for example, display 110 of the example surgical robot system.

The manner in which a surgeon 120 may place instrument 608 into guide tube 606 of the end-effector 602 and adjust the instrument 608 is evident in FIG. 8. The hollow tube or guide tube 114, 606 of the end-effector 112, 310, 602 is sized and configured to receive at least a portion of the surgical instrument 608. The guide tube 114, 606 is configured to be oriented by the robot arm 104 such that insertion and trajectory for the surgical instrument 608 is able to reach a desired anatomical target within or upon the body of the patient 210. The surgical instrument 608 may include at least a portion of a generally cylindrical instrument. Although a screwdriver is exemplified as the surgical instrument 608, it will be appreciated that any suitable surgical instrument 608 may be positioned by the end-effector 602. Further examples of the surgical instrument 608 include one or more of a guide wire, cannula, a retractor, a drill, a reamer, a screwdriver, an insertion instrument, and a removal instrument. Although the guide tube 114, 606 is generally shown as having a cylindrical configuration, the guide tube 114, 606 may have any suitable shape, size and configuration desired to accommodate the surgical instrument 608 and access the surgical site.

FIGS. 9A-9C illustrate end-effector 602 and a portion of robot arm 604 consistent with an example embodiment. End-effector 602 may further comprise body 1202 and clamp 1204. Clamp 1204 may comprise handle 1206, balls 1208, spring 1210, and lip 1212. Robot arm 604 may further comprise depressions 1214, mounting plate 1216, lip 1218, and magnets 1220.

End-effector 602 may mechanically interface and/or engage with the surgical robot system and robot arm 604 through one or more couplings. For example, end-effector 602 may engage with robot arm 604 through a locating coupling and/or a reinforcing coupling. Through these couplings, end-effector 602 may fasten with robot arm 604 outside a flexible and sterile barrier. In an example embodiment, the locating coupling may be a magnetically kinematic mount and the reinforcing coupling may be a five bar over center clamping linkage.

With respect to the locating coupling, robot arm 604 may comprise mounting plate 1216, which may be non-magnetic material, one or more depressions 1214, lip 1218, and magnets 1220. Magnet 1220 is mounted below each of depressions 1214. Portions of clamp 1204 may comprise magnetic material and be attracted by one or more magnets 1220. Through the magnetic attraction of clamp 1204 and robot arm 604, balls 1208 become seated into respective depressions 1214. For example, balls 1208 as shown in FIG. 9B would be seated in depressions 1214 as shown in FIG. 9A. This seating may be considered a magnetically-assisted kinematic coupling. Magnets 1220 may be configured to be strong enough to support the entire weight of end-effector 602 regardless of the orientation of end-effector 602. The locating coupling may be any style of kinematic mount that uniquely restrains six degrees of freedom.

With respect to the reinforcing coupling, portions of clamp 1204 may be configured to be a fixed ground link and as such clamp 1204 may serve as a five bar linkage. Closing clamp handle 1206 may fasten end-effector 602 to robot arm 604 as lip 1212 and lip 1218 engage clamp 1204 in a manner to secure end-effector 602 and robot arm 604. When clamp handle 1206 is closed, spring 1210 may be stretched or stressed while clamp 1204 is in a locked position. The locked position may be a position that provides for linkage past center. Because of a closed position that is past center, the linkage will not open absent a force applied to clamp handle 1206 to release clamp 1204. Thus, in a locked position end-effector 602 may be robustly secured to robot arm 604.

Spring 1210 may be a curved beam in tension. Spring 1210 may be comprised of a material that exhibits high stiffness and high yield strain such as virgin PEEK (polyether-ether-ketone). The linkage between end-effector 602 and robot arm 604 may provide for a sterile barrier between end-effector 602 and robot arm 604 without impeding fastening of the two couplings.

The reinforcing coupling may be a linkage with multiple spring members. The reinforcing coupling may latch with a cam or friction based mechanism. The reinforcing coupling may also be a sufficiently powerful electromagnet that will support fastening end-effector 112 to robot arm 604. The reinforcing coupling may be a multi-piece collar completely separate from either end-effector 602 and/or robot arm 604 that slips over an interface between end-effector 602 and robot arm 604 and tightens with a screw mechanism, an over center linkage, or a cam mechanism.

Referring to FIGS. 10 and 11, prior to or during a surgical procedure, certain registration procedures may be conducted in order to track objects and a target anatomical structure of the patient 210 both in a navigation space and an image space. In order to conduct such registration, a registration system 1400 may be used as illustrated in FIG. 10.

In order to track the position of the patient 210, a patient tracking device 116 may include a patient fixation instrument 1402 to be secured to a rigid anatomical structure of the patient 210 and a dynamic reference array 1404 (also referred to as dynamic reference base (DRB)) may be securely attached to the patient fixation instrument 1402. For example, patient fixation instrument 1402 may be inserted into opening 1406 of dynamic reference array 1404. Dynamic reference array 1404, also referred to as a dynamic reference base, may contain markers 1408 that are visible to tracking devices, such as tracking subsystem 532. These markers 1408 may be optical markers or reflective spheres, such as tracking markers 118, as previously discussed herein.

Patient fixation instrument 1402 is attached to a rigid anatomy of the patient 210 and may remain attached throughout the surgical procedure. In an example embodiment, patient fixation instrument 1402 is attached to a rigid area of the patient 210, for example, a bone that is located away from the targeted anatomical structure subject to the surgical procedure. In order to track the targeted anatomical structure, dynamic reference array 1404 is associated with the targeted anatomical structure through the use of a registration fixture that is temporarily placed on or near the targeted anatomical structure in order to register the dynamic reference array 1404 with the pose of the targeted anatomical structure.

A registration fixture 1410 is attached to patient fixation instrument 1402 through the use of a pivot arm 1412. Pivot arm 1412 is attached to patient fixation instrument 1402 by inserting patient fixation instrument 1402 through an opening 1414 of registration fixture 1410. Pivot arm 1412 is attached to registration fixture 1410 by, for example, inserting a knob 1416 through an opening 1418 of pivot arm 1412.

Using pivot arm 1412, registration fixture 1410 may be placed over the targeted anatomical structure and its pose may be determined in an image space and navigation space using tracking markers 1420 and/or fiducials 1422 on registration fixture 1410. Registration fixture 1410 may contain a collection of markers 1420 that are visible in a navigational space (for example, markers 1420 may be detectable by tracking subsystem 532). Tracking markers 1420 may be optical markers visible in infrared light as previously described herein. Registration fixture 1410 may also contain a collection of fiducials 1422, for example, such as bearing balls, that are visible in an imaging space (for example, a three dimension CT image). As described in greater detail with respect to FIG. 11, using registration fixture 1410, the targeted anatomical structure may be associated with dynamic reference array 1404 thereby allowing depictions of objects in the navigational space to be overlaid on images of the anatomical structure. Dynamic reference array 1404, located at a position away from the targeted anatomical structure, may become a reference point thereby allowing removal of registration fixture 1410 and/or pivot arm 1412 from the surgical area.

FIG. 11 provides example operations 1500 for registration consistent with the present disclosure. The illustrated operations 1500 begins at step 1502 wherein an image volume containing a graphical representation (or image(s)) of the targeted anatomical structure may be imported into system 100, 300 600, for example computer 408. The image volume may be three dimensional CT or a fluoroscope scan of the targeted anatomical structure of the patient 210 which includes registration fixture 1410 and a detectable imaging pattern of markers 1420, e.g., fiducials.

At step 1504, an imaging pattern of markers 1420 (e.g., fiducials) is detected and registered in the imaging space and stored in computer 408. Optionally, at this time at step 1506, a graphical representation of the registration fixture 1410 may be overlaid on the images of the targeted anatomical structure.

At step 1508, a navigational pattern of registration fixture 1410 is detected and registered by recognizing markers 1420. Markers 1420 may be optical markers that are recognized in the navigation space through infrared light by tracking subsystem 532 via position sensor 540. Thus, the pose and other information of the targeted anatomical structure is registered in the navigation space. Therefore, registration fixture 1410 may be recognized in both the image space through the use of fiducials 1422 and the navigation space through the use of markers 1420. At step 1510, the registration of registration fixture 1410 in the image space is transferred to the navigation space. This transferal is done, for example, by using the relative position of the imaging pattern of fiducials 1422 compared to the position of the navigation pattern of markers 1420.

At step 1512, registration of the navigation space of registration fixture 1410 (having been registered with the image space) is further transferred to the navigation space of dynamic registration array 1404 attached to patient fixation instrument 1402. Thus, registration fixture 1410 may be removed and dynamic reference array 1404 may be used to track the targeted anatomical structure in both the navigation and image space because the navigation space is associated with the image space.

At steps 1514 and 1516, the navigation space may be overlaid on the image space and objects with markers visible in the navigation space (for example, surgical instruments 608 with optical markers 804). The objects may be tracked through graphical representations of the surgical instrument 608 on the images of the targeted anatomical structure.

FIGS. 12A-12B illustrate imaging systems 1304 that may be used in conjunction with robot systems 100, 300, 600 to acquire pre-operative, intra-operative, post-operative, and/or real-time image data of patient 210. Any appropriate subject matter may be imaged for any appropriate procedure using the imaging system 1304. The imaging system 1304 may be any imaging device such as imaging device 1306 and/or a C-arm 1308 device. It may be desirable to take x-rays of patient 210 from a number of different positions, without the need for frequent manual repositioning of patient 210 which may be required in an x-ray system. As illustrated in FIG. 12A, the imaging system 1304 may be in the form of a C-arm 1308 that includes an elongated C-shaped member terminating in opposing distal ends 1312 of the "C" shape. C-shaped member 1130 may further comprise an x-ray source 1314 and an image receptor 1316. The space within C-arm 1308 of the arm may provide room for the physician to attend to the patient substantially free of interference from x-ray support structure 1318. As illustrated in FIG. 12B, the imaging system may include imaging device 1306 having a gantry housing 1324 attached to a support structure imaging device support structure 1328, such as a wheeled mobile cart 1330 with wheels 1332, which may enclose an image capturing portion, not illustrated. The image capturing portion may include an x-ray source and/or emission portion and an x-ray receiving and/or image receiving portion, which may be disposed about one hundred and eighty degrees from each other and mounted on a rotor (not illustrated) relative to a track of the image capturing portion.

The image capturing portion may be operable to rotate three hundred and sixty degrees during image acquisition. The image capturing portion may rotate around a central point and/or axis, allowing image data of patient 210 to be acquired from multiple directions or in multiple planes. Although certain imaging systems 1304 are exemplified herein, it will be appreciated that any suitable imaging system may be selected by one of ordinary skill in the art.

Turning now to FIGS. 13A-13C, the surgical robot system 100, 300, 600 relies on accurate positioning of the end-effector 112, 602, surgical instruments 608, and/or the patient 210 (e.g., patient tracking device 116) relative to the desired surgical area. In the embodiments shown in FIGS. 13A-13C, the tracking markers 118, 804 are rigidly attached to a portion of the instrument 608 and/or end-effector 112.

FIG. 13A depicts part of the surgical robot system 100 with the robot 102 including base 106, robot arm 104, and end-effector 112. The other elements, not illustrated, such as the display, marker tracking cameras, etc. may also be present as described herein. FIG. 13B depicts a close-up view of the end-effector 112 with guide tube 114 and a plurality of tracking markers 118 rigidly affixed to the end-effector 112. In this embodiment, the plurality of tracking markers 118 are attached to the end-effector 112 configured as a guide tube. FIG. 13C depicts an instrument 608 (in this case, a probe 608A) with a plurality of tracking markers 804 rigidly affixed to the instrument 608. As described elsewhere herein, the instrument 608 could include any suitable surgical instrument, such as, but not limited to, guide wire, cannula, a retractor, a drill, a reamer, a screwdriver, an insertion instrument, a removal instrument, or the like.

When tracking an instrument 608, end-effector 112, or other object to be tracked in 3D, an array of tracking markers 118, 804 may be rigidly attached to a portion of the instrument 608 or end-effector 112. Preferably, the tracking markers 118, 804 are attached such that the markers 118, 804 are out of the way (e.g., not impeding the surgical operation, visibility, etc.). The markers 118, 804 may be affixed to the instrument 608, end-effector 112, or another object to be tracked, for example, with an array 612. Usually three or four markers 118, 804 are used with an array 612. The array 612 may include a linear section, a cross piece, and may be asymmetric such that the markers 118, 804 are at different relative poses with respect to one another. For example, as shown in FIG. 13C, a probe 608A with a 4-marker tracking array 612 is shown, and FIG. 13B depicts the end-effector 112 with a different 4-marker tracking array 612.

In FIG. 13C, the tracking array 612 functions as the handle 620 of the probe 608A. Thus, the four markers 804 are attached to the handle 620 of the probe 608A, which is out of the way of the shaft 622 and tip 624. Stereophotogrammetric tracking of these four markers 804 allows the instrument 608 to be tracked as a rigid body and for the tracking system 100, 300, 600 to precisely determine the location of the tip 624 and the orientation of the shaft 622 while the probe 608A is moved around within view of tracking cameras 200, 326.

To enable automatic tracking of one or more instruments 608, end-effector 112, or other object to be tracked in 3D (e.g., multiple rigid bodies), the markers 118, 804 on each instrument 608, end-effector 112, or the like, are arranged asymmetrically with a known inter-marker spacing. The reason for asymmetric alignment is so that it is unambiguous which marker 118, 804 corresponds to a particular pose on the rigid body and whether markers 118, 804 are being viewed from the front or back, i.e., mirrored. For example, if the markers 118, 804 were arranged in a square on the instrument 608 or end-effector 112, it would be unclear to the system 100, 300, 600 which marker 118, 804 corresponded to which corner of the square. For example, for the probe 608A, it would be unclear which marker 804 was closest to the shaft 622. Thus, it would be unknown which way the shaft 622 was extending from the array 612. Accordingly, each array 612 and thus each instrument 608, end-effector 112, or other object to be tracked should have a unique marker pattern to allow it to be distinguished from other instruments 608 or other objects being tracked.

Asymmetry and unique marker patterns allow the system 100, 300, 600 to detect individual markers 118, 804 then to check the marker spacing against a stored template to determine which instrument 608, end-effector 112, or another object they represent. Detected markers 118, 804 can then be sorted automatically and assigned to each tracked object in the correct order. Without this information, rigid body calculations could not then be performed to extract key geometric information, for example, such as instrument tip 624 and alignment of the shaft 622, unless the user manually specified which detected marker 118, 804 corresponded to which position on each rigid body. These concepts are commonly known to those skilled in the operations of 3D optical tracking.

Turning now to FIGS. 14A-14D, an alternative version of an end-effector 912 with moveable tracking markers 918A-918D is shown. In FIG. 14A, an array with moveable tracking markers 918A-918D are shown in a first configuration, and in FIG. 14B the moveable tracking markers 918A-918D are shown in a second configuration, which is angled relative to the first configuration. FIG. 14C shows the template of the tracking markers 918A-918D, for example, as seen by the cameras 200, 326 in the first configuration of FIG. 14A; and FIG. 14D shows the template of tracking markers 918A-918D, for example, as seen by the cameras 200, 326 in the second configuration of FIG. 14B.

In this embodiment, 4-marker array tracking is contemplated wherein the markers 918A-918D are not all in fixed position relative to the rigid body and instead, one or more of the array markers 918A-918D can be adjusted, for example, during testing, to give updated information about the rigid body that is being tracked without disrupting the process for automatic detection and sorting of the tracked markers 918A-918D.

When tracking any instrument, such as a guide tube 914 connected to the end-effector 912 of a robot system 100, 300, 600, the tracking array's primary purpose is to update the pose of the end-effector 912 in the camera coordinate system. When using the rigid system, for example, as shown in FIG. 13B, the array 612 of reflective markers 118 rigidly extend from the guide tube 114. Because the tracking markers 118 are rigidly connected, knowledge of the marker poses in the camera coordinate system also provides exact pose of the centerline, tip, and tail of the guide tube 114 in the camera coordinate system. Typically, information about the pose of the end-effector 112 from such an array 612 and information about the pose of a target trajectory from another tracked source are used to calculate the required moves that must be input for each axis of the robot 102 that will move the guide tube 114 into alignment with the trajectory and move the tip to a particular pose along the trajectory vector. Navigation information can be generated based on the calculated moves, which can be displayed for guiding an operator's movement of the end-effector 112 and/or instrument, and/or can be provided to one or more motors that can automatically or semi-automatically cause movement of the end-effector 112.

Sometimes, the desired trajectory is in an awkward or unreachable pose, but if the guide tube 114 could be swiveled, it could be reached. For example, a very steep trajectory pointing away from the base 106 of the robot 102 might be reachable if the guide tube 114 could be swiveled upward beyond the limit of the pitch (wrist up-down angle) axis, but might not be reachable if the guide tube 114 is attached parallel to the plate connecting it to the end of the wrist. To reach such a trajectory, the base 106 of the robot 102 might be moved or a different end-effector 112 with a different guide tube attachment might be exchanged with the working end-effector. Both of these solutions may be time consuming and cumbersome.

As best seen in FIGS. 14A and 14B, if the array 908 is configured such that one or more of the markers 918A-918D are not in a fixed position and instead, one or more of the markers 918A-918D can be adjusted, swiveled, pivoted, or moved, the robot 102 can provide updated information about the object being tracked without disrupting the detection and tracking process. For example, one of the markers 918A-918D may be fixed in position and the other markers 918A-918D may be moveable; two of the markers 918A-918D may be fixed in position and the other markers 918A-918D may be moveable; three of the markers 918A-918D may be fixed in position and the other marker 918A-918D may be moveable; or all of the markers 918A-918D may be moveable.

In the embodiment shown in FIGS. 14A and 14B, markers 918A, 918 B are rigidly connected directly to a base 906 of the end-effector 912, and markers 918C, 918D are rigidly connected to the guide tube 914. Similar to array 612, array 908 may be provided to attach the markers 918A-918D to the end-effector 912, instrument 608, or another object to be tracked. In this case, however, the array 908 is comprised of a plurality of separate components. For example, markers 918A, 918B may be connected to the base 906 with a first array 908A, and markers 918C, 918D may be connected to the guide tube 914 with a second array 908B. Marker 918A may be affixed to a first end of the first array 908A and marker 918B may be separated a linear distance and affixed to a second end of the first array 908A. While first array 908 is substantially linear, second array 908B has a bent or V-shaped configuration, with respective root ends, connected to the guide tube 914, and diverging therefrom to distal ends in a V-shape with marker 918C at one distal end and marker 918D at the other distal end. Although specific configurations are exemplified herein, it will be appreciated that other asymmetric designs including different numbers and types of arrays 908A, 908B and different arrangements, numbers, and types of markers 918A-918D are contemplated.

The guide tube 914 may be moveable, swivelable, or pivotable relative to the base 906, for example, across a hinge 920 or another connector to the base 906. Thus, markers 918C, 918D are moveable such that when the guide tube 914 pivots, swivels, or moves, markers 918C, 918D also pivot, swivel, or move. As best seen in FIG. 14A, guide tube 914 has a longitudinal axis 916 which is aligned in a substantially normal or vertical orientation such that markers 918A-918D have a first configuration. Turning now to FIG. 14B, the guide tube 914 is pivoted, swiveled, or moved such that the longitudinal axis 916 is now angled relative to the vertical orientation such that markers 918A-918D have a second configuration, different from the first configuration.

In contrast to the embodiment described for FIGS. 14A-14D, if a swivel existed between the guide tube 914 and the arm 104 (e.g., the wrist attachment) with all four markers 918A-918D remaining attached rigidly to the guide tube 914 and this swivel was adjusted by the user, the robotic system 100, 300, 600 would not be able to automatically detect that the guide tube 914 orientation had changed. The robotic system 100, 300, 600 would track the positions of the marker array 908 and would calculate incorrect robot axis moves assuming the guide tube 914 was attached to the wrist (the robot arm 104) in the previous orientation. By keeping one or more markers 918A-918D (e.g., two markers 918C, 918D) rigidly on the guide tube 914 and one or more markers 918A-918D (e.g., two markers 918A, 918B) across the swivel, automatic detection of the new position becomes possible and correct robot moves are calculated based on the detection of a new instrument or end-effector 112, 912 on the end of the robot arm 104.

One or more of the markers 918A-918D are configured to be moved, pivoted, swiveled, or the like according to any suitable means. For example, the markers 918A-918D may be moved by a hinge 920, such as a clamp, spring, lever, slide, toggle, or the like, or any other suitable mechanism for moving the markers 918A-918D individually or in combination, moving the arrays 908A, 908B individually or in combination, moving any portion of the end-effector 912 relative to another portion, or moving any portion of the instrument 608 relative to another portion.

As shown in FIGS. 14A and 14B, the array 908 and guide tube 914 may become reconfigurable by simply loosening the clamp or hinge 920, moving part of the array 908A, 908B relative to the other part 908A, 908B, and retightening the hinge 920 such that the guide tube 914 is oriented in a different position. For example, two markers 918C, 918D may be rigidly interconnected with the guide tube 914 and two markers 918A, 918B may be rigidly interconnected across the hinge 920 to the base 906 of the end-effector 912 that attaches to the robot arm 104. The hinge 920 may be in the form of a clamp, such as a wing nut or the like, which can be loosened and retightened to allow the user to quickly switch between the first configuration (FIG. 14A) and the second configuration (FIG. 14B).

The cameras 200, 326 detect the markers 918A-918D, for example, in one of the templates identified in FIGS. 14C and 14D. If the array 908 is in the first configuration (FIG. 14A) and tracking cameras 200, 326 detect the markers 918A-918D, then the tracked markers match Array Template 1 as shown in FIG. 14C. If the array 908 is the second configuration (FIG. 14B) and tracking cameras 200, 326 detect the same markers 918A-918D, then the tracked markers match Array Template 2 as shown in FIG. 14D. Array Template 1 and Array Template 2 are recognized by the system 100, 300, 600 as two distinct instruments, each with its own uniquely defined spatial relationship between guide tube 914, markers 918A-918D, and robot attachment. The user could therefore adjust the position of the end-effector 912 between the first and second configurations without notifying the system 100, 300, 600 of the change and the system 100, 300, 600 would appropriately adjust the movements of the robot 102 to stay on trajectory.

In this embodiment, there are two assembly positions in which the marker array matches unique templates that allow the system 100, 300, 600 to recognize the assembly as two different instruments or two different end-effectors. In any position of the swivel between or outside of these two positions (namely, Array Template 1 and Array Template 2 shown in FIGS. 14C and 14D, respectively), the markers 918A-918D would not match any template and the system 100, 300, 600 would not detect any array present despite individual markers 918A-918D being detected by cameras 200, 326, with the result being the same as if the markers 918A-918D were temporarily blocked from view of the cameras 200, 326. It will be appreciated that other array templates may exist for other configurations, for example, identifying different instruments 608 or other end-effectors 112, 912, etc.

In the embodiment described, two discrete assembly positions are shown in FIGS. 14A and 14B. It will be appreciated, however, that there could be multiple discrete positions on a swivel joint, linear joint, combination of swivel and linear joints, pegboard, or other assembly where unique marker templates may be created by adjusting the position of one or more markers 918A-918D of the array relative to the others, with each discrete position matching a particular template and defining a unique instrument 608 or end-effector 112, 912 with different known attributes. In addition, although exemplified for end-effector 912, it will be appreciated that moveable and fixed markers 918A-918D may be used with any suitable instrument 608 or other object to be tracked.

When using an external 3D tracking system 100, 300, 600 to track a full rigid body array of three or more markers attached to a robot's end-effector 112 (for example, as depicted in FIGS. 13A and 13B), it is possible to directly track or to calculate the 3D pose of every section of the robot 102 in the coordinate system of the tracking cameras 200, 326. The geometric orientations of joints relative to the tracker are known by design, and the linear or angular positions of joints are known from encoders for each motor of the robot 102, fully defining the 3D positions of all of the moving parts from the end-effector 112 to the base 116. Similarly, if a tracker were mounted on the base 106 of the robot 102 (not shown), it is likewise possible to track or calculate the 3D position of every section of the robot 102 from base 106 to end-effector 112 based on known joint geometry and joint positions from each motor's encoder.

In some situations, it may be desirable to track the poses of all segments of the robot 102 from fewer than three markers 118 rigidly attached to the end-effector 112. Specifically, if an instrument 608 is introduced into the guide tube 114, it may be desirable to track full rigid body motion of the robot 902 with only one additional marker 118 being tracked.

Turning now to FIGS. 15A-15E, an alternative version of an end-effector 1012 having only a single tracking marker 1018 is shown. End-effector 1012 may be similar to the other end-effectors described herein, and may include a guide tube 1014 extending along a longitudinal axis 1016. A single tracking marker 1018, similar to the other tracking markers described herein, may be rigidly affixed to the guide tube 1014. This single marker 1018 can serve the purpose of adding missing degrees of freedom to allow full rigid body tracking and/or can serve the purpose of acting as a surveillance marker to ensure that assumptions about robot and camera positioning are valid.

The single tracking marker 1018 may be attached to the end-effector 1012 as a rigid extension to the end-effector 1012 that protrudes in any convenient direction and does not obstruct the surgeon's view. The tracking marker 1018 may be affixed to the guide tube 1014 or any other suitable pose of on the end-effector 1012. When affixed to the guide tube 1014, the tracking marker 1018 may be positioned at a location between first and second ends of the guide tube 1014. For example, in FIG. 15A, the single tracking marker 1018 is shown as a reflective sphere mounted on the end of a narrow shaft 1017 that extends forward from the guide tube 1014 and is positioned longitudinally above a mid-point of the guide tube 1014 and below the entry of the guide tube 1014. This position allows the marker 1018 to be generally visible by cameras 200, 326 but also would not obstruct vision of the surgeon 120 or collide with other instruments or objects in the vicinity of surgery. In addition, the guide tube 1014 with the marker 1018 in this position is designed for the marker array on any instrument 608 introduced into the guide tube 1014 to be visible at the same time as the single marker 1018 on the guide tube 1014 is visible.

As shown in FIG. 15B, when a snugly fitting instrument 608 is placed within the guide tube 1014, the instrument 608 becomes mechanically constrained in 4 of 6 degrees of freedom. That is, the instrument 608 cannot be rotated in any direction except about the longitudinal axis 1016 of the guide tube 1014 and the instrument 608 cannot be translated in any direction except along the longitudinal axis 1016 of the guide tube 1014. In other words, the instrument 608 can only be translated along and rotated about the centerline of the guide tube 1014. If two more parameters are known, such as (1) an angle of rotation about the longitudinal axis 1016 of the guide tube 1014; and (2) a position along the guide tube 1014, then the position of the end-effector 1012 in the camera coordinate system becomes fully defined.

Referring now to FIG. 15C, the system 100, 300, 600 should be able to know when an instrument 608 is actually positioned inside of the guide tube 1014 and is not instead outside of the guide tube 1014 and just somewhere in view of the tracking cameras 200, 326. The instrument 608 has a longitudinal axis or centerline 616 and an array 612 with a plurality of tracked markers 804. The rigid body calculations may be used to determine where the centerline 616 of the instrument 608 is located in the camera coordinate system based on the tracked position of the array 612 on the instrument 608.

The fixed normal (perpendicular) distance DF from the single marker 1018 to the centerline or longitudinal axis 1016 of the guide tube 1014 is fixed and is known geometrically, and the position of the single marker 1018 can be tracked. Therefore, when a detected distance DD from instrument centerline 616 to single marker 1018 matches the known fixed distance DF from the guide tube axis 1016 (e.g., guide tube centerline) to the single marker 1018, it can be determined that the instrument 608 is either within the guide tube 1014 (axis 616, 1016 of instrument 608 and guide tube 1014 coincident) or happens to be at some point in the locus of possible positions where this distance DD matches the fixed distance DF. For example, in FIG. 15C, the normal detected distance DD from instrument centerline 616 to the single marker 1018 matches the fixed distance DF from guide tube axis 1016 to the single marker 1018 in both frames of data (tracked marker coordinates) represented by the transparent instrument 608 in two positions, and thus, additional considerations may be needed to determine when the instrument 608 is located in the guide tube 1014.

Turning now to FIG. 15D, programmed logic can be used to look for frames of tracking data in which the detected distance DD from instrument centerline 616 to single marker 1018 remains fixed at the correct length despite the instrument 608 moving in space by more than some minimum distance relative to the single sphere 1018 to satisfy the condition that the instrument 608 is moving within the guide tube 1014. For example, a first frame F1 may be detected with the instrument 608 in a first position and a second frame F2 may be detected with the instrument 608 in a second position (namely, moved linearly with respect to the first position). The markers 804 on the instrument array 612 may move by more than a given amount (e.g., more than 5 mm total) from the first frame F1 to the second frame F2. Even with this movement, the detected distance DD from the instrument centerline vector C' to the single marker 1018 is substantially identical in both the first frame F1 and the second frame F2.

Logistically, the surgeon 120 or user could place the instrument 608 within the guide tube 1014 and slightly rotate it or slide it down into the guide tube 1014 and the system 100, 300, 600 would be able to detect that the instrument 608 is within the guide tube 1014 from tracking of the five markers (four markers 804 on instrument 608 plus single marker 1018 on guide tube 1014). Knowing that the instrument 608 is within the guide tube 1014, all 6 degrees of freedom may be calculated that define the position and orientation of the end-effector 1012 in space. Without the single marker 1018, even if it is known with certainty that the instrument 608 is within the guide tube 1014, it is unknown where the guide tube 1014 is located along the instrument's centerline vector C' and how the guide tube 1014 is rotated relative to the centerline vector C'.

With emphasis on FIG. 15E, the presence of the single marker 1018 being tracked as well as the four markers 804 on the instrument 608, it is possible to construct the centerline vector C' of the guide tube 1014 and instrument 608 and the normal vector through the single marker 1018 and through the centerline vector C'. This normal vector has an orientation that is in a known orientation relative to the forearm of the robot distal to the wrist (in this example, oriented parallel to that segment) and intersects the centerline vector C' at a specific fixed position. For convenience, three mutually orthogonal vectors k', j', can be constructed, as shown in FIG. 15E, defining rigid body position and orientation of the guide tube 1014. One of the three mutually orthogonal vectors k' is constructed from the centerline vector C', the second vector j is constructed from the normal vector through the single marker 1018, and the third vector i' is the vector cross product of the first and second vectors k', j'. The robot's joint positions relative to these vectors k', j', i' are known and fixed when all joints are at zero, and therefore rigid body calculations can be used to determine the pose of any section of the robot relative to these vectors k', j', i' when the robot is at a home position. During robot movement, if the positions of the instrument markers 804 (while the instrument 608 is in the guide tube 1014) and the position of the single marker 1018 are detected from the tracking system, and angles/linear positions of each joint are known from encoders, then position and orientation of any section of the robot can be determined.

In some embodiments, it may be useful to fix the orientation of the instrument 608 relative to the guide tube 1014. For example, the end-effector guide tube 1014 may be oriented in a particular position about its axis 1016 to allow machining or implant positioning. Although the orientation of anything attached to the instrument 608 inserted into the guide tube 1014 is known from the tracked markers 804 on the instrument 608, the rotational orientation of the guide tube 1014 itself in the camera coordinate system is unknown without the additional tracking marker 1018 (or multiple tracking markers in other embodiments) on the guide tube 1014. This marker 1018 provides essentially a "clock position" from −180° to +180° based on the orientation of the marker 1018 relative to the centerline vector C'. Thus, the single marker 1018 can provide additional degrees of freedom to allow full rigid body tracking and/or can act as a surveillance marker to ensure that assumptions about the robot and camera positioning are valid.

FIG. 16 is a block diagram of operations 1100 for navigating and moving the end-effector 1012 (or any other end-effector described herein) of the robot 102 to a desired target trajectory. Another use of the single marker 1018 on the end-effector 1012 or guide tube 1014 is as part of the operations 1100 enabling the automated safe movement of the robot 102 without a full tracking array attached to the robot 102. These operations 1100 function when the tracking cameras 200, 326 do not move relative to the robot 102 (i.e., they are in a fixed position), the tracking system's coordinate system and robot's coordinate system are co-registered, and the robot 102 is calibrated such that the position and orientation of the guide tube 1014 can be accurately determined in the robot's Cartesian coordinate system based only on the encoded positions of each robotic axis.

For these operations 1100, the coordinate systems of the camera based tracker and the robot should be co-registered, meaning that the coordinate transformation from the tracking system's Cartesian coordinate system to the robot's Cartesian coordinate system is needed. For convenience, this coordinate transformation can be a 4×4 matrix of translations and rotations that is well known in the field of robotics. This transformation will be termed Tcr to refer to "transformation—camera to robot". Once this transformation is known, any new frame of tracking data, which is received as x, y, z coordinates in vector form for each tracked marker, can be multiplied by the 4×4 matrix and the resulting x, y, z coordinates will be in the robot's coordinate system. To obtain Tcr, a full tracking array on the robot is tracked while it is rigidly attached to the robot at a pose that is known in the robot's coordinate system, then known rigid body operations are used to calculate the transformation of coordinates. It should be evident that any instrument 608 inserted into the guide tube 1014 of the robot 102 can provide the same rigid body information as a rigidly attached array when the additional marker 1018 is also read. That is, the instrument 608 need only be inserted to any position within the guide tube 1014 and at any rotation within the guide tube 1014, not to a fixed position and orientation. Thus, it is possible to determine Tcr by inserting any instrument 608 with a tracking array 612 into the guide tube 1014 and reading the instrument's array 612 plus the single marker 1018 of the guide tube 1014 while at the same time determining from the encoders on each axis the current pose of the guide tube 1014 in the robot's coordinate system.

Logic for navigating and moving the robot 102 to a target trajectory is provided in the operations 1100 of FIG. 16. Before entering the loop 1102, it is assumed that the transformation Tcr was previously stored. Thus, before entering loop 1102, in step 1104, after the robot base 106 is secured, greater than or equal to one frame of tracking data of an instrument inserted in the guide tube while the robot is static is stored; and in step 1106, the transformation of robot guide tube position from camera coordinates to robot coordinates Tcr is calculated from this static data and previous calibration data. Tcr should remain valid as long as the cameras 200, 326 do not move relative to the robot 102. If the cameras 200, 326 move relative to the robot 102, and Tcr needs to be re-obtained, the system 100, 300, 600 can be made to prompt the user to insert an instrument 608 into the guide tube 1014 and then automatically perform the necessary calculations.

In the flowchart of operations 1100, each frame of data collected includes the tracked position of the DRB 1404 on the patient 210, the tracked position of the single marker 1018 on the end-effector 1014, and a snapshot of the positions of each robotic axis. From the positions of the robot's axes, the pose of the single marker 1018 on the end-effector 1012 is calculated. This calculated position is compared to the actual position of the marker 1018 as recorded from the tracking system. If the values agree, it can be assured that the robot 102 is in a known pose. The transformation Tcr is applied to the tracked position of the DRB 1404 so that the target for the robot 102 can be provided in terms of the robot's coordinate system. The robot 102 can then be commanded to move to reach the target.

After steps 1104, 1106, loop 1102 includes step 1108 receiving rigid body information for DRB 1404 from the tracking system; step 1110 transforming target tip and trajectory from image coordinates to tracking system coordinates; and step 1112 transforming target tip and trajectory from camera coordinates to robot coordinates (apply Tcr). Loop 1102 further includes step 1114 receiving a single stray marker position for robot from tracking system; and step 1116 transforming the single stray marker from tracking system coordinates to robot coordinates (apply stored Tcr). Loop 1102 also includes step 1118 determining current pose of the single robot marker 1018 in the robot coordinate system from forward kinematics. The information from steps 1116 and 1118 is used to determine step 1120 whether the stray marker coordinates from transformed tracked position agree with the calculated coordinates being less than a given tolerance. If yes, proceed to step 1122, calculate and apply robot move to target x, y, z and trajectory. If no, proceed to step 1124, halt and require full array insertion into guide tube 1014 before proceeding; step 1126 after array is inserted, recalculate Tcr; and then proceed to repeat steps 1108, 1114, and 1118.

These operations 1100 have advantages over operations in which the continuous monitoring of the single marker 1018 to verify the pose is omitted. Without the single marker 1018, it would still be possible to determine the position of the end-effector 1012 using Tcr and to send the end-effector 1012 to a target pose but it would not be possible to verify that the robot 102 was actually in the expected pose. For example, if the cameras 200, 326 had been bumped and Tcr was no longer valid, the robot 102 would move to an erroneous pose. For this reason, the single marker 1018 provides value with regard to safety.

For a given fixed position of the robot 102, it is theoretically possible to move the tracking cameras 200, 326 to a new pose in which the single tracked marker 1018 remains unmoved since it is a single point, not an array. In such a case, the system 100, 300, 600 would not detect any error since there would be agreement in the calculated and tracked poses of the single marker 1018. However, once the robot's axes caused the end-effector 102, i.e., guide tube, to move to a new pose, the calculated and tracked poses would disagree and the safety check would be effective.

The term "surveillance marker" may be used, for example, in reference to a single marker that is in a fixed pose relative to the DRB 1404. In this instance, if the DRB 1404 is bumped or otherwise dislodged, the relative pose of the surveillance marker changes and the surgeon 120 can be alerted that there may be a problem with navigation. Similarly, in the embodiments described herein, with a single marker 1018 on the robot's guide tube 1014, the system 100, 300, 600 can continuously check whether the cameras 200, 326 have moved relative to the robot 102. If registration of the tracking system's coordinate system to the robot's coordinate system is lost, such as by cameras 200, 326 being bumped or malfunctioning or by the robot malfunctioning, the system 100, 300, 600 can alert the user and corrections can be made. Thus, this single marker 1018 can also be thought of as a surveillance marker for the robot 102.

It should be clear that with a full array permanently mounted on the robot 102 (e.g., the plurality of tracking markers 702 on end-effector 602 shown in FIGS. 7A-7C) such functionality of a single marker 1018 as a robot surveillance marker is not needed because it is not required that the cameras 200, 326 be in a fixed position relative to the robot 102, and Tcr is updated at each frame based on the tracked position of the robot 102. Reasons to use a single marker 1018 instead of a full array are that the full array is more bulky and obtrusive, thereby blocking the surgeon's view and access to the surgical field 208 more than a single marker 1018, and line of sight to a full array is more easily blocked than line of sight to a single marker 1018.

Turning now to FIGS. 17A-17B and 18A-18B, instruments 608, such as implant holders 608B, 608C, are depicted which include both fixed and moveable tracking markers 804, 806. The implant holders 608B, 608C may have a handle 620 and an outer shaft 622 extending from the handle 620. The shaft 622 may be positioned substantially perpendicular to the handle 620, as shown, or in any other suitable orientation. An inner shaft 626 may extend through the outer shaft 622 with a knob 628 at one end. Implant 10, 12 connects to the shaft 622, at the other end, at tip 624 of the implant holder 608B, 608C using typical connection mechanisms known to those of skill in the art. The knob 628 may be rotated, for example, to expand or articulate the implant 10, 12. U.S. Pat. Nos. 8,709,086 and 8,491,659, which are incorporated by reference herein, describe expandable fusion devices and operations for installation.

When tracking the instrument 608, such as implant holder 608B, 608C, the tracking array 612 may contain a combination of fixed markers 804 and one or more moveable markers 806 which make up the array 612 or is otherwise attached to the implant holder 608B, 608C. The navigation array 612 may include at least one or more (e.g., at least two) fixed position markers 804, which are positioned with a known pose relative to the implant holder instrument 608B, 608C. These fixed markers 804 would not be able to move in any orientation relative to the instrument geometry and would be useful in defining where the instrument 608 is in space. In addition, at least one marker 806 is present which can be attached to the array 612 or the instrument itself which is capable of moving within a pre-determined boundary (e.g., sliding, rotating, etc.) relative to the fixed markers 804. The system 100, 300, 600 (e.g., the software) correlates the position of the moveable marker 806 to a particular position, orientation, or other attribute of the implant 10 (such as height of an expandable interbody spacer shown in FIGS. 17A-17B or angle of an articulating interbody spacer shown in FIGS. 18A-18B). Thus, the system and/or the user can determine the height or angle of the implant 10, 12 based on the pose of the moveable marker 806.

In the embodiment shown in FIGS. 17A-17B, four fixed markers 804 are used to define the implant holder 608B and a fifth moveable marker 806 is able to slide within a pre-determined path to provide feedback on the implant height (e.g., a contracted position or an expanded position). FIG. 17A shows the implant 10 (e.g., expandable spacer) at its initial height, and FIG. 17B shows the implant 10 (e.g., expandable spacer) in the expanded state with the moveable marker 806 translated to a different position. In this case, the moveable marker 806 moves closer to the fixed markers 804 when the implant 10 is expanded, although it is contemplated that this movement may be reversed or otherwise different. The amount of linear translation of the marker 806 would correspond to the height of the implant 10. Although only two positions are shown, it would be possible to have this as a continuous function whereby any given expansion height could be correlated to a specific position of the moveable marker 806.

Turning now to FIGS. 18A-18B, four fixed markers 804 are used to define the implant holder 608C and a fifth, moveable marker 806 is configured to slide within a predetermined path to provide feedback on the implant articulation angle. FIG. 18A shows the articulating spacer 12 at its initial linear state, and FIG. 18B shows the spacer 12 in an articulated state at some offset angle with the moveable marker 806 translated to a different position. The amount of linear translation of the marker 806 would correspond to the articulation angle of the implant 12. Although only two positions are shown, it would be possible to have this as a continuous function whereby any given articulation angle could be correlated to a specific position of the moveable marker 806.

In these embodiments, the moveable marker 806 slides continuously to provide feedback about an attribute of the implant 10, 12 based on position. It is also contemplated that there may be discreet positions that the moveable marker 806 must be in which would also be able to provide further information about an implant attribute. In this case, each discreet configuration of all markers 804, 806 correlates to a specific geometry of the implant holder 608B, 608C and the implant 10, 12 in a specific orientation or at a specific height. In addition, any motion of the moveable marker 806 could be used for other variable attributes of any other type of navigated implant.

Although depicted and described with respect to linear movement of the moveable marker 806, the moveable marker 806 should not be limited to just sliding as there may be applications where rotation of the marker 806 or other movements could be useful to provide information about the implant 10, 12. Any relative change in position between the set of fixed markers 804 and the moveable marker 806 could be relevant information for the implant 10, 12 or other device. In addition, although expandable and articulating implants 10, 12 are exemplified, the instrument 608 could work with other medical devices and materials, such as spacers, cages, plates, fasteners, nails, screws, rods, pins, wire structures, sutures, anchor clips, staples, stents, bone grafts, biologics, cements, or the like.

Turning now to FIG. 19A, it is envisioned that the robot end-effector 112 is interchangeable with other types of end-effectors 112. Moreover, it is contemplated that each end-effector 112 may be able to perform one or more functions based on a desired surgical procedure. For example, the end-effector 112 having a guide tube 114 may be used for guiding an instrument 608 as described herein. In addition, end-effector 112 may be replaced with a different or alternative end-effector 112 that controls a surgical device, instrument, or implant, for example.

The alternative end-effector 112 may include one or more devices or instruments coupled to and controllable by the robot. By way of non-limiting example, the end-effector 112, as depicted in FIG. 19A, may comprise a retractor (for example, one or more retractors disclosed in U.S. Pat. Nos. 8,992,425 and 8,968,363) or one or more mechanisms for inserting or installing surgical devices such as expandable intervertebral fusion devices (such as expandable implants exemplified in U.S. Pat. Nos. 8,845,734; 9,510,954; and 9,456,903), stand-alone intervertebral fusion devices (such as implants exemplified in U.S. Pat. Nos. 9,364,343 and 9,480,579), expandable corpectomy devices (such as corpectomy implants exemplified in U.S. Pat. Nos. 9,393,128 and 9,173,747), articulating spacers (such as implants exemplified in U.S. Pat. No. 9,259,327), facet prostheses (such as devices exemplified in U.S. Pat. No. 9,539,031), laminoplasty devices (such as devices exemplified in U.S. Pat. No. 9,486,253), spinous process spacers (such as implants exemplified in U.S. Pat. No. 9,592,082), inflatables, fasteners including polyaxial screws, uniplanar screws, pedicle screws, posted screws, and the like, bone fixation plates, rod constructs and revision devices (such as devices exemplified in U.S. Pat. No. 8,882,803), artificial and natural discs, motion preserving devices and implants, spinal cord stimulators (such as devices exemplified in U.S. Pat. No. 9,440,076), and other surgical devices. The end-effector 112 may include one or instruments directly or indirectly coupled to the robot for providing bone cement, bone grafts, living cells, pharmaceuticals, or another deliverable to a surgical target. The end-effector 112 may also include one or more instruments designed for performing a discectomy, kyphoplasty, vertebrostenting, dilation, or other surgical procedure.

The end-effector itself and/or the implant, device, or instrument may include one or more markers 118 such that the pose (e.g., location and position) of the markers 118 may be identified in three-dimensions. It is contemplated that the markers 118 may include active or passive markers 118, as described herein, that may be directly or indirectly visible to the cameras 200. Thus, one or more markers 118 located on an implant 10, for example, may provide for tracking of the implant 10 before, during, and after implantation.

As shown in FIG. 19B, the end-effector 112 may include an instrument 608 or portion thereof that is coupled to the robot arm 104 (for example, the instrument 608 may be coupled to the robot arm 104 by the coupling mechanism shown in FIGS. 9A-9C) and is controllable by the robot system 100. Thus, in the embodiment shown in FIG. 19B, the robot system 100 is able to insert implant 10 into a patient and expand or contract the expandable implant 10. Accordingly, the robot system 100 may be configured to assist a surgeon or to operate partially or completely independently thereof. Thus, it is envisioned that the robot system 100 may be capable of controlling each alternative end-effector 112 for its specified function or surgical procedure.

Although the robot and associated systems described herein are generally described with reference to spine applications, it is also contemplated that the robot system is configured for use in other surgical applications, including but not limited to, surgeries in trauma or other orthopedic applications (such as the placement of intramedullary nails, plates, and the like), cranial, neuro, cardiothoracic, vascular, colorectal, oncological, dental, and other surgical operations and procedures.

Ultrasonic Tracking of Surgical Robot End-Effector and Surgical Instrument Relative to Patient Image Volume Numerous embodiments have been described above that utilize optical based tracking of markers. Those robotic systems utilized optical tracking registered to a medical image as feedback for positioning the robotic arm 104 while also displaying graphical representations of instruments and anatomical structure captured in patient image volumes to enable user visualization of instrument poses relative to the anatomical structure. Although optical-based tracking can be fast and accurate, the tracking is interrupted by blockage of line-of-sight from the markers, e.g., on patient reference array and/or the robot, to the tracking cameras 200, 326. Additionally, many surgical workflows with these robotic systems require x-rays or CT scans for operation and/or registration.

Various embodiments of the present disclosure are directed to using a US transducer to track the pose of the surgical robot end-effector relative to patient anatomical structure captured in an image volume. A surgical robot system is provided that is positioned relative to anatomical structure by US feedback. The surgical robot system may operate without optical tracking or may be configured to operate in conjunction with optical tracking. As will be explained below, optical tracking may be used to assist in localizing anatomical structure being imaged by a US transducer and to provide operational redundancy to take over when, for example, the US transducer ceases to contact the patient and therefore no longer outputs US imaging data of the anatomical structure.

In one embodiment, a surgical robot system comprises a robot, a US transducer, and at least one processor. The robot has a robot base, a robot arm coupled to the robot base, and an end-effector coupled to the robot arm, such as explained above in accordance with some embodiments. The end-effector is configured to guide movement of a surgical instrument. The US transducer is coupled to the end-effector and operative to output US imaging data of anatomical structure proximately located to the end-effector. The at least one processor is operative to obtain a 3D image volume, such as MRI or CT, for the patient and to track pose of the end-effector relative to the anatomical structure captured in the image volume based on the US imaging data.

The at least one processor may include one or more data processing circuits (e.g., microprocessor and/or digital signal processor), which may be collocated or distributed across one or more data networks. The at least one processor is configured to execute program code in one or more memories to perform some or all of the operations and methods for one or more of the embodiments disclosed herein. The at least one processor may be part of the one or more the controllers disclosed herein.

The end-effector can be located at the distal end of the moving arm and include a guide tube through which surgical procedures are performed.

FIG. 20 depicts a guide tube 2000 configured to guide movement of a surgical instrument through the guide tube, and a US transducer unit 2010 formed by an array of US transducers spaced apart along a leading edge of the guide tube 2000. In the example embodiment illustrated in FIG. 20, the US transducers are spaced apart to form a ring-shape and are at least partially disposed within a leading edge of the guide tube 2000. A ring-shaped US transducers layout may be especially operationally accurate because the ring can provide improved US visualization of anatomical structure, e.g., bone and tissues, that are distal, medial, and lateral proximately located to the guide tube 2000.

Other configurations of US transducers may be used with the guide tube 2000. For example, a plurality of US transducers can spaced apart on the leading edge of the guide tube 2000 or near the leading edge of the guide tube 2000, such as being mounted on a support base that is connected to the guide tube 2000 or another part of the end-effector.

In one embodiment, the US transducer comprises a planar array of US transducers that are connected by a mounting arm to the guide tube 2000 or another part of the end-effector.

When performing surgery, particularly cranial surgery, the inability to track the instrument (e.g., probe or tool) tip can leave the surgeon prone to coming into contact with various structures that are not the intended target, therefore risking harm to the patient. By having some trackable instrument reference able to be located on a live ultrasound, the surgeon has an understanding of the instrument tip location relative to the point of interest in the image during the procedure.

In accordance with some further embodiments, the US transducer can be configured to also sense the position of a surgical instrument that is passed through the guide tube 2000, such as through the ring-shaped US transducers 2010.

A US visible reference on a surgical instrument would limit dangers arising if the surgical instrument is not tracked, such as inaccurate instrument trajectories, instruments appearing to be bending off along trajectories, or moving the instrument too deep or shallow relative to a desired location. By utilizing live US while the tracked instrument progresses through the surgical site, the instrument's fiducials not only give information of general positioning relative to the surgical site from above, but depending on the type and number of fiducials used, more information can be given. The details of what information is identifiable in the US imaging data depends on characteristics of the fiducials formed on the tool. One type of fiducial may enable tracking of instrument depth, while a pattern of fiducials may enable tracking of instrument rotation and tracking trajectory, such as relating to skiving, bending, etc.

Discrete fiducial features such as protrusions, slots, holes or indentations could be formed on the surface of the shaft of a surgical instrument, such as a screwdriver, drill, awl, tap, etc. The US transducer can be configured to output US imaging data that captures locations of the discrete features on the surgical instrument and captures anatomical structure proximately located to the guide tube 2000. At least one processor (also referred to herein as "processor" below for brevity) is operative to identify in the US imaging data locations of the discrete features which are spaced apart along the surgical instrument and sensed by the US transducer, and to determine pose of the surgical instrument relative to the end-effector based on the locations of the discrete features identified in the US imaging data.

In one embodiment, the processor compares a template of defined locations of the markings the instrument shaft to the locations of markings identified in the US imaging data, and can determine there from the exact longitudinal and rotational position of the surgical instrument within the guide tube 2000. The processor may be configured to graphically display a representation of the surgical instrument with a determined pose overlaid on a graphical representation of anatomical structure captured in a medical image volume. This functionality can be advantageous over systems that require optical or other tracking to visualize the surgical instrument during insertion.

FIGS. 21A-21C depict differently configured surgical instruments, which have shafts configured to be tracked relative to the guide tube 2000 using the US transducer.

FIG. 21A depicts a surgical instrument 2100 with patterned indentations 2102 at calibrated longitudinal and radial positions on the shaft. The indentations 2112 are configured to be detectable by the ring-shaped US transducers 2010 and captured in the US imaging data to enable the processor to determine the depth and rotational pose of the surgical instrument 2100 within the guide tube 2000 as the instrument shaft passes through the ring-shaped array of US transducers 2010.

A surgical instrument can have discrete features configured in other manners to be detectable by the US transducers 2010. In some embodiments, the discrete features are configured as indentations, protrusions, slots, and/or holes spaced apart along a surface of the surgical instrument.

As explained above, the US transducer can comprise an array of US transducers. To determine pose of the surgical instrument relative to the end-effector based on the locations of the discrete features identified in the US imaging data, the processor can be operative to determine depth of the surgical instrument relative to a location on the end-effector based on counting a number of the discrete features identified in the US imaging data from individual ones of the US transducers. Alternatively or additionally, when determining pose of the surgical instrument relative to the end-effector, the processor can determine rotation of the surgical instrument relative to the end-effector based on identifying rotation of the discrete features identified in the US imaging data between adjacent US transducers in the array.

In a further embodiment, to determine pose of the surgical instrument relative to the end-effector based on the locations of the discrete features identified in the US imaging data, the processor is operative to match a spatial pattern of the locations of the discrete features identified in the US imaging data to content of a template for the surgical instrument which defines a pattern of the discrete features arranged around the surface of the surgical instrument as a function of locations along a length of the surgical instrument.

In the example of FIG. 21A, the indentations 2102 are formed with alternating patterns 2104a and 2104b along a length of the shaft. Pattern 2104a includes a group of indentations 2102 which are circumferentially spaced around the shaft and spirally offset in a rotational direction along the length of the shaft. In contrast, pattern 2104b includes another group of indentations 2102 which are circumferentially spaced around the shaft and spirally offset in an opposite rotational direction along the length of the shaft relative to the pattern 2104a. The processor can operate to match a spatial pattern of the locations of the discrete features identified in the US imaging data to content of a template for the surgical instrument which defines the alternating patterns 2104a and 2104b, to track the depth and rotation of the shaft relative to the guide tube 2000.

FIG. 22 depicts the surgical instrument 2100 of FIG. 21A at three different depths and rotations relative to the guide tube 2000. The pose of the surgical instrument 2100 relative to the guide tube 2000 is being detected by the US transducer 2010. Because the indentations 2102 in the instrument shaft are at calibrated locations along the shaft and have a calibrated spatially shifting pattern that can be matched by the processor to a template, the surgical instrument's 2100 depth within the guide tube 2000 can be tracked using the US imaging data. As shown in FIG. 22, the US signals emitted from each US transducer 2010 fan out and the indentations 2102 in the passing instrument surface reflect back US signals which are sensed by the US transducers 2010 and captured in the US imaging data output by the US transducers 2010.

In some other embodiments, the processor is operative to identify in the US imaging data locations of layers of materials of the surgical instrument, where adjacent layers of the materials have different reflectivity to US. The processor determines pose of the surgical instrument relative to the end-effector based on the locations of the layers of materials of the surgical instrument identified in the US imaging data.

FIG. 21B depicts a surgical instrument 2110 having a shaft with alternating layers of materials, e.g., 2112, 2114, 2112, 2114, and so-on, stacked along a primary axis of the shaft, where adjacent layers 2112 and 2114 of the materials have different reflectivity to US. For example, layers 2112 may be substantially non-reflective to US and layers 2114 may be substantially reflective to US. In this manner, the differing reflectivity of the alternating layers 2112 and 2114 generates a pattern of US reflections which are identifiable in the US imaging data from the US transducer. The processor can track depth of the surgical instrument 2110 relative to the guide tube 2100 based on the pattern. The processor can count the stripes as they go by to determine depth or spacing between layers could be varied to provide a detectable depth pattern corresponding to different tool depth within a guide tube.

FIG. 21C depicts a surgical instrument 2110 having a shaft with alternating layers of materials, e.g., 2122, 2124, 2122, 2124, and so-on, forming helical stripes spiraling about a primary axis of the shaft, where adjacent layers 2122 and 2124 of the materials have different reflectivity to US. For example, layers 2122 may be substantially non-reflective to US and layers 2124 may be substantially reflective to US. In this manner, the differing reflectivity of the alternating layers 2122 and 2124 generates a pattern of US reflections that are identifiable in the US imaging data from the US transducer. The processor can track depth and rotation of the surgical instrument 2110 relative to the guide tube 2100 based on the pattern. The processor can count the helix stripes as they pass by the US transducers or the pitch (stripes per cm) of the helix can be configured differently at different longitudinal positions to provide markers of specific depths.

In another embodiment, a surgical instrument 2110 has a shaft with layers of materials forming stripes extending parallel to a primary axis of the shaft, where adjacent layers of the materials have different reflectivity to US. In this manner, the differing reflectivity of the alternating layers generates a pattern of US reflections which are identifiable in the US imaging data from the US transducer. The processor can track rotation of the surgical instrument relative to the guide tube 2100 based on the pattern.

Some further embodiments are directed to using US imaging data from a US transducer in combination with at least one processor ("processor) to track pose of the robot end-effector relative to anatomical structure captured in an image volume for the patient.

FIG. 23 depicts a flowchart of operations that can be performed by a processor to track pose of the end-effector relative to anatomical structure captured in an image volume based on US imaging data from a US transducer.

Referring to FIG. 23, the processor generates 2300 US images of the anatomical structure based on the US imaging data, and matches 2302 the anatomical structure captured in one of the US images to the anatomical structure captured in the image volume. The processor then determines 2304 the pose of the end-effector relative to the anatomical structure captured in the image volume based on the matching and the known orientation of the end-effector relative to the US transducers.

Some further embodiments are directed to generating steering information based on the target pose for surgical instrument in a presently tracked pose of the end-effector relative to the anatomical structure captured in the image volume, such as according to the flowchart of operations depicted in the flowchart of FIG. 24.

Referring to FIG. 24, a processor is operative to determine 2400 a target pose for the surgical instrument based on a surgical plan defining where a surgical procedure is to be performed using the surgical instrument on the anatomical structure captured in the image volume. The processor is further operative to generate 2402 steering information based on the target pose for the surgical instrument and a present tracked pose of the end-effector relative to the anatomical structure captured in the image volume, the steering information indicating where the surgical instrument and/or the end-effector need to be moved.

In a further embodiment, the processor is operative to control movement of at least one motor, which is operatively connected to move the robot arm relative to the robot base, based on the steering information to guide movement of the end-effector so the surgical instrument becomes positioned with the target pose FIG. 25 depicts a more detailed flowchart of operations and be performed by at least one processor ("processor") to generate navigation information that can be used to guide movement of the robot end-effector toward a target pose, in accordance with some embodiments.

Referring to FIG. 25, the processor obtains 2400 a 3D MRI or CT image volume of the patient. The processor receives 2402 input from a surgeon who inputs a trajectory plan on anatomical structure captured in an image volume, or the surgical plan may be auto-generated by a surgical planning computer and or by the processor. For example, the surgeon may use an electronic pen to draw on a graphical representation of anatomical structure captured in the image volume to input the surgical trajectory. The robot arm is manually or automatically positioned 2404 by the processor so that the US transducer becomes in contact with the patient's skin surface. The processor registers 2406 (synchronizes coordinate systems) between coordinate systems of the US transducer, the robot, and the anatomical structure captured in the image volume. The processor displays 2408 a current pose (e.g., position and rotational orientation) of the end-effector, e.g., guide tube 2000, relative to the anatomical structure captured in the image volume.

The processor determines 2410 whether the end-effector is aligned with a target pose and, if so, the processor performs further operations 2414 associated with being on-target, such as tracking depth and rotation of a surgical instrument guided by the end-effector. In contrast, when the determination 2410 is that the end-effector is not aligned with the target pose, the processor generates 2412 navigation information computed to indicate a direction of movement as needed for the end-effector to reach the target pose and initiates further guided movement of the end-effector toward the target pose using the navigation information.

In one embodiment, the US transducer must remain in contact with the patient's skin while moving so that the US imaging data from the US transducer continuously captures anatomical structure of the patient under the skin. A 6-axis load cell at or near the leading edge of the robot arm may be used to sense pressure of the US transducer and/or end-effector against the patient and ensure that the US transducer stays in gentle contact with the skin. As transitional robot movement occurs while traveling to the target pose, force feedback at the end-effector can be monitored from the load cell and robot arm angle and position can be responsively adjusted by the processor to maintain a light force on the skin surface while minimizing shear forces, such as described below with regard to FIGS. 26A-C. The force feedback can also be utilized to ensure that, during this transitional movement, the US transducer remains normal to the skin surface to provide the clearest imaging of the anatomical structures in the US imaging data.

FIGS. 26A-C depicts a sequence of snapshots of a robotic arm 104 of the surgical robot system 100 moving laterally to a target pose while automatically maintaining contact between the US transducer 2010 and the patient's skin 2600 and normal to the body surface. Responsive to a leading edge of the guide tube 2000 reaching a trajectory at a target location, the processor can operate to automatically adjust the robot arm 104 so that the guide tube 2000 becomes oriented with a pose that matches the target trajectory.

Optical tracking may be used to assist in localizing anatomical structure being imaged by a US transducer and to provide operational redundancy to take over when, for example, the US transducer ceases to contact the patient and therefore no longer outputs US imaging data of the anatomical structure.

During a surgical procedure, the surgical robot system 100 may plan or predict a series of arm movements required to move from a current position to a new position with the expectation that the US transducer will lose contact with the patient's skin and, therefore, cease outputting US imaging data of the anatomical structure which is used for tracking location relative to the anatomical structure captured an image volume for the patient. It is further anticipated that the US transducer will eventually come back in contact with the skin again near a target location and therefore resume outputting US imaging data of the anatomical structure in a region near the target location. As with a continuous contact mode (e.g., where the US transducer maintains contact patient's skin), force feedback from one or more sensors can be used to interrupt controlled movement of the end-effector to ensure safe movement without unexpected collision with the patient or other obstacle. Processor operations can be configured to enter a "floating" mode in case of detected collision where the robot arm 104 is controlled to be easily moved in any direction with light applied force by a user and/or wait for user intervention.

To clearly indicate to the user when the robot is in contact with the patient or is unable to determine pose based on US imaging data (e.g., US transducer has ceased contacting skin) and is estimating where the robot is based on the last known location, the surgical robot system 100 can be configured to display anatomical structure in different shades, such as grayscale, and/or different colors to visually differentiate between when the US transducer is properly contacting a patient to provide US imaging data that is being used to identify pose of the US transducer versus when the US transducer is not satisfying that condition. Displaying the anatomical structure in different shades and/or colors notifies the user when the displayed navigation information can be most accurately relied upon for precise navigation (i.e., when relying upon US imaging data of anatomical structure matching anatomical structure captured in the image volume) and when the navigation information is a rougher estimate (i.e., when not relying upon such US imaging data) but may still be useful for planning or non-surgical localization.

In either of these modes (accurate or estimate), once the end-effector 112 control by the surgical robot 102 approaches the target location, the surgical robot 102 will adjust the arm 104 orientation to match the desired trajectory orientation while also monitoring feedback from the load cell. Load feedback would be used to adjust the end-effector 112 pose so that the desired orientation is achieved while maintaining constant low applied force between the US transducer and the patient's skin.

During any phase of movement where the US transducer is in contact with the patient's skin, accuracy of the displayed information depends upon rapid re-registration (e.g., matching 2302 in FIG. 23) of the anatomical structure captured in the US images generated (2300 in FIG. 23) based on the US imaging data to the anatomical structure captured an image volume for the patient. For example, the anatomical structure captured in a US image generated based on the US imaging data from the US detector is rapidly re-registered (matched 2302 in FIG. 23) with the anatomical structure captured in the CT or MM scan volume so that the pose of the end-effector 112 (e.g., guide tube 2000) relative to the patient's anatomical structure is known in near real time. For each of the US images, e.g., "frame", which is generated based on the US imaging data, the US image is registered to the CT or MRI scan volume, providing an updated computed pose of the US transducer relative to anatomical structure captured in the scan (image) volume. Knowing the pose of the end-effector 112 (e.g., guide tube 2000) relative to the US transducer and the pose of the anatomical structure captured in the CT or MRI scan volume relative to the US transducer, it is then possible to determine the pose of the end-effector 112 (e.g., guide tube 2000) relative to the anatomical structure captured in the CT or MRI scan volume. The end-effector 112 (e.g., guide tube 2000) can then be visualized by rendering a graphic representation of the end-effector 112 (e.g., guide tube 2000) relative to (e.g., as a graphical overlay) the anatomical structure captured in the CT or MM scan volume. For clear visualization of the end-effector 112 (e.g., guide tube 2000) relative to the anatomical structure, the scan volume can be displayed as a multiplanar reconstruction (MPR) view showing three mutually orthogonal slice views, two parallel and one perpendicular to the end-effector as is currently used in the Globus Excelsius GPS system.

Registration of the pose of the US transducer to the CT volume may be computationally intensive and have relatively lower reliability if the registration is not initiated with direction or seeding to a carefully selected portion of the CT volume, such as if the registration operations attempted to look for a match across a large region of the CT volume. Therefore, the first registration may be computationally intensive or may require user intervention to achieve desired accuracy or successful completion. However, once the first registration has been completed, subsequent re-registrations can be performed with less computational resources needed because the system uses knowledge of exactly where the end-effector 112 (e.g., guide tube 2000) has moved in its coordinate system via kinematics. When moving to a new target location, the system can assume that the patient anatomy is in a fixed location to get within a few millimeters of the target location and then focus the registration matching search to within a small range of the predicted target anatomy for a registration match between the structure of the anatomical structure captured in one of the US images to structure of the anatomical structure captured in the selected portion of the CT volume. The system can then refine its determination of the end-effector 112 (e.g., guide tube 2000) pose and reach final alignment between target trajectory and end-effector 112 (e.g., guide tube 2000) pose.

In accordance with some further embodiments, the surgical robot system uses kinematic sensors on the robot, e.g., at pivot joints of the robot arms 104 and end-effector 112, providing kinematic movement data to continue to track pose of the end-effector 112 during period while the US transducer is not outputting US imaging data of the anatomical structure, e.g., while the US transducer is lifted not in contact with the patient. The surgical robot system subsequently resumes using the US imaging data, and may cease any further concurrent use of kinematic movement data, when the US transducer has again contacted the patient and become re-registered to the CT volume or other image volume for the patient.

In one embodiment, the surgical robot system includes kinematic sensors connected to the robot arm and which are operative to output kinematic movement data indicating change in pose of the robot arm relative to the robot base. The at least one processor ("processor") is operative to, after tracking pose of the end-effector relative to the anatomical structure captured in the image volume based on the US imaging data for a period of time and responsive to the US transducer ceasing to output US imaging data of the anatomical structure proximately located to the end-effector, trigger continued tracking of the pose of the end-effector relative to the anatomical structure captured in the image volume based on the kinematic movement data. The processor is further operative to respond to the US transducer resuming output of US imaging data of the anatomical structure proximately located to the end-effector, by triggering continued tracking of the pose of the end-effector relative to the anatomical structure captured in the image volume based on the US imaging data.

In a further related embodiment, the processor may cease tracking of the pose of the end-effector relative to the anatomical structure captured in the image volume based on the kinematic movement data, responsive to the US transducer resuming output of US imaging data of the anatomical structure proximately located to the end-effector.

In a further related embodiment, the processor can be configured to constrain the search space for matching the anatomical structure captured in one of the US images to the anatomical structure captured in the image volume, based on a current pose tracked based on the kinematic movement data (position encoders at each robotic joint). The processor can operate to trigger continued tracking of the pose of the end-effector relative to the anatomical structure captured in the image volume based on the US imaging data, by operations which include generating US images of the anatomical structure based on the US imaging data, selecting a portion of the image volume based on a present pose of the end-effector as tracked relative to the anatomical structure captured in the image volume based on the kinematic movement data, and matching structure of the anatomical structure captured in one of the US images to structure of the anatomical structure captured in the selected portion of the image volume. The processor determines the pose of the end-effector relative to the anatomical structure captured in the selected portion of the image volume based on the matching.

In some other related embodiments, the surgical robot system uses a different color and/or shading to visually indicate to a user when the tracking is performed based on US imaging data distinguished from when the tracking is performed based on kinematic movement data. In one embodiment, the processor is further operative to display a graphical representation of the end-effector with the determined pose relative to a graphical representation of the anatomy captured in the image volume. The processor uses a different color and/or shading to display the graphical representation of the end-effector relative to the graphical representation of the anatomy captured in the image volume to visually indicate to a user when the pose of the end-effector relative to the anatomical structure captured in the image volume is being tracked based on the US imaging data distinguishable by the user from when the pose of the end-effector relative to the anatomical structure captured in the image volume is being tracked based on the kinematic movement data.

Some other embodiments are directed to using machine vision to ensure that the US transducer remains in contact with the patient's skin surface while the end-effector is moved to a target pose via a determined navigated pathway, and while avoiding collisions with other objects or body surfaces. The surgical robot system may further utilize machine learning in combination with machine vision. Visible light cameras could detect and map the surface of the patient's body and use a machine learning model, such as a neural network model, to determine an optimal pathway through which the end-effector is to be moved. For example, when moving across the spine from left to right, the computer operations can process the surface map and the starting and target locations through a machine learning model that has been trained on spinous (e.g., indicating that skin surface contours rise to a peak and then descend) and other body geometries to output a preferred navigation pathway for the end-effector to be moved to the target location. The robot movement would be responsively controlled for the end-effector and US transducer to rise-up and rotationally angle over the spine and then decline back down without having to rely solely on force feedback, thereby making the movement smoother and more reliable for maintaining desired contact between the US transducer and the patient's skin during the movement.

Additionally, the prediction of how movement should occur can come from transducer feedback and fitting of the patient to a body model. For example, the US imaging data from the US transducer may be used to register the bony anatomy of the patient to an existing CT volume, but the CT volume may poorly capture the body surface. Accordingly, by fitting the patient's body to a computerized model that is based on age, gender, weight, ethnicity, etc. the body surface contours relative to the current location of the end-effector can be predicted and used when generating the preferred navigation pathway.

In another embodiment, the surgical robot system operates using a combination of optical tracking input and US transducer input. In one embodiment, the surgical robot system only utilizes the US imaging data from the US transducer while the US transducer is close to a target location, e.g., where registration is performed with at least a threshold accuracy. All secondary transitional movement can be guided by optical feedback.

For example, in some embodiments the surgical robot system switches from US tracking to optical tracking responsive to the US transducer ceasing to output US imaging data of the anatomical structure (e.g., losing contact with the patient).

In one embodiment, the surgical robot system includes a tracking camera operative to track pose of markers on the robot arm and/or the end-effector. The at least one processor ("processor") is operative to, after tracking pose of the end-effector relative to the anatomical structure captured in the image volume based on the US imaging data for a period of time and responsive to the US transducer ceasing to output US imaging data of the anatomical structure proximately located to the end-effector, trigger continued tracking of the pose of the end-effector relative to the anatomical structure captured in the image volume based on output of the tracking camera. The processor also responds to the US transducer resuming output of US imaging data of the anatomical structure proximately located to the end-effector, by triggering continued tracking of the pose of the end-effector relative to the anatomical structure captured in the image volume based on the US imaging data.

In a further embodiment, the surgical robot system ceases tracking of the pose of the end-effector relative to the anatomical structure captured in the image volume based on output of the tracking camera.

In another embodiment, the surgical robot system switches from optical tracking back to US tracking responsive to the US transducer resuming output of US imaging data of the anatomical structure (e.g., resuming contact with the patient).

In one embodiment, the tracking camera operative to capture location of markers on the robot arm and/or the end-effector. The processor is operative to track pose of the markers. The processor, after tracking pose of the end-effector relative to the anatomical structure captured in the image volume based on the US imaging data for a period of time and responsive to the US transducer ceasing to output US imaging data of the anatomical structure proximately located to the end-effector, is operative to trigger continued tracking of the pose of the end-effector relative to the anatomical structure captured in the image volume based on output of the tracking camera. Responsive to the US transducer resuming output of US imaging data of the anatomical structure proximately located to the end-effector, the processor triggers continued tracking of the pose of the end-effector relative to the anatomical structure captured in the image volume based on the US imaging data.

In a further embodiment, the surgical robot system ceases tracking of the pose of the end-effector relative to the anatomical structure captured in the image volume based on output of the tracking camera.

Some further embodiments are directed to the surgical robot system initially using optical tracking to track pose of the end-effector while moving to a target region of the patient and then switching to tracking pose of the end-effector using US tracking and constraining the search space for the matching.

In one embodiment, the surgical robot system includes a tracking camera operative to output optical tracking data indicating pose of a reference array on the robot arm and/or the end-effector and further indicating pose of a reference array at a defined location on the patient that is approximately correlated to a defined location in the anatomical structure captured in the image volume. The at least one processor ("processor") is operative to track pose of the end-effector relative to the anatomical structure captured in the image volume based on the optical tracking data, while the end-effector is moved toward the patient for the US transducer to contact the patient. Responsive to the US transducer contacting the patient and beginning to output US imaging data of the anatomical structure proximately located to the end-effector, the processor generates US images of the anatomical structure based on the US imaging data. The processor selects a portion of the image volume based on a present pose of the end-effector as tracked relative to the anatomical structure captured in the image volume based on the optical tracking data, and matches structure of the anatomical structure captured in one of the US images to structure of the anatomical structure captured in the selected portion of the image volume. The processor determines the pose of the end-effector relative to the anatomical structure captured in the selected portion of the image volume based on the matching.

In another related embodiment, the processor is operative to determine a target pose for the surgical instrument based on a surgical plan defining where a surgical procedure is to be performed using the surgical instrument on the anatomical structure captured in the image volume. The processor generates steering information based on the target pose for the surgical instrument and a present tracked pose of the end-effector relative to the anatomical structure captured in the image volume, the steering information indicating where the surgical instrument and/or the end-effector need to be moved. The pose of the end-effector relative to the anatomical structure captured in the image volume is tracked using the optical tracking data during a time period while the US transducer is not outputting US imaging data of the anatomical structure proximately located to the end-effector. In contrast, the pose of the end-effector relative to the anatomical structure captured in the image volume is tracked using the US imaging data and without using the optical tracking data during another time period while the US transducer is outputting the US imaging data of the anatomical structure proximately located to the end-effector.

FIG. 27 depicts a flowchart of operations for controlling movement of the robot arm to a target pose using a combination of optical feedback control and US transducer feedback control, in accordance with some embodiments.

Referring to FIG. 27, the processor obtains 2700 a 3D MRI or CT image volume of the patient. The processor receives 2702 input from a surgeon who inputs a trajectory plan on anatomical structure captured in an image volume, or the surgical plan may be auto-generated by a surgical planning computer and or by the processor. For example, the surgeon may use an electronic pen to draw on a graphical representation of anatomical structure captured in the image volume to input the surgical trajectory.

The processor performs coarse registration 2704 (synchronizes coordinate systems) between coordinate systems of the optical tracking system (e.g., tracking cameras 200, 326), the robot, and the anatomical structure captured in the image volume. The registration 2704 performed for optical tracking can be relatively roughly approximate while still being able to obtain successful navigated movement of the end-effector to a target pose. For example in a difficult case, if the registration 2704 has an error of several millimeters or is registered to the wrong level, the registration error is substantially reduced by further re-registration responsive to when the US images are generated from the US transducer (once the US transducer comes in skin contact) and structure of the anatomical structure captured in one of the US images is matched to structure of the anatomical structure captured in a selected portion of the image volume. Operations can therefore automatically adjust optical registration to continuously improve accuracy once US imaging data capturing anatomical structure of the patient is obtained from the US transducer.

In the example operational flow, the robot arm is moved 2706 under optical tracking to be close to the target pose. Responsive to when the US imaging becomes activated, it is determined that the target pose is actually shifted to the left by 5 mm. Since the end-effector attached to the robot arm is tracked, the software would then immediately be able to update the optical-tracking-to-CT registration to synchronize with the newly found US-to-CT registration. For example, when the US imaging becomes activated and registration operations match structure of the anatomical structure captured in one of the US images to structure of the anatomical structure captured in the selected portion of the image volume, the operations being performing registration 2708 between coordinate systems of the US tracking system (e.g., US transducer), the robot, and the anatomical structure captured in the image volume. The operations can use the US based registration to improve accuracy of the earlier optical registration between coordinate systems of the optical tracking system (e.g., tracking cameras 200, 326), the robot, and the anatomical structure captured in the image volume through the registration operations 2710 using the determined registration between the US tracking system (e.g., US transducer) and the anatomical structure captured in the image volume. When initially preforming registration of the US transducer, the search region in the image volume can be selected based on the optical tracked location of end-effector. Because US registration is ultimately what is used to perform surgery and accuracy of the optical system is less important due to its lower accuracy and being prone to line-of-sight blockage, skin-mounted arrays tracked by the tracking cameras to simplify the entire registration and navigation process. Alternately, visible light tracking of the patient's body or of visible markings created on the patient's skin (e.g., using ink) provide adequately accurate optical tracking in this workflow.

The processor displays 2712 a current pose (e.g., position and rotational orientation) of the end-effector, e.g., guide tube 2000, relative to the anatomical structure captured in the image volume. The processor determines 2714 whether the end-effector is aligned with a target pose and, if so, the processor performs further operations 2716 associated with being on-target, such as tracking depth and rotation of a surgical instrument guided by the end-effector. In contrast, when the determination 2714 is that the end-effector is not aligned with the target pose, the processor generates 2718 navigation information computed to indicate a direction of movement as needed for the end-effector to reach the target pose and initiates further guided movement of the end-effector toward the target pose using the navigation information.

Hybrid Patient Tracker Utilizing Optical Tracking and US for Noninvasively Tracking Patient Anatomical Structure As explained above, image-guided surgery often requires an invasive surgical process exposing bone to mount a patient reference tracker. Exposing the bone can lead to damage to the bone and soft tissues and infection. It is also time consuming to surgically clear a path to the bone.

Some further embodiments of the present disclosure are directed to an anatomical structure tracker apparatus that includes both a US transducer and an optical tracking array. In some embodiments, the optical tracking array includes a plurality of spaced apart markers. The US transducer is rigidly coupled to and spaced apart from optical tracking array, and is operative to output US imaging data of anatomical structure. The optical tracking array may be configured as an array of, e.g., 3 or 4 reflective optical markers that are tracked as a rigid body by a stereo camera tracking system. Or, the tracking array, which is combined with the US transducer, can be an electromagnetic sensor that electronically streams its 3D position within an electromagnetic field (e.g., Aurora by Northern Digital, Inc.). Additional options exist for tracking such as radiofrequency time-of-flight. The tracking array is mounted rigidly to an array of 1 or more US transducers.

One problem with tracking the spine using camera optical tracking arrays is that the bone must be invasively exposed in order to temporarily attach an optical tracking array to the bone for monitoring movement of the bone, e.g., patient body movement. For example, the optical tracking array is typically attached to a spinous process clamp or to a spike that is driven into the ilium or other bony region near the surgical site. In contrast using an anatomical structure tracker apparatus in accordance with various present embodiments, it is possible to mount the optical tracking array on the skin surface and then to use US transducer rigidly affixed to the optical tracking array to determine pose of the optical tracking array relative to the bone. When the US tracking is performed continuously, the movement of the optical tracking array can be tracked in real time to improve tracking accuracy without requiring a rigid interconnection between the bone and the optical tracking array.

FIG. 28 depicts an anatomical structure tracker apparatus that is configured in accordance with some embodiments.

Referring to FIG. 28, the apparatus includes an optical tracking array 2810 comprising a plurality of spaced apart markers 2812. Apparatus further includes a two-dimensional planar array of US transducers 2802, supported by a rigid base 2800, and connected by a connecting arm to the optical tracking array 2810. Each of the US transducers 2802 is configured to output US pulses and detect returned US reflections of the anatomical structure. Separation between the US transducers 2802 in the array may preferably be as small as possible to maximize resolution of the detected bone surface below the array. A US tracker computer 2820, which may be part of the surgical robot system 100, is configured to receive US imaging data from the US transducers and generate US images of the anatomical structure based on the US imaging data.

The two-dimensional planar array of US transducers 2802 illustrated in FIG. 28 can be, for example, a 7×6 rectangular array of parallel linear US transducers 2802. Each US transducer 2802 is capable of emitting US pulses and detecting reflected US.

Operations for mounting the US transducers 2802 to skin could use adhesive gel, adhesive tape, elastic bands, or other means. As explained above, because of the ability to perform continuous monitoring of movement of the optical tracking array 2810 relative to US tracked anatomical structure, e.g., bone, it is not important for the apparatus to be rigidly mounted to bone and is only necessary that it be mounted so that the US transducers 2802 remain in contact with skin and the optical tracking array 2810 remains in range of and visible to the tracking cameras. Since US transducers generally require gel to conduct US waves from the skin to the probe, a layer of gel could be provided in a center portion of rectangular or ring-shaped adhesive grommets around each individual US transducer to adhere the US transducer to the skin surface. Alternately, gel could be provided in the center of a larger adhesive rectangular or ring-shaped grommet around the entire array of US transducers adhering the array to the skin surface while also maintaining a gel pocket between the skin and transducer.

With the apparatus attached to the patient's skin, each US transducer can operate to detect underlying bone and detect the distance to the underlying bone according to the known speed of sound in the connective tissue below skin surface and dorsal to the vertebrae. With each parallel US transducer detecting the closest proximate contour of the underlying bone, a map of the bony surface could be generated by the US tracker computer 2820.

In some other related embodiments, instead of using an array of parallel linear US transducers, one or more "convex" or "sector" US transducers are used. These US transducers emit US pulses in a fan pattern. When utilizing more than one US transducer, some fan planes can be aligned perpendicular to others, such as shown in FIG. 29. As with the linear array of US transducers, e.g., as shown in FIG. 28, such an array would also be able to detect 3D location of bony prominences under the surface of the skin based on the known pattern and geometry of the fan planes, but would be able to detect bone over a wider region than the linear probe array.

FIG. 29 depicts another anatomical structure tracker apparatus that is configured in accordance with some other embodiments.

Referring to FIG. 29, the apparatus includes the optical tracking array 2810 comprising the plurality of spaced apart markers 2812. The apparatus further includes a US transducer having a linear array of US transducers 2902 each having a major axis and a minor axis, where the major axes of the US transducers in the linear array are parallel. The US transducer also has at least one pair of other US transducers 2904 spaced apart on opposite sides of the linear array of US transducers 2902. Each of the US transducers 2904 in the at least one pair have a major axis and a minor axis, where the major axes of the US transducers 2904 in the at least one pair are parallel and extend in a direction that is substantially perpendicular to a direction of the major axes of the US transducers 2902 in the linear array. A US tracker computer 2820, which may be part of the surgical robot system 100, is configured to receive US imaging data from the US transducers 2902 and 2904 and generate 3D US images of the anatomical structure based on the US imaging data.

The US transducers 2902 and 2904 are mounted to a base plate 2900. In the example of FIG. 29, linear array of US transducers 2902 has 8 convex US transducers which are oriented such that the planes of the fan pattern of emitted US waves from the US transducers 2902 are parallel and are oriented along a first axis of the base plate. There are also two pairs of US transducers 2904 spaced apart on opposite sides of the linear array of US transducers 2902, and which are oriented such that the planes of the fan pattern of emitted US waves from the US transducers 2904 are oriented along another a second axis of the base plate which is perpendicular to the first axis. The fan-shaped planes of US pulse emission are illustrated in FIG. 29 for two of the eight US transducers.

As an alternate to either of the US transducers configurations illustrated in FIGS. 28 and 29, any 3D US transducer can be used to identify 3D locations of detected structures relative to the optical tracking array 2810.

With the surface of a vertebra mapped according using the US transducer(s), the US tracker computer can track movement of the vertebra. In one embodiment, the bony structures detected by US transducer can be treated as natural fiducials. That is, a bony prominence that has a unique structure such as an outcropping or dimple can be identified automatically and then followed from frame to frame of US images generated based on the US imaging data, to keep track of the bone relative to the optical tracking array. If three or more such natural fiducials are identified and followed, there is enough data to compute full rigid body movement of the bone under the skin according to known operations. In this embodiment, the system does not have any information on what part of the anatomy is being imaged, it is simply using the bone as a rigid fixed reference. Therefore, when the patient is in a particular position such as the position at which registration is recorded, the natural fiducials can be considered to be at their zero location. Any movement of the natural fiducials relative to the US transducer can be tracked essentially by detecting the natural fiducial's x, y, z location from the linear US transducer. Then at any given frame of tracking data containing both optical tracking and US tracking, the vertebra position is the hybrid (optical and US) anatomical structure tracker apparatus position as detected by the optical data plus the offset as detected based on the US imaging data.

In another embodiment for tracking movement of the vertebra, the US imaging data is used for registration instead of only being used to follow natural fiducials. That is, the contours of the bony surface as detected by the US transducer are matched against the known bony contours from another medical image such as a CT scan. Bony contours in the CT or MRI image volume are detected using image processing edge detection algorithms. The medical image becomes registered to the tracker as soon as a unique match between bone contours detected by US and bone contours detected in the medical image volume is determined. That is, when the system identifies a contour match, the transformation to get from the medical image coordinate system to the hybrid (optical and US) anatomical structure tracker apparatus coordinate system becomes known. Since the US transducer is in a known position relative to the optical tracking array, i.e., through the rigid coupling therebetween, the camera coordinate system and the CT coordinate system are then co-registered. Thus, the hybrid anatomical structure tracker apparatus serves not only as a non-invasive patient reference array, but also as a means of registration. By using this registration method, no x-rays or additional ionizing radiation are needed to achieve registration.

The workflow for using the hybrid anatomical structure tracker apparatus in registration and tracking could be as follows, and according to some embodiments. First, the patient receives a 3D scan such as a MRI or a CT scan. Then, in the operating room, a hybrid anatomical structure tracker apparatus is adhered to the skin, superficial to the spine level to be operated, with a layer of gel captured between the US transducer the skin. The US transducer is activated, detecting the bones underneath and generating a surface contour map. An algorithm then compares the surface contours as detected from the US transducer to the contours found on the preoperative MM or CT scan, iteratively comparing different regions at different orientations until a match is found. Once a match is found, registration has been achieved between medical image volume and the optical/electromagnetic/radiofrequency tracking coordinate system and other tools such as drills, probes, and screwdrivers can be tracked and images of the tools overlaid on the MRI or CT volume as is commonly done with surgical navigation. After registration, the hybrid anatomical structure tracker apparatus remains in place and serves as a patient tracker, accurately tracking the location of bone by combining optical tracking data with US tracking data.

In some cases, the hybrid anatomical structure tracker apparatus may become obtrusive to the surgeon if it is located directly over the site at which surgery is being performed. In such cases, the hybrid anatomical structure tracker apparatus can be used to register the level of interest and additional similar trackers could be placed nearby over regions that are less obtrusive but still relatively close to the surgical site. After registration is established with the primary device, the transformation between the secondary tracker(s) and primary tracker can be recorded ("registration transfer" as described elsewhere) and then the primary tracker removed. This method assumes that any movement of bone at the location where the primary tracker was mounted would result in equivalent movement of bone at the region where the secondary tracker is mounted. In cases where large bending of the spine may occur, a secondary tracker rostral to the primary site and a tertiary tracker caudal to the primary site could be used and the movement at the primary site calculated as the average of the secondary and tertiary movements.

It may be undesirable to apply US continuously for a long period to the patient. The skin-mounted device could therefore function in different modalities. When needed for registration, the device could apply continuous energy. When monitoring location, the device could pulse intermittently as needed, for example one 100 ms pulse every 2 seconds. Other factors may also be used to trigger when a higher frequency of sampling is needed. For example, if tracking cameras detect acceleration or movement exceeding some threshold, the system could be put into continuous sampling mode until movement ceases. Additionally, if a US pulse detects movement beyond some threshold of the last position, the monitoring algorithm could trigger the system to switch to continuous sampling mode until movement ceases. Finally, an additional sensor such as an accelerometer sensing movement of the apparatus or pressure sensor sensing a change in pressure of the gel chamber could trigger the system to enter continuous sampling mode until a stable state is reached again.

Monitoring Sensitive Anatomical Structures During Spine Surgery

In minimally invasive spine surgery (MIS), sequential dilation is used to gain access from an incision to a surgical target, typically the intervertebral disc space. During dilation the surgeon must monitor the location of sensitive structures, such as nerves, veins, and arteries, in order to avoid serious complications caused by compromising those structures. The specific structures are dependent on the anatomy traversed in a given approach. The sensitive structures of common approaches are described below.

In MIS transforaminal lumbar interbody fusion (TLIF), the intervertebral disc space is commonly accessed through Kambin's Triangle, an anatomical corridor defined by the triangular shape formed by the exiting nerve root, traversing nerve root, and superior vertebral end plate. The surgeon uses this corridor as a safe access space to perform the discectomy and place the interbody device. Accurate targeting of this corridor is crucial to avoid damage to the adjacent nerves.

In lateral lumbar interbody fusion (LLIF), the disc space is commonly accessed through a retroperitoneal approach where the dilator is placed posterior to the peritoneum and traversed through the psoas muscle. In this approach, the disc space must be accurately targeted without violating the peritoneum and lumbar plexus.

The sensitive anatomical structures are typically monitored through direct visualization and/or intraoperative neuromonitoring. Direct visualization involves creating a clear line of sight between the structure and the surgeon's eyes. This approach typically requires a larger incision and access corridor, which is in opposition with benefits of minimally invasive surgery.

Intraoperative neuromonitoring is used to identify real-time damage or insult to nerves by monitoring the electrical activity of the nervous system. Stimulated electromyography (EMG) is a common neuromonitoring modality employed for monitoring the proximity of or irritation to individual nerve roots associated with motor function during spine surgery. The system monitors the change in nerve activity relative to an established baseline. In some systems, the status is reported as color indicators which represent grades of change. Less than 100 mA change is reported as a green indicator, greater than 100 mA change is reported as a yellow indicator, and the lack of a response is indicated as a red indicator. This information is limited as it communicates a relative, quantitative status and does not provide intuitive visualization of the nerve location. In addition, neuromonitoring is limited to monitoring nerve activity and is not capable of monitoring blood vessels.

Various further embodiments of the present disclosure are directed to detecting and providing user notification of the location of nerves, blood vessels, and other sensitive structures using intraoperative US imaging. Detecting these structures with US enables the surgeon to be aware of the structure and its location while accessing the disc space in a minimally invasive approach, rather than relying on larger incisions as in direct visualization or relative status information as in neuromonitoring. Further embodiments are directed to US transducer apparatuses and operations for detecting blood vessels with traditional and navigated access instruments capable of US imaging.

One US imaging modality for non-invasive visualization of anatomical structures, includes nerves and blood vessels. One such application is US guided nerve block, where US is used to identify the target nerve and guide the needle placement. Another application is the use of Doppler US to measure the amount of blood flow through veins and arteries. Doppler US may be coupled with US guided nerve block to monitor the position of a critical vein or artery while the needle is placed. Machine learning can be implemented to generate 3D models from US scans and to measure and visualize bladder volume.

US transducers are available in a variety beam shapes. Traditional handheld US transducers are most commonly convex or linear. Convex transducers contain a curved array of piezoelectric transducers that emit and receive US signals in a convex beam shape. Similarly, linear transducers contain a linear array of transducers that emit and receive signals in a linear beam shape. Endoscopic transducers are significantly smaller, approximately 2 mm in diameter, for use in endoscopic or endobronchial applications. These probes can be provided with convex and radial beam shapes. In endobronchial US (EBUS) lung biopsy applications, the radial EBUS probe spins to generate a radial beam shape and is used locate the tumor in the bronchial tube. The convex EBUS probe is then used to target the tumor with the biopsy needle.

Some embodiments are directed to US transducer apparatuses and operations for visualizing sensitive structures in spine surgery by combining US imaging with traditional and navigated spine access instrumentation. These embodiments may replace or supplement neuromonitoring by providing the surgeon the ability to visualize the location of nerves relative to instrumentation rather than solely depending on relative indicators (i.e. red, yellow, green). The application of US Doppler imaging, which can identify fluid movement, can also be used to provide the surgeon the ability to visualize the location of veins and arteries relative to instrumentation. In addition, machine learning may be implemented to compute 3D models of spine anatomy, including discectomy volume. Each of the modalities may be combined with navigation to register and augment the US image with CT, MM or fluoroscopic images.

In one embodiment of the present disclosure, a US transducer apparatus includes a support wire and a US transducer attached to an end of the support wire. The support wire may be a rigid support wire, such as a "Kirschner wire" or "K-wire" probe. The US transducer may be one of a convex US transducer, a radial US transducer, and a linear US transducer. An interface is provided for communicating US data through a flexible signal wire, which may extend through the support wire, to a computer configured to process the US data.

The computer may be configured to process the US data to generate a graphical representation of anatomical structure sensed by US signals emitted by the US transducer. Alternatively or additionally, the computer may be configured to process the US data to identify nerves and/or blood vessels within the anatomical structure sensed by US signals emitted by the US transducer. The computer includes at least one processor and circuitry configured to drive the US transducer to generate US signal emissions and to condition the return US signals received by the US transducer for processing by the at least one processor.

In spine surgery, long rigid wires, commonly called "Kirschner wires" or "K-wires", are used to probe anatomy and guide instruments and implants to the anatomical targets. K-wires are typically guided to the target using fluoroscopic imaging. Once the K-wire is placed, larger profile instruments or implants are guided over the K-wire, which is typically anchored in the anatomy. For example, K-wires are used to guide cannulated pedicle screws safely through the pedicle trajectory. K-wires are also commonly inserted into the intervertebral disc and used to guide sequential dilators and maintain the position of the dilator relative to the disc during retractor or port placement.

Various embodiments the present disclosure may remove the need for or supplement fluoroscopy by allowing the surgeon to monitor the location of nerves and blood vessels while guiding the K-wire into position. The present wire-like US transducer apparatus and the operationally coupled computer are configured to provide visualization of the position of anatomical structures through 2D US imaging, identifying nerves and blood vessels apart from other anatomy, identifying blood flow using US Doppler imaging, and constructing 3D models of anatomical structures including discectomy volume using 3D US imaging.

As described above, a flexible signal wire is used to transfer the US data (e.g., US wave signals) to a computer for processing. The support wire can be flexible to facilitate tip positioning during a procedure.

In some embodiments, a wireless communication interface may be provided between the US transducer and the computer, thereby eliminating or reducing the length of the flexible signal wire extending between the US transducer and a wireless transmitter. In one embodiment, a processor is mounted on the proximal end of the support wire and coupled to the US transducer to receive US data and further coupled to a wireless transmitter to transmit the US data to the computer. As used herein, US data may be an analog US signal or digital representation thereof. The US transducer, the processor, and the wireless transmitter may be powered by a proximally located battery.

A machine learning model may be used to process the US data to identify specific types of anatomical structures. The machine learning model may be a neural network or other computer algorithm that is trained to identify the US reflection appearance of specific types of anatomical structures. The machine learning model may be trained to differentiate among learned US reflection appearances of different types of anatomical structures, which may be obtained a database, to identify which type of anatomical structure is likely the source of the observed US reflection. The machine learning model can be trained using data characterizing US reflection appearances of known anatomical structures, which could be provided through computational modeling of the anatomical structures or through expert US users labeling the anatomical structures in US images generated from US data.

The US transducer apparatus may require rotation during a surgical procedure. Rotation at the tip may be manually applied by rotating the entire apparatus or rotating a mechanism at the base of the apparatus that extends within the support wire, e.g., with rotation of the US transducer occurring within a sheath across a bearing surface. Alternately, US transducer rotation may be provided using a miniature motor mounted near the tip of the support wire, between the support wire and the US transducer, that is powered using, e.g., electrical wires that traverse the shaft alongside the US signal wires.

Figure 30:
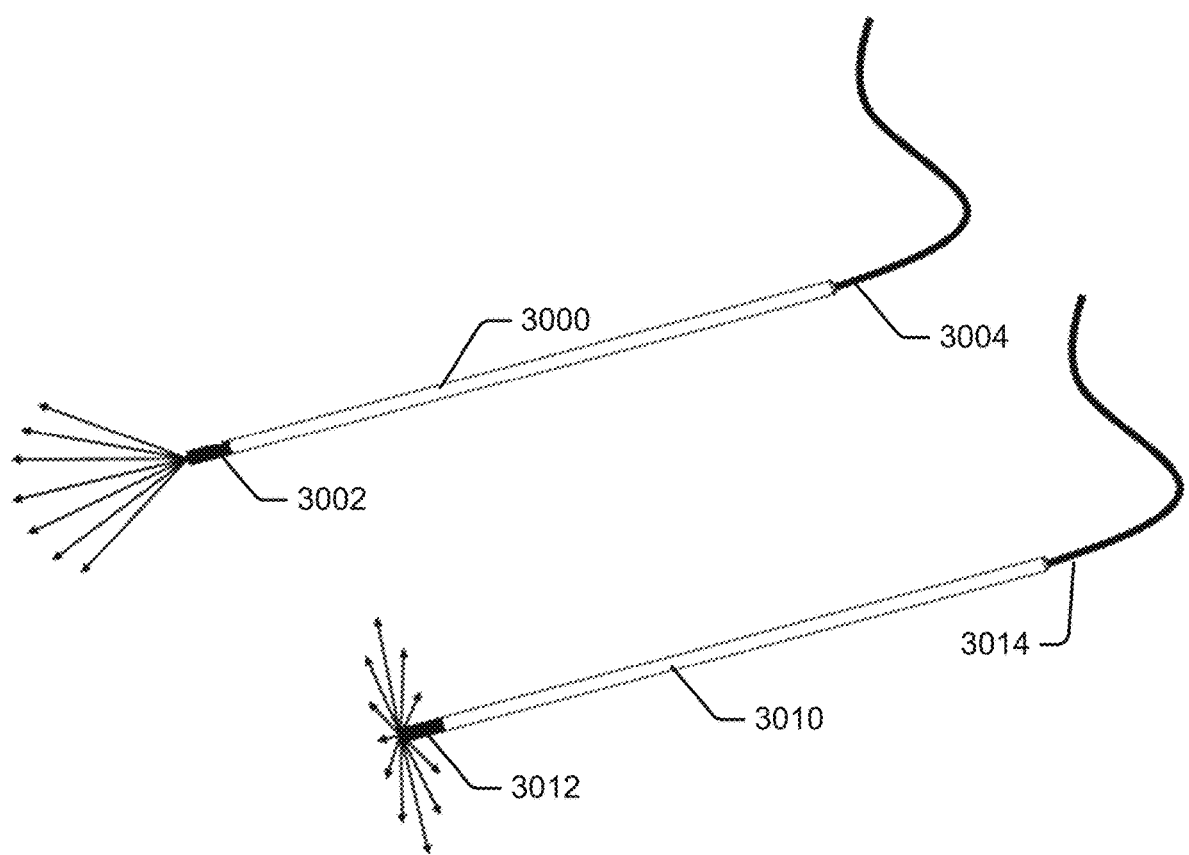

FIG. 30 depicts a US transducer apparatus which includes a support wire 3000 connected to a convex US transducer 3002 which communicates US image data through a flexible signal wire 3004 to a computer, in accordance with some embodiments. FIG. 30 also depicts another US transducer apparatus which includes a support wire 3010 connected to a radial US transducer 3012 which communicates US image data through a flexible signal wire 3014 to a computer, in accordance with some embodiments.

Figure 31:
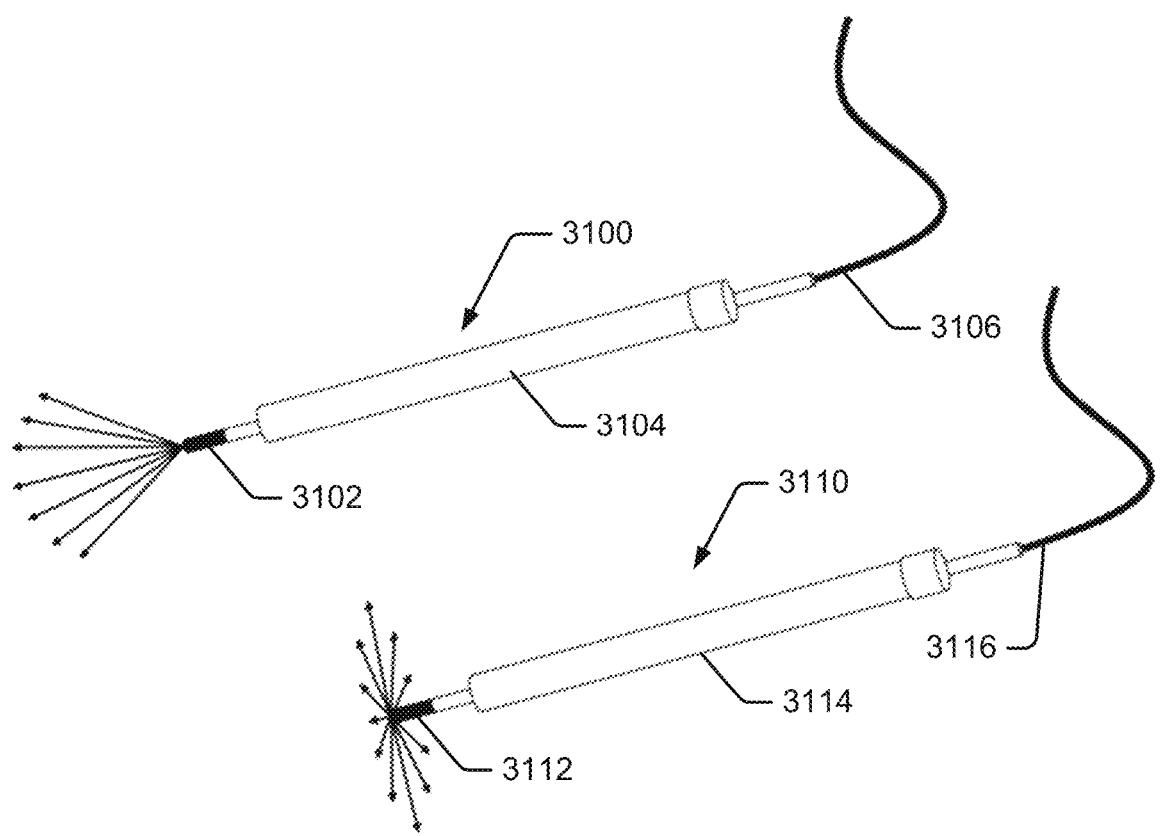

FIG. 31 depicts another embodiment of a US transducer apparatus 3100 which includes a support wire (which may be similar to a "K-wire"), which is temporarily inserted through a dilator (Cannula) 3104 having an inner void through which the support wire extends and can be removed. The apparatus further includes a convex US transducer 3102 attached to a distal tip of the support wire and/or the cannulated dilator 3104. A flexible signal wire 3106 or other communication interface carries the US data from the US transducer 3102 to the computer.

FIG. 31 also depicts another embodiment of a US transducer apparatus 3110 which includes a support wire (which may be similar to a "K-wire"), which is temporarily inserted through a dilator (Cannula) 3114 having an inner void through which the support wire extends and can be removed. The apparatus 3110 further includes a radial US transducer 3112 attached to a distal tip of the support wire and/or the cannulated dilator 3114. A flexible signal wire 3116 or other communication interface carries the US image data from the US transducer 3112 to the computer.

These removable US transducer apparatuses 3102, 3112 can be connected to the computer configured to generate the graphical visualizing of the position of anatomical structures since using ultrasound, to identify nerves and blood vessels apart from other anatomy (which may use machine learning), to identify blood flow using Doppler imaging, and to construct 3D models of anatomical structures including discectomy volume. The US transducers 3102, 3112 may be attached to the cannulated dilator 3104, 3114 through various mechanisms, including threads, friction, magnets, clamps, etc. The attachment mechanism can include a bearing surface or sheath to allow the US transducers 3102, 3112 to rotate during imaging as required for radial transducers. A potential advantage of one or more of these embodiments is that a US transducer apparatus is provided that can be inserted by a surgeon using a surgical procedure developed for rigid wires, such as K-wires.

Figure 32:
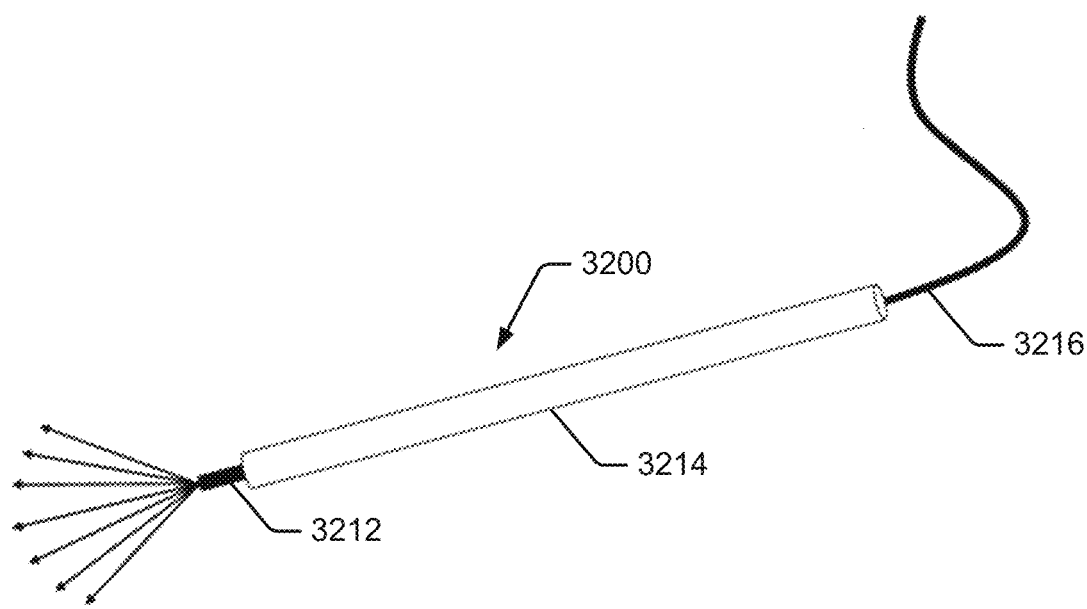

FIG. 32 illustrates another US transducer apparatus 3200 configured in accordance with some embodiments. The US transducer apparatus 3200 includes a dilator (Cannula) 3214 containing a permanent integrated rigid wire, which may be similar to a "K-wire". The apparatus 3200 further includes a convex US transducer 3212 attached to a distal tip of the cannulated dilator 3214. A flexible signal wire 3216 or other communication interface carries the US data from the US transducer 3212 to the computer. The computer may be configured to process the US data to generate graphical visualization of the position of anatomical structures, identify nerves and blood vessels apart from other anatomy using machine learning, identify blood flow using Doppler imaging, and construct 3D models of anatomical structures including discectomy volume.

Figure 33:
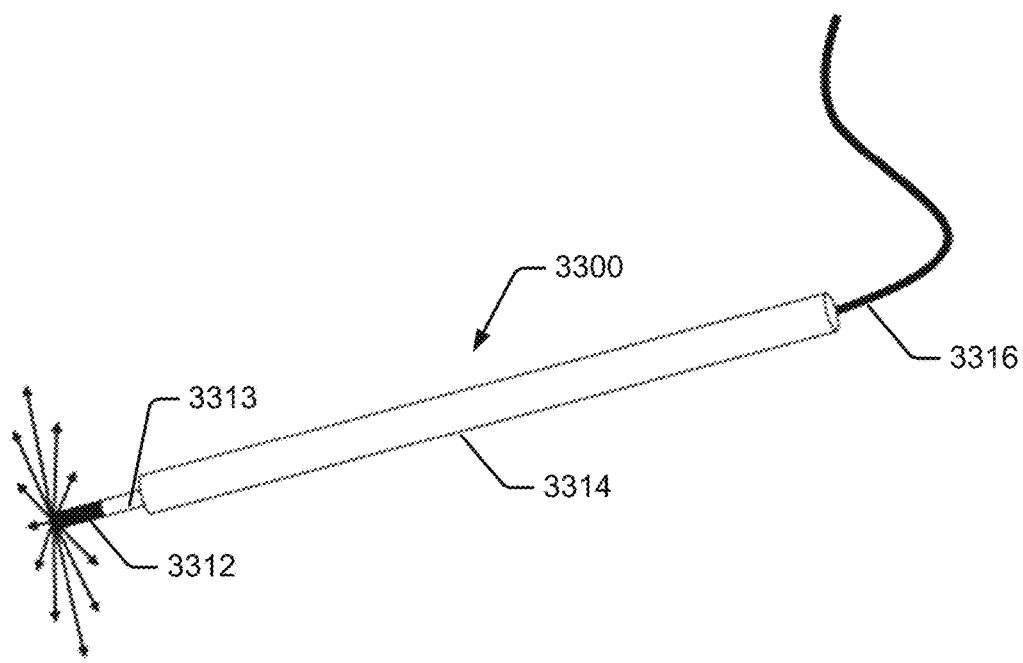

FIG. 33 illustrates another US transducer apparatus 3300 configured in accordance with some embodiments. The US transducer apparatus 3300 includes a dilator (Cannula) 3314 containing a permanent integrated rigid wire, which may be similar to a "K-wire". The apparatus 3300 further includes a convex US transducer 3312 is attached to the dilator 3314 through a bearing 3314 or sheath which allows rotation of the US transducer 3312 relative to the dilator 3314. A flexible signal wire 3316 or other communication interface carries the US data from the US transducer 3312 to the computer. The computer may be configured to process the US data to generate graphical visualization of the position of anatomical structures, identify nerves and blood vessels apart from other anatomy using machine learning, identify blood flow using Doppler imaging, and construct 3D models of anatomical structures including discectomy volume.

Figure 34:
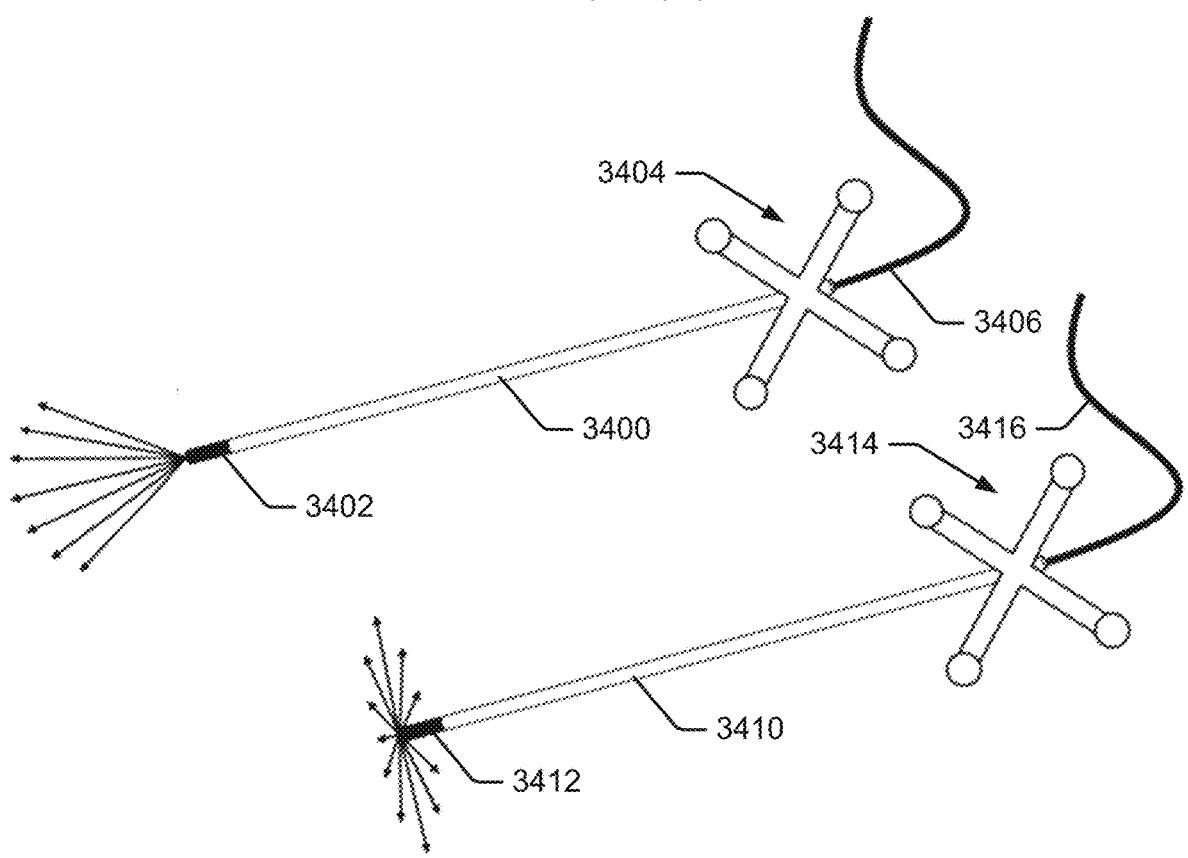

FIG. 34 depicts a US transducer apparatus which includes a support wire 3400 and a convex US transducer 3402 connected to the support wire 3400. The convex US transducer 3402 is operable to communicate US data through a flexible signal wire 3406 to a computer. In accordance with some embodiments, an optical tracking array 3404 comprising a plurality of spaced apart markers is attached to the support wire 3400 at a location spaced apart from the convex US transducer 3402.

FIG. 34 also depicts another US transducer apparatus which includes a support wire 3410 and a radial US transducer 3412 connected to the support wire 3410. The radial US transducer 3412 is operable to communicate US data through a flexible signal wire 3416 to a computer. In accordance with some embodiments, an optical tracking array 3414 comprising a plurality of spaced apart markers is attached to the support wire 3410 at a location spaced apart from the radial US transducer 3412.

By integrating an optical tracking array into the US transducer apparatus, the US transducer pose may be tracked using a surgical navigation system. Tracking pose of the US transducer enables the processor to computationally merge the US image with the primary navigation image, such as CT, MRI, or fluoroscopy. Navigation also allows the US transducer to be graphically represented relative to the primary navigation image. In addition, by using the optical tracking array to track the US transducer the computer can be configured to generate 3D US images. 3D US images can be used as the stand-alone navigation image or could be used to update the registration of the primary navigation image.

Updating registration is useful because the US transducer apparatus itself can alter the configuration of anatomical structures through normal pressure applied, reducing accuracy of primary rigid body navigation. Even if the US transducer apparatus causes changes to the deep anatomy relative to the surface, by providing a rough location within the image volume of the tool tip, it is computationally easier to find a match of the US image contours to the CT or MRI image contours within the search area defined by navigation than if the entire image volume is searched. Finally, integrating navigation is useful because tracking the US transducer during US scanning facilitates measuring volumes from the 3D US images. For example, it would be possible to measure the size of tumors or the extent of a discectomy. The following embodiments build on those described above with the addition of optical tracking arrays, which may be detachable or permanently fixed to the US transducer apparatus.

Figure 35:
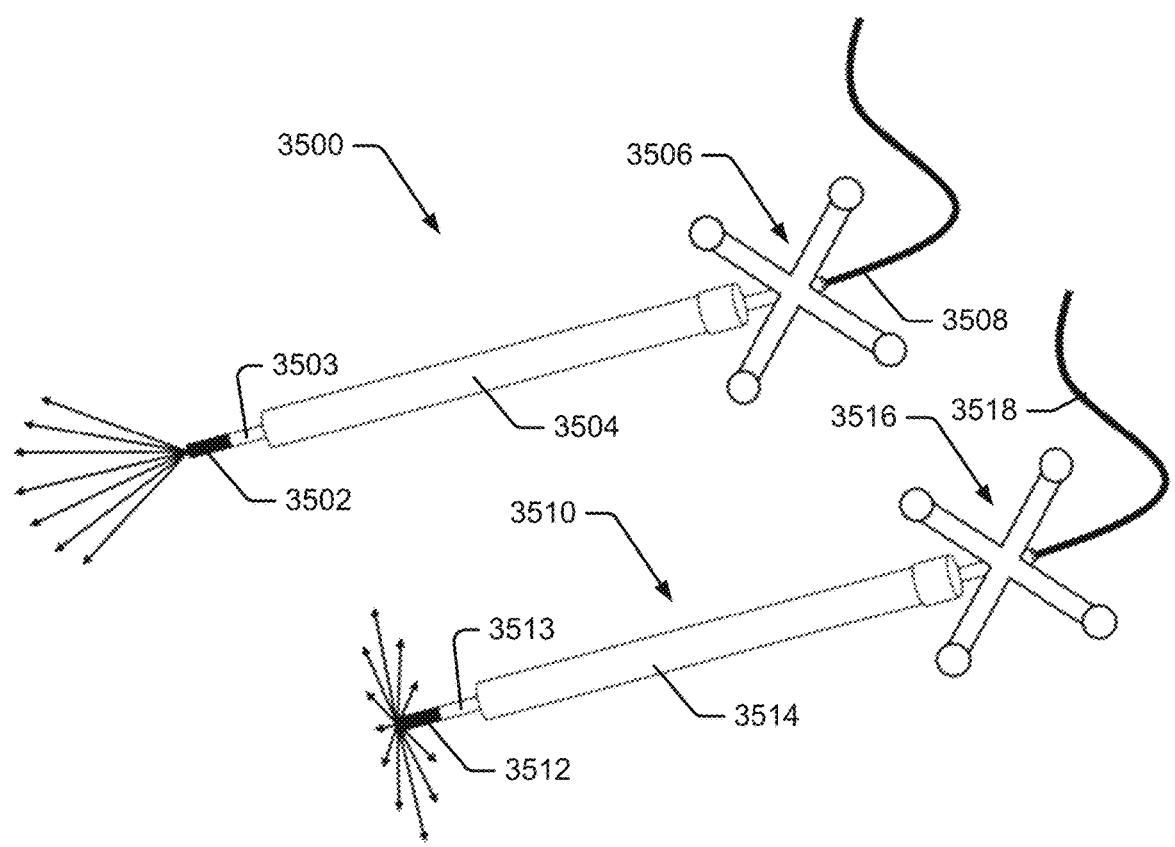

FIG. 35 depicts a US transducer apparatus 3500 which includes a support wire 3503 extending from a flexible signal wire 3508 through a dilator 3504 to connect to a convex US transducer 3502. The convex US transducer 3502 is operable to communicate US data through the flexible signal wire 3508 to a computer. In accordance with some embodiments, an optical tracking array 3506 comprising a plurality of spaced apart markers is attached to the support wire 3503 at a location spaced apart from the convex US transducer 3502.

FIG. 35 also depicts another US transducer apparatus 3510 which includes a support wire 3513 extending from a flexible signal wire 3518 through a dilator 3514 to connect to a radial US transducer 3512. The radial US transducer 3512 is operable to communicate US data through the flexible signal wire 3518 to a computer. In accordance with some embodiments, an optical tracking array 3516 comprising a plurality of spaced apart markers is attached to the support wire 3513 at a location spaced apart from the convex US transducer 3512.

Figure 36:
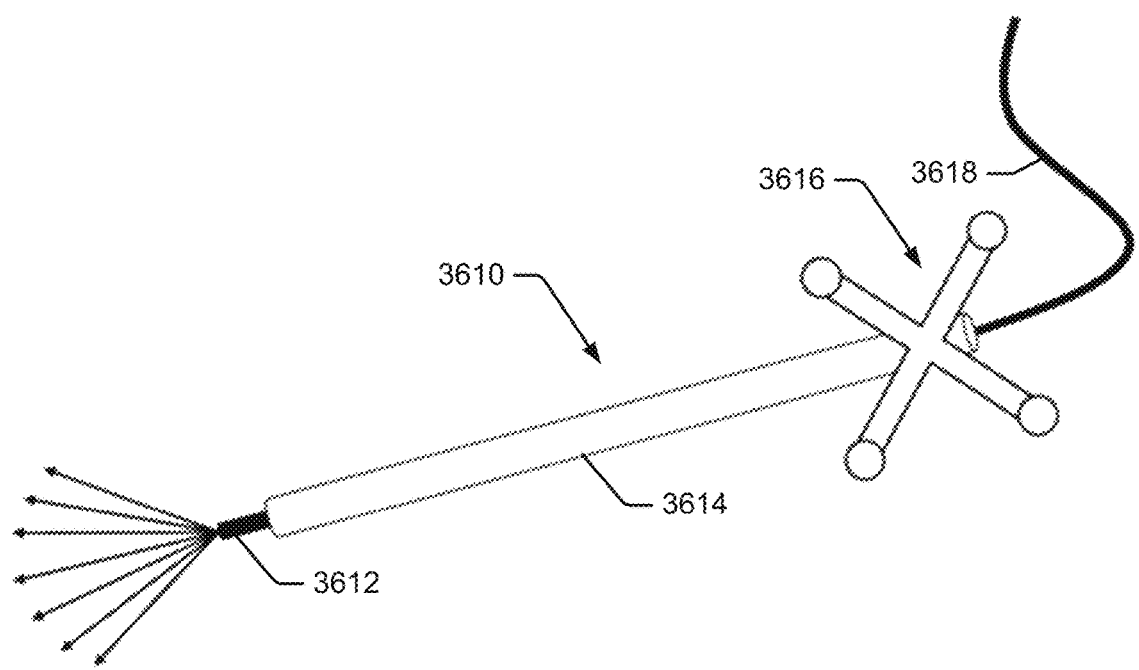

FIG. 36 depicts another US transducer apparatus 3610 which is permanently integrated into a dilator 3614 connected to a convex US transducer 3612. The convex US transducer 3612 is operable to communicate US data through a flexible signal wire 3618 to a computer. In accordance with some embodiments, an optical tracking array 3616 comprising a plurality of spaced apart markers is attached to the dilator 3614 at a location spaced apart from the convex US transducer 3612.

Figure 37:
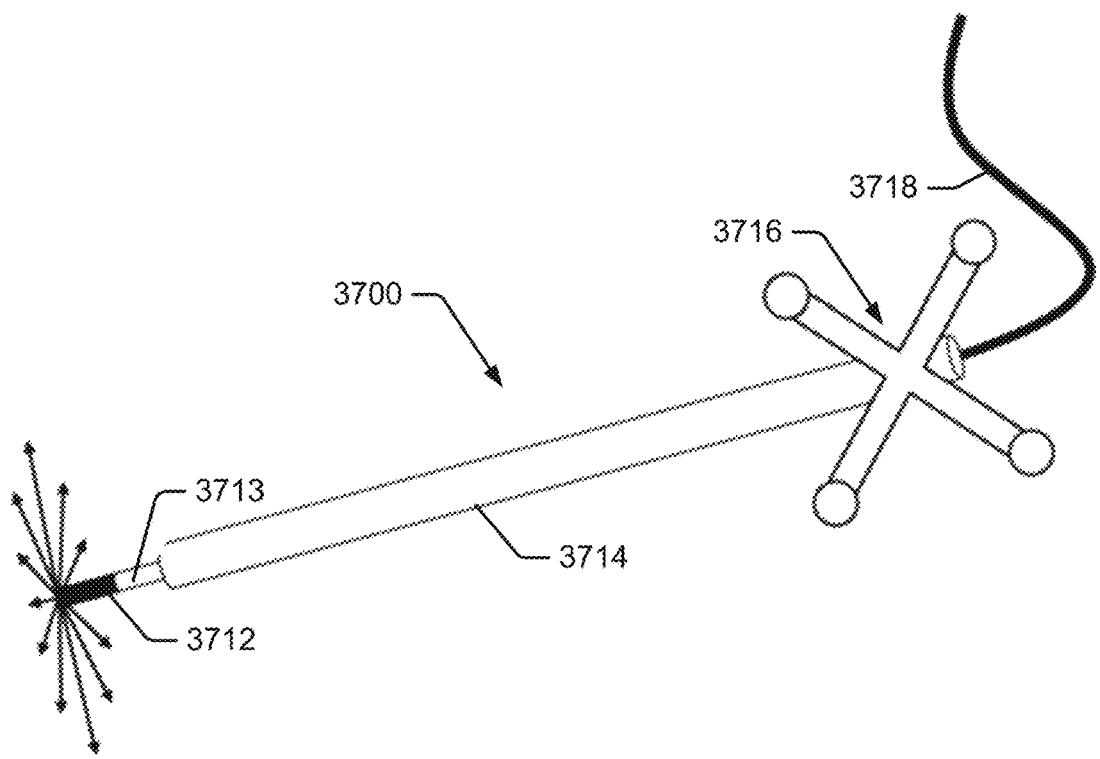

FIG. 37 depicts another US transducer apparatus 3700 which is permanently integrated into a dilator 3714 connected to a radial US transducer 3712 through a bearing 3713 which allows rotation of the radial US transducer 3712 relative to the dilator 3714. The radial US transducer 3712 is operable to communicate US data through a flexible signal wire 3718 to a computer. In accordance with some embodiments, an optical tracking array 3716 comprising a plurality of spaced apart markers is attached to the dilator 3714 at a location spaced apart from the radial US transducer 3712.

Some embodiments of US transducer apparatuses described above have utilized rigid dilators and support wires. In some other embodiments the support wire and dilator are flexible to allow curvature during surgical procedures. Allowing curvature can allow more adaptable positioning to reach certain anatomical structures, such as the underside of ribs, while still being trackable using a combination of US and optical tracking.

Figure 38:
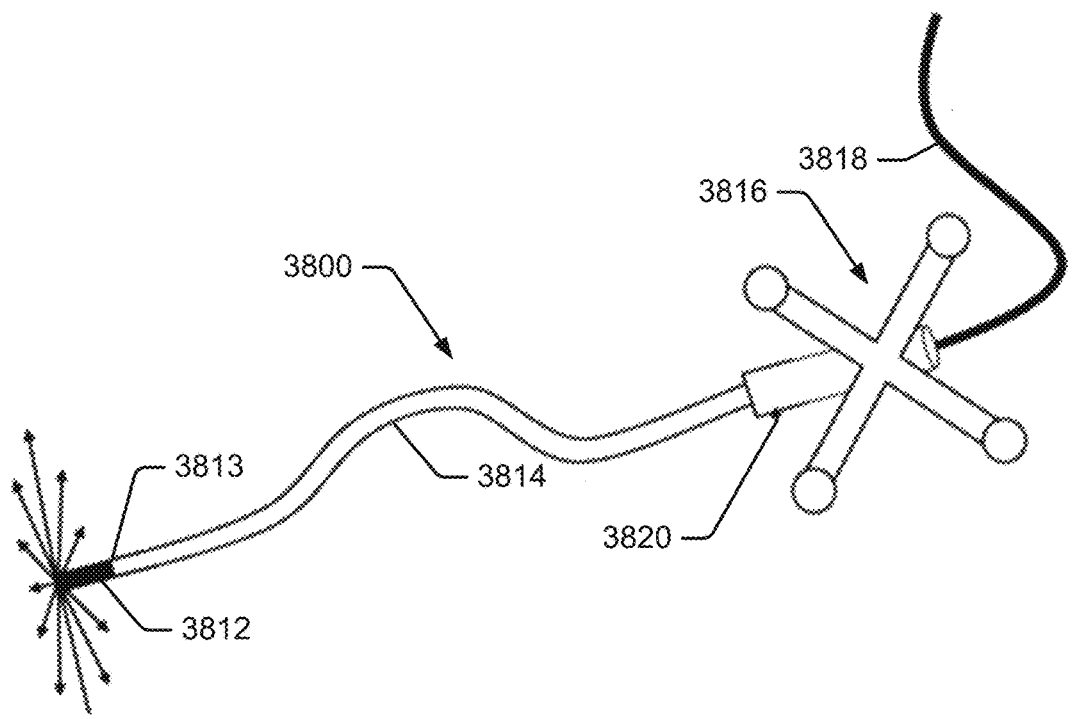

FIG. 38 depicts a US transducer apparatus 3800 which includes a dilator or semi-rigid tube 3814 connected to a radial US transducer 3812 through a bearing 3813 which allows rotation of the radial or convex US transducer 3812 relative to the dilator 3814. The radial or convex US transducer 3812 is operable to communicate US data through a flexible signal wire 3818 to a computer. In accordance with some embodiments, an optical tracking array 3816 comprising a plurality of spaced apart markers is attached to the dilator 3814 at a location spaced apart from the radial US transducer 3812.

Positional tracking of the tip of the US transducer 3812 can be performed using a sensor that senses the position of the dilator without relying on a rigid extension to extrapolate the tip position from the optical tracking array 3816. Some embodiments track the tip of the US transducer 3812 connected to the flexible dilator 3814 using electromagnetic tracking, radiofrequency time-of-flight tracking, or fiber-optic tracking to augment optical tracking of the optical tracking array 3816.

In one embodiment, a fiber optic element extends down a length of the flexible dilator or tube 3814 or other flexible support wire connected to the US transducer 3812, and is configured to sense variation in curvature of the flexible dilator or tube 3814 or other flexible support wire. The fiber optic element may include a Fiber Bragg Grating sensor (FBGS) 3820 configured to sense variation in curvature of the flexible dilator or tube 3814 or other flexible support wire. The fiber optic element can be configured to communicate curvature sensing data through the flexible signal wire 3818 to the computer which is configured to track location of the fiber optic element.

In a further embodiment which uses fiber-optic tracking to augment optical tracking, a fiber-optic element such as a FBGS element extends down the length of the probe alongside the US signal wires. Using methods described for FBGS, the bending of the flexible dilator 3814 to track the tip position and, thereby, the proximal position of an attached US transducer 3812. After registration of tracking to MM or CT image volume, the processor can be configured to navigate the US transducer 3812 within the body, approximating where within the MM or CT image volume the tip is located. Because the tissue pathway within the body deforms in response to pressure from the US transducer 3812 and flexible dilator 3814, the position would not be exact. However, the processor can use a shape-matching algorithm to determine which anatomical structures from the MM or CT are being imaged by the US transducer 3812, further refining the navigated probe tip location accuracy.

Further Definitions and Embodiments

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, micro-code, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A surgical robot system comprising:
   a robot having a robot base, a robot arm coupled to the robot base, and an end-effector coupled to the robot arm, the end-effector configured to guide movement of a surgical instrument;
   an ultrasound (US) transducer coupled to the end-effector and operative to output US imaging data of anatomical structure proximately located to the end-effector; and
   at least one processor operative to obtain an image volume for the patient and to track pose of the end-effector relative to anatomical structure captured in the image volume based on the US imaging data.

2. The surgical robot system of claim 1, wherein to track pose of the end-effector relative to the anatomical structure captured in the image volume based on the US imaging data, the at least one processor is operative to:
   generate US images of the anatomical structure based on the US imaging data;
   match the anatomical structure captured in one of the US images to the anatomical structure captured in the image volume; and
   determine the pose of the end-effector relative to the anatomical structure captured in the image volume based on the matching.

3. The surgical robot system of claim 1, wherein the end-effector comprises a guide tube configured to guide movement of the surgical instrument through the guide tube, and the US transducer comprises an array of US transducers spaced apart along a leading edge of the guide tube.

4. The surgical robot system of claim 3, wherein the US transducers are spaced apart to form a ring shape and are at least partially disposed within the leading edge of the guide tube.

5. The surgical robot system of claim 1, wherein the US transducer comprises a planar array of US transducers connected by a mounting arm to the end-effector.

6. The surgical robot system of claim 1, wherein the at least one processor is further operative to:
   identify in the US imaging data locations of discrete features which are spaced apart along the surgical instrument and sensed by the US transducer; and
   determine pose of the surgical instrument relative to the end-effector based on the locations of the discrete features identified in the US imaging data.

7. The surgical robot system of claim 6, further comprising the surgical instrument having a shaft with the discrete features configured as indentations, protrusions, slots, and/or holes spaced apart along a surface of the surgical instrument.

8. The surgical robot system of claim 6, wherein:
the US transducer comprises an array of US transducers; and
to determine pose of the surgical instrument relative to the end-effector based on the locations of the discrete features identified in the US imaging data, the at least one processor is operative to:
determine depth of the surgical instrument relative to a location on the end-effector based on counting a number of the discrete features identified in the US imaging data from individual ones of the US transducers; and
determine rotation of the surgical instrument relative to the end-effector based on identifying rotation of the discrete features identified in the US imaging data between adjacent US transducers in the array.

9. The surgical robot system of claim 6, wherein to determine pose of the surgical instrument relative to the end-effector based on the locations of the discrete features identified in the US imaging data, the at least one processor is operative to:
match a spatial pattern of the locations of the discrete features identified in the US imaging data to content of a template for the surgical instrument which defines a pattern of the discrete features arranged around the surface of the surgical instrument as a function of locations along a length of the surgical instrument.

10. The surgical robot system of claim 1, wherein the at least one processor is further operative to:
identify in the US imaging data locations of layers of materials of the surgical instrument, wherein adjacent layers of the materials have different reflectivity to ultrasound; and
determine pose of the surgical instrument relative to the end-effector based on the locations of the layers of materials of the surgical instrument identified in the US imaging data.

11. The surgical robot system of claim 10, further comprising the surgical instrument having a shaft with layers of materials stacked along a primary axis of the shaft, wherein adjacent layers of the materials have different reflectivity to US.

12. The surgical robot system of claim 10, further comprising the surgical instrument having a shaft with layers of materials forming helical stripes spiraling about a primary axis of the shaft, wherein adjacent layers of the materials have different reflectivity to US.

13. The surgical robot system of claim 10, further comprising the surgical instrument having a shaft with layers of materials forming stripes extending parallel to a primary axis of the shaft, wherein adjacent layers of the materials have different reflectivity to US.

14. A surgical robot system comprising:
a robot having a robot base, a robot arm coupled to the robot base, and an end-effector coupled to the robot arm, the end-effector configured to guide movement of a surgical instrument;
an ultrasound (US) transducer coupled to the end-effector and operative to output US imaging data of anatomical structure proximately located to the end-effector; and
at least one processor operative to obtain an image volume for the patient and to track pose of the end-effector relative to anatomical structure captured in the image volume based on the US imaging data,
wherein the at least one processor is further operative to:
determine a target pose for the surgical instrument based on a surgical plan defining where a surgical procedure is to be performed using the surgical instrument on the anatomical structure captured in the image volume; and
generate steering information based on the target pose for the surgical instrument and a present tracked pose of the end-effector relative to the anatomical structure captured in the image volume, the steering information indicating where the surgical instrument and/or the end-effector need to be moved.

15. The surgical robot system of claim 14, further comprising at least one motor operatively connected to move the robot arm relative to the robot base, and wherein the at least one processor is operative to:
control movement of the at least one motor based on the steering information to guide movement of the end-effector so the surgical instrument becomes positioned with the target pose.

16. The surgical robot system of claim 1, further comprising kinematic sensors connected to the robot arm and operative to output kinematic movement data indicating change in pose of the robot arm relative to the robot base, and wherein the at least one processor is operative to:
after tracking pose of the end-effector relative to the anatomical structure captured in the image volume based on the US imaging data for a period of time and responsive to the US transducer ceasing to output US imaging data of the anatomical structure proximately located to the end-effector, trigger continued tracking of the pose of the end-effector relative to the anatomical structure captured in the image volume based on the kinematic movement data; and
responsive to the US transducer resuming output of US imaging data of the anatomical structure proximately located to the end-effector, trigger continued tracking of the pose of the end-effector relative to the anatomical structure captured in the image volume based on the US imaging data.

17. The surgical robot system of claim 16, wherein to trigger continued tracking of the pose of the end-effector relative to the anatomical structure captured in the image volume based on the US imaging data, the at least one processor is operative to:
generate US images of the anatomical structure based on the US imaging data;
select a portion of the image volume based on a present pose of the end-effector as tracked relative to the anatomical structure captured in the image volume based on the kinematic movement data;
match structure of the anatomical structure captured in one of the US images to structure of the anatomical structure captured in the selected portion of the image volume; and
determine the pose of the end-effector relative to the anatomical structure captured in the selected portion of the image volume based on the matching.

18. The surgical robot system of claim 16, wherein the at least one processor is further operative to:
display a graphical representation of the end-effector with the determined pose relative to a graphical representation of the anatomy captured in the image volume; and
use a different color and/or shading to display the graphical representation of the end-effector relative to the graphical representation of the anatomy captured in the image volume to visually indicate to a user when the pose of the end-effector relative to the anatomical structure captured in the image volume is being tracked based on the US imaging data distinguishable by the user from when the pose of the end-effector relative to the anatomical structure captured in the image volume is being tracked based on the kinematic movement data.

19. The surgical robot system of claim 1, further comprising a tracking camera operative to track pose of markers on the robot arm and/or the end-effector, and wherein the at least one processor is operative to:
- after tracking pose of the end-effector relative to the anatomical structure captured in the image volume based on the US imaging data for a period of time and responsive to the US transducer ceasing to output US imaging data of the anatomical structure proximately located to the end-effector, trigger continued tracking of the pose of the end-effector relative to the anatomical structure captured in the image volume based on output of the tracking camera; and
- responsive to the US transducer resuming output of US imaging data of the anatomical structure proximately located to the end-effector, trigger continued tracking of the pose of the end-effector relative to the anatomical structure captured in the image volume based on the US imaging data.

20. A surgical robot system comprising:
- a robot having a robot base, a robot arm coupled to the robot base, and an end-effector coupled to the robot arm, the end-effector configured to guide movement of a surgical instrument;
- an ultrasound (US) transducer coupled to the end-effector and operative to output US imaging data of anatomical structure proximately located to the end-effector; and
- at least one processor operative to obtain an image volume for the patient and to track pose of the end-effector relative to anatomical structure captured in the image volume based on the US imaging data;
- wherein a tracking camera operative to capture location of markers on the robot arm and/or the end-effector, and wherein the at least one processor is operative to:
- track pose of the markers;
- after tracking pose of the end-effector relative to the anatomical structure captured in the image volume based on the US imaging data for a period of time and responsive to the US transducer ceasing to output US imaging data of the anatomical structure proximately located to the end-effector, trigger continued tracking of the pose of the end-effector relative to the anatomical structure captured in the image volume based on output of the tracking camera; and
- responsive to the US transducer resuming output of US imaging data of the anatomical structure proximately located to the end-effector, trigger continued tracking of the pose of the end-effector relative to the anatomical structure captured in the image volume based on the US imaging data.

* * * * *